United States Patent
Chiu et al.

(10) Patent No.: US 11,078,263 B2
(45) Date of Patent: Aug. 3, 2021

(54) FC γ RIII BINDING FIBRONECTIN TYPE III DOMAINS, THEIR CONJUGATES AND MULTISPECIFIC MOLECULES COMPRISING THEM

(71) Applicant: Janssen Biotech, Inc., Horsham, PA (US)

(72) Inventors: Mark Chiu, Paoli, PA (US); Brian Whitaker, Exton, PA (US); Di Zhang, Hillsborough, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 78 days.

(21) Appl. No.: 16/111,360

(22) Filed: Aug. 24, 2018

(65) Prior Publication Data

US 2019/0062420 A1    Feb. 28, 2019

Related U.S. Application Data

(60) Provisional application No. 62/550,152, filed on Aug. 25, 2017.

(51) Int. Cl.

| | | |
|---|---|---|
| *C07K 14/435* | (2006.01) | |
| *C07K 14/47* | (2006.01) | |
| *C07K 14/78* | (2006.01) | |
| *C07K 16/18* | (2006.01) | |
| *C07K 19/00* | (2006.01) | |
| *A61K 38/17* | (2006.01) | |
| *A61K 38/39* | (2006.01) | |
| *A61K 39/395* | (2006.01) | |
| *C07K 16/24* | (2006.01) | |
| *A61P 35/00* | (2006.01) | |
| *C07K 16/28* | (2006.01) | |
| *C12N 15/70* | (2006.01) | |

(52) U.S. Cl.
CPC ............ *C07K 16/241* (2013.01); *A61K 38/17* (2013.01); *A61K 38/39* (2013.01); *A61K 39/3955* (2013.01); *A61P 35/00* (2018.01); *C07K 14/47* (2013.01); *C07K 14/78* (2013.01); *C07K 16/18* (2013.01); *C07K 16/283* (2013.01); *C07K 16/2875* (2013.01); *C07K 16/2878* (2013.01); *C07K 19/00* (2013.01); *C07K 14/435* (2013.01); *C07K 2317/31* (2013.01); *C07K 2317/52* (2013.01); *C07K 2317/565* (2013.01); *C07K 2317/71* (2013.01); *C07K 2317/732* (2013.01); *C07K 2317/75* (2013.01); *C07K 2317/76* (2013.01); *C07K 2317/94* (2013.01); *C07K 2318/20* (2013.01); *C12N 15/70* (2013.01)

(58) Field of Classification Search
CPC .. A61K 38/1774; A61K 38/17; A61K 38/177; A61K 38/39; C07K 14/70535; C07K 14/47; C07K 14/78; C07K 2317/17; C07K 2317/622; C07K 2317/92
See application file for complete search history.

(56) References Cited

U.S. PATENT DOCUMENTS

| | | | |
|---|---|---|---|
| 5,635,483 A | 6/1997 | Pettit et al. | |
| 5,780,588 A | 7/1998 | Pettit et al. | |
| 5,856,456 A | 1/1999 | Whitlow et al. | |
| 7,842,476 B2 | 11/2010 | McGregor et al. | |
| 8,278,419 B2 | 10/2012 | Jacobs et al. | |
| 9,200,273 B2* | 12/2015 | Diem ..................... | C40B 50/06 |
| 2005/0038229 A1 | 2/2005 | Lipsovek et al. | |
| 2010/0216708 A1* | 8/2010 | Jacobs .................... | A61P 15/00 514/1.1 |
| 2010/0221248 A1* | 9/2010 | Wittrup ................. | C07K 16/30 424/133.1 |
| 2011/0274623 A1 | 11/2011 | Jacobs | |
| 2012/0321626 A1* | 12/2012 | Zhou ....................... | A61P 43/00 424/136.1 |
| 2013/0079243 A1 | 3/2013 | Diem et al. | |
| 2013/0226834 A1 | 8/2013 | Gannalo, II | |
| 2014/0010812 A1* | 1/2014 | Ravetch ............ | A61K 39/3955 424/134.1 |
| 2014/0113370 A1* | 4/2014 | Camphausen ......... | C07K 16/40 435/328 |
| 2014/0141000 A1* | 5/2014 | Chiu ...................... | A61P 35/04 424/136.1 |
| 2014/0377284 A1 | 12/2014 | Simons et al. | |
| 2015/0158947 A1 | 6/2015 | Cojocaru et al. | |
| 2015/0210756 A1 | 7/2015 | Torres et al. | |
| 2016/0326232 A1 | 11/2016 | Cardosa, et al. | |
| 2018/0044430 A1 | 2/2018 | Chiu et al. | |

FOREIGN PATENT DOCUMENTS

| | | |
|---|---|---|
| WO | WO1988/01649 A1 | 3/1988 |
| WO | WO1992/01047 A1 | 1/1992 |
| WO | WO1994/13804 A1 | 6/1994 |
| WO | WO1998/44001 A1 | 8/1998 |
| WO | WO 02/088172 A2 | 11/2002 |
| WO | WO2009/085462 A1 | 7/2009 |

OTHER PUBLICATIONS

Batori et al. Exploring the potential of the monobody scaffold: effects of loop elongation on the stability of a fibronectin type III domain. Protein Engineering 15(12): 1015-1020, 2002.*
Bork, A. Powers and pitfalls in sequence analysis: the 70% hurdle. Genome Res 10: 398-400, 2000.*
Bork et al. Go hunting in sequence databases but watch out for the traps. Trends Genetics 12(10): 425-427, 1996.*
Brenner et al. Errors in genome annotation. Trends Genetics 15(4): 132-133, 1999.*

(Continued)

*Primary Examiner* — Bridget E Bunner
(74) *Attorney, Agent, or Firm* — Kirk Baumeister

(57) ABSTRACT

FN3 domains that specifically bind FcγRII, their conjugates and antibody fusions, isolated nucleotides encoding the molecules, vectors, host cells, and methods of making and using them.

13 Claims, 1 Drawing Sheet
Specification includes a Sequence Listing.

(56) References Cited

OTHER PUBLICATIONS

Doerks et al. Protein annotation:detective work for function prediction. Trends in Genet 14(6): 248-250, 1998.*
Koide et al. Target-binding proteins based on the 10th human fibronectin type III domain (10Fn3). Methods Enzymology 503: 135-156, 2012.*
Lipovsek, D. Adnectins: engineered target-binding protein therapeutics. Protein Eng Design Selection 24(1-2): 3-9, 2011.*
Ngo et al. Computational complexity, protein structure prediction, and the Levinthal paradox. The Protein Folding Problem and Tertiary Structure Prediction, pp. 492-495, 1994.*
Skolnick et al. From genes to protein structure and function: novel applications of computational approaches in the genomic era. Trends Biotech 18(1): 34-39, 2000.*
Smith et al. The challenges of genome sequence annotation or "The devil is in the details". Nature Biotech 15: 1222-1223, 1997.*
Tokuriki et al. Stability effects of mutations and protein evolvability. Curr Opin Structural Biol 19: 596-604, 2009.*
Wells, J.A. Additivity of mutational effects in proteins. Biochemistry 29(37): 8509-8517, 1990.*
Zhang et al. FcgammaRII-binding centyrins mediate agonism and antibody-dependent cellular phagocytosis when fused to an anti-OX40 antibody. Mabs 10(3): 463-475, 2018.*
PCT International Search Report dated Nov. 8, 2018 for PCT/US2018/047843.
Alfthan, et al., "Properties of a single-chain antibody containing different linker peptides," Protein Engineering, 8(7): 725-731 (1995).
Amigorena, et al., "Cytoplkasmic Domain Heterogeneity and Functions of IgG Fc Receptors in B Lymphocytes," Science, 256: 1808-1812 (1992).
Bork, et al., "Proposed acquisition of an animal protein domain by bacteria," Proceedings of the National Academy of Science USA, 89: 8990-8994 (1992).
Cassel, et al., "Differential expression of Fcγ RIIA, Fcγ RIIB and Fcγ RIIc in hematopoietic cells: Analysis of transcripts," Molecular Immunology, 30(5): 451-460 (1993).
Chothia et al., "Canonical Structures for the Hypervariable Regions of Immunoglobulins," Journal of Molecular Biology, 126: 901-917 (1987).
Chu, et al., "Inhibition of B cell receptor-mediated activation of primary human B cell coengagement of CD19 and FcγRIIb with Fc-engineered antibodies," Molecular Immunology, 45: 3926-3933 (2008).
Hallewell, et al., "Genetically Engineered Polymers of Human CuZn Superoxide Dismutase," The Journal of Biological Chemistry, 264(9): 5260-5268 (1989).
Horton, et al., "Antibody-Mediated Coengagement of FcγRIIb and B Cell Receptor Complex Suppresses Humoral Immunity in Systemic Lupus Erythematosus," The Journal of Immunology, 186: 4223-4233 (2011).

Knappik et al., "Fully Synthetic Human Combinatorial Antibody Libraries (HuCAL) Based on Modular Consensus Frameworks and CDRs Randomized with Trinucleotides," The Journal of Molecular Biology, 296: 57-86 (2000).
Lefranc et al., "IMGT unique numbering for immunoglobulin and T cell receptor variable dominsand Ig superfamily V-like domains," Development & Comparative Immunology, 27: 55-77 (2003).
Lehman, et al., "Enginerering proteins for thermostability: the use of sequence alignments versus rational design and directed evoluation," Current Opinions in Biotechnology, 12, 371-375 (2001).
Meinke, et al., "Cellulose-Binding Polypeptides from *Cellulomonas fimi*: Endoglucanase D (CenD), a Family A β-1,4-Glucanase," Journal of Bacteriology, 175(7): 1910-1918 (1993).
Mimoto, et al., "Engineered antibody Fc variant with selectively enhanced FcγRIIIb binding over both FcγRIIa$^{R131}$ and FcγRIIa$^{H131}$," Protein Engineering, Design & Selection, 26(10): 589-598 (2013).
Muta, et al., "A 13-amino-acid motif in the cytoplasmic domain of FcγRIIB modulates B-cell receptor signalling," Nature 368: 70-73 (1994).
Odegrip, et al., "CIS display_In vitro selection of peptides from libraries of protein-DNA complexes," Proceedings of the National Academy of Science USA, 101(9): 2806-2810 (2004).
Olsen, et al., "Design, Expression, and Stability of a Diverse Protein Library Based on the Human Fibronectin Type III Domain," Protein Science, 16(3): 476-484 (2009).
Pincetic, et al., "Type I and type II Fc receptors regulate innate and adaptive immunity," Nature Immunology, 15(8): 707-716 (2014).
Robinson, et al., "Covalent Attachment of Arc Repressor Subunits by a Peptide Linker Enhances Affinity for Operator DNA," Biochemistry, 35: 109-116 (1996).
Shi et al., "*De Novo* Selection of High-Affinity Antibodies form Synthetic Fab Libraries Displayed on Phage as pIX Fusion Proteins," Journal of Molecular Biology, 397-385-396 (2010).
William R. Strohl, "Optimization of Fc-mediated effector functions of Monoclonal antobodies," Current Opinion in Biotechnology, 20:685-691 (2009).
Watanabe, et al., "Gene Cloning of Chitinase A1 from *Bacillus circulans* WL-12 Revealed Its Evolutionary Relationship to *Serratia* Chitinase and to the Type III Homology Units of Fibronectin," The Journal of Biological Chemistry, 265 (26): 15659-15665 (1990).
White, et al., "FcγRIIB controls the potency of agonistic anti-TNFR mAbs," Cancer Immunology Immunotherapy, 62:941-948 (2013).
Woyke, et al., "In Vitro activities and Postantifungal Effects of the Potent Dolastatin 10 Derivative Auristatin PHE," Antimicrobial Agents and Chemotherapy, 45(12): 3580-3584 (2001).
Wu et al., "An Analysis of the Sequences of the Variable Regions of Bence Jones Proteins and Myeloma Light Chains and their Implications for Antibody Complementary," Journal of Experimental Medicine, 132: 211-250 (1970).
Zhang, et al., "Fc Engineering Approaches to Enhance the Agonism and Effector Functions of an Anti-OX40 Antibody," Journal of Biological Chemistry, 291(53): 27134-27146 (2016).

* cited by examiner

```
            1                              30
R2BS6       LPAPKNLVVSRVTEDSARLSWTAPDAAFDS
R2BS9       LPAPKNLVVSRVTEDSARLSWTAPDAAFDS
R2BS12      LPAPKNLVVSRVTEDSARLSWTAPDAAFDS
R2BS26      LPAPKNLVVSRVTEDSARLSWTAPDAAFDS
R2BS29      LPAPKNLVVSRVTEDSARLSWTAPDAAFDS
R2BS39      LPAPKNLVVSRVTEDSARLSWTAPDAAFDS
R2BS56      LPAPKNLVVSRVTEDSARLSWTAPDAAFDS
            *****************************

31                             60
R2BS6       FLIQYQESEKVGEAIVLTVPGSERSYDLTG
R2BS9       FWIYYLEYWRGGEAIVLTVPGSERSYDLTG
R2BS12      FLIAYAEYWEGGEAVVLTVPGSERSYDLTG
R2BS26      FPIAYIEYWTGGEAIVLTVPGSERSYDLTG
R2BS29      FPIYYWEYRVGGEAIVLTVPGSERSYDLTG
R2BS39      FLIQYQESEKVGEAIVLTVPGSERSYDLTG
R2BS56      FSIAYWEYRKGGEAIVLTVPGSERSYDLTG
            *  *      ***:***************

61                             89
R2BS6       LKPGTEYTVSIYGVQYAAWYLPRHHEASNPLSAIFTT
R2BS9       LKPGTEYFVQIHGVKGGQY--------SYPLSAIFTT
R2BS12      LKPGTEYFVQINGVKGGFW--------SIPLSAIFTT
R2BS26      LKPGTEYFVWIHGVKGGAW--------SSPLSAIFTT
R2BS29      LKPGTEYFVYINGVKGGEE--------SRPLSAIFTT
R2BS39      LKPGTEYTVSIYGVSHGPWYN-YGEWRSNPLSAIFTT
R2BS56      LKPGTEYFVLIYGVKGGWQ--------SKPLSAIFTT
            ******* * * **. .         * *******
```

FC γ RIII BINDING FIBRONECTIN TYPE III DOMAINS, THEIR CONJUGATES AND MULTISPECIFIC MOLECULES COMPRISING THEM

CROSS-REFERENCE TO RELATED APPLICATIONS

This application claims the benefit of U.S. Provisional Application Ser. No. 62/550,152, filed 25 Aug. 2017. The entire content of the aforementioned application is incorporated herein by reference in its entirety.

SEQUENCE LISTING

This application contains a Sequence Listing submitted via EFS-Web, the entire content of which is incorporated herein by reference. The ASCII text file, created on 25 Jul. 2018, is named JBI5136USNP1SEQLIST.txt and is 119 kilobytes in size.

FIELD OF THE INVENTION

The present invention relates to FcγRII binding FN3 domains, their conjugates and multispecific molecules comprising them, isolated nucleotides encoding the molecules, vectors, host cells, and methods of making and using them.

BACKGROUND OF THE INVENTION

In humans, there are two general classes of Fc gamma receptors (FcγRs) for IgG class antibodies, activating receptors, characterized by the presence of a cytoplasmic immunoreceptor tyrosine-based activation motif (ITAM) sequence associated with the receptor, and the inhibitory receptor, characterized by the presence of an immunoreceptor tyrosine-based inhibitory motif (ITIM) sequence. Activating FcγRs which comprise FcγRI, FcγRIIA, FcγRIIIA and FcγRIIIB induce activating or pro-inflammatory responses, while inhibitory FcγRIIB induces anti-inflammatory or inhibitory responses. A key feature of the Fc gamma receptor (FcγR) system is the coexpression of the activating and inhibitory FcγR on the same cell, thereby setting thresholds for activation (Amigorena, Bonnerot et al. (1992) Science 256: 1808-1812, Muta, Kurosaki et al. (1994) Nature 368: 70-73, White, Chan et al. (2013) Cancer Immunol Immunother 62: 941-948, Pincetic, Bournazos et al. (2014) Nat Immunol 15: 707-716).

FcγRIIA and FcγRIIB are 96% identical in their extracellular domains. They are expressed on a variety of haemapoietic cells and are the only Fc-receptors on human platelets and megakaryocytes (Cassel, McKenzie, 1993). FcγRIIB is broadly expressed on all leukocytes except on T- and NK-cells and is the sole inhibitory Fc receptor expressed on human B cells. FcγRIIB ligation mediates inhibition of calcium-dependent processes such as degranulation, phagocytosis, ADCC, cytokine release and pro-inflammatory activation as well as B cell proliferation. FcγRIIA is expressed on monocytes, macrophages, dendritic cells, basophils and mast cells and mediates activation of these cells upon ligation. Blocking Ig binding to FcγRIIA and FcγRIIB may hence be used to suppress or enhance immune responses, respectively, and molecules blocking the interaction may be used in the treatment of a spectrum of diseases.

FcγRIIB, in addition to its general inhibitory function, was later identified to be required for agonistic activity of antibodies directed to TNFR superfamily members by mediating cross-linking of the antibodies and subsequent receptor clustering to initiate signaling [3, 8]. Efforts to further enhance the agonistic activity of the anti-TNFR superfamily member antibodies has included Fc engineering to enhance FcγRIIB binding, such as introducing S267E or V12 mutations in the Fc (Chu, Vostiar et al. (2008) Mol Immunol 45: 3926-3933, Horton, Chu et al. (2011) J Immunol 186: 4223-4233, Mimoto, Katada et al. (2013) Protein Eng Des Sel 26: 589-598, Zhang, Goldberg et al. (2016) J Biol Chem 291: 27134-27146)

SUMMARY OF THE INVENTION

The invention provides for an isolated FcγRII binding fibronectin type II (FN3) domain.

The invention also provides for an isolated FcγRII binding FN3 domain. comprising an amino acid sequence of SEQ ID NOs: 16, 17, 18, 19, 20, 21 or 22.

The invention also provides for an isolated FcγRII binding FN3 domain to a heterologous molecule.

The invention also provides for a polynucleotide comprising the polynucleotide sequence of SEQ ID NOs: 23, 24, 25, 26, 27, 28 or 29; or encoding the polypeptide of SEQ ID NOs: 16, 17, 18, 19, 20, 21 or 22.

The invention also provides for a polynucleotide comprising the polynucleotide sequence of SEQ ID NOs: 46, 47, 48, 49, 50, 51, 52, 53, 54, 55, 56, 57, 58 or 59; or encoding the polypeptide of SEQ ID NOs: 30, 31, 32, 33, 34, 35, 36, 37, 38, 39, 40, 41, 42 or 43.

The invention also provides for a vector comprising the polynucleotide of the invention.

The invention also provides for a host cell comprising the vector of the invention.

The invention also provides for a method of producing the isolated FN3 domain of the invention, comprising culturing the host cell of the invention under conditions that the FN3 domain is expressed, and purifying the FN3 domain.

The invention also provides for a pharmaceutical composition comprising the FN3 domain of the invention and a pharmaceutically acceptable carrier.

The invention also provides for an anti-idiotypic antibody that specifically binds the FN3 domain of the invention.

The invention also provides for a kit comprising the FN3 domain of the invention.

The invention also provides for a method of enhancing antibody dependent cellular phagocytosis (ADCP) activity of a polypeptide, comprising conjugating to the polypeptide a FcγRII binding FN3 domain and measuring enhanced ADCP activity of the polypeptide.

The invention also provides for a multispecific molecule comprising an anti-tumor necrosis factor receptor (TNFR) superfamily member antibody comprising a heavy chain and a light chain and a FcγRII binding FN3 domain.

The invention also provides for method of enhancing agonistic activity of an anti-TNFR superfamily member antibody, comprising conjugating the antibody to a FcγRIIB binding FN3 domain to generate an engineered anti-TNFR superfamily member antibody; and measuring the enhanced agonistic activity of the engineered anti-TNFR superfamily member antibody.

The invention also provides for a method of treating cancer in a subject, comprising administering a therapeutically effective amount of an isolated multispecific molecule comprising an anti-TNFR superfamily member antibody comprising a heavy chain and a light chain and a FcγRII binding FN3 domain to the subject to treat the cancer.

The invention also provides for an isolated multispecific molecule comprising an anti-TNFR superfamily member antibody comprising a heavy chain and a light chain and a FcγRII binding FN3 domain for use in the treatment of cancer.

The invention also provides for a use of an isolated multispecific molecule comprising an anti-TNFR superfamily member antibody comprising a heavy chain and a light chain and a FcγRII binding FN3 domain in the manufacture of a medicament for the treatment of cancer.

BRIEF DESCRIPTION OF THE DRAWINGS

FIG. 1 shows the alignment of FcγRII binding FN3 domains. Residue numbering is according to R2BS9 (SEQ ID NO: 17). R2BS6 (SEQ ID NO: 16), R2BS9 (SEQ ID NO: 17), R2BS12 (SEQ ID NO: 18), R2BS26 (SEQ ID NO: 19), R2BS29 (SEQ ID NO: 20), R2BS39 (SEQ ID NO: 21), R2BS56 (SEQ ID NO: 22). Boxed residues indicate the diversified regions C strand and CD loop (residues 29-43) and F strand and FG loop (residues 65-81).

DETAILED DESCRIPTION OF THE INVENTION

As used in this specification and the appended claims, the singular forms "a," "an," and "the" include plural referents unless the content clearly dictates otherwise. Thus, for example, reference to "a cell" includes a combination of two or more cells, and the like.

"Fibronectin type III (FN3) domain" (FN3 domain) refers to a domain occurring frequently in proteins including fibronectins, tenascin, intracellular cytoskeletal proteins, cytokine receptors and prokaryotic enzymes (Watanabe, Suzuki et al. (1990) *J Biol Chem* 265: 15659-15665, Bork and Doolittle (1992) *Proc Natl Acad Sci USA* 89: 8990-8994, Meinke, Gilkes et al. (1993) *J Bacteriol* 175: 1910-1918). Exemplary FN3 domains are the 15 different FN3 domains present in human tenascin C, the 15 different FN3 domains present in human fibronectin (FN), and non-natural synthetic FN3 domains as described for example in U.S. Pat. No. 8,278,419. Individual FN3 domains are referred to by domain number and protein name, e.g., the 3$^{rd}$ FN3 domain of tenascin (TN3), or the 10$^{th}$ FN3 domain of fibronectin (FN10).

"OX-40" refers to human OX40 (e.g. CD134 having the amino acid sequence of SEQ ID NO: 1.

"FcγRIIA" refers to human FcγRIIA having the amino acid sequence of SEQ ID NO: 2.

"FcγRIIB" human FcγRIIB having the amino acid sequence of SEQ ID NO: 3.

"FcγRII" refers to both FcγRIIA and FcγRIIB.

"Tencon" refers to the synthetic fibronectin type III (FN3) domain having the sequence of SEQ ID NO: 4 and described in U.S. Pat. Publ. No. US2010/0216708.

"Tencon27" refers to the synthetic FN3 domain having the sequence of SEQ ID NO: 5 and described in U.S. Pat. No. 9,200,273.

(OX40)
SEQ ID NO: 1
MCVGARRLGRGPCAALLLLGLGLSTVTGLHCVGDTYPSNDRCCHECRPGN

GMVSRCSRSQNTVCRPCGPGFYNDVVSSKPCKPCTWCNLRSGSERKQLCT

ATQDTVCRCRAGTQPLDSYKPGVDCAPCPPGHFSPGDNQACKPWTNCTLA

GKHTLQPASNSSDAICEDRDPPATQPQETQGPPARPITVQPTEAWPRTSQ

GPSTRPVEVPGGRAVAAILGLGLVLGLLGPLAILLALYLLRRDQRLPPDA

HKPPGGGSFRTPIQEEQADAHSTLAKI (FcγRIIA)
SEQ ID NO: 2
MTMETQMSQNVCPRNLWLLQPLTVLLLLASADSQAAPPKAVLKLEPPWIN

VLQEDSVTLTCQGARSPESDSIQWFHNGNLIPTHTQPSYRFKANNNDSGE

YTCQTGQTSLSDPVHLTVLSEWLVLQTPHLEFQEGETIMLRCHSWKDKPL

VKVTFFQNGKSQKFSHLDPTFSIPQANHSHSGDYHCTGNIGYTLFSSKPV

TITVQVPSMGSSSPMGIIVAVVIATAVAAIVAAVVALIYCRKKRISANST

DPVKAAQFEPPGRQMIAIRKRQLEETNNDYETADGGYMTLNPRAPTDDDK

NIYLTLPPNDHVNSNN (FcγRIIB)
SEQ ID NO: 3
MGILSFLPVLATESDWADCKSPQPWGHMLLWTAVLFLAPVAGTPAAPPKA

VLKLEPQWINVLQEDSVTLTCRGTHSPESDSIQWFHNGNLIPTHTQPSYR

FKANNNDSGEYTCQTGQTSLSDPVHLTVLSEWLVLQTPHLEFQEGETIVL

RCHSWKDKPLVKVTFFQNGKSKKFSRSDPNFSIPQANHSHSGDYHCTGNI

GYTLYSSKPVTITVQAPSSSPMGIIVAVVTGIAVAAIVAAVVALIYCRKK

RISALPGYPECREMGETLPEKPANPTNPDEADKVGAENTITYSLLMHPDA

LEEPDDQNRI (Tencon)
SEQ ID NO: 4
LPAPKNLVVSEVTEDSLRLSWTAPDAAFDSFLIQYQESEKVGEAINLTVP

GSERSYDLTGLKPGTEYTVSIYGVKGGHRSNPLSAEFTT (Tencon27)
SEQ ID NO: 5
LPAPKNLVVSRVTEDSARLSWTAPDAAFDSFLIQYQESEKVGEAIVLTVP

GSERSYDLTGLKPGTEYTVSIYGVKGGHRSNPLSAIFTT

"Centyrin" refers to a FN3 domain that is based on the consensus sequence of the 15 different FN3 domains present in human tenascin C.

"Antibodies" is meant in a broad sense and includes immunoglobulin molecules including monoclonal antibodies including murine, human, humanized and chimeric monoclonal antibodies, antibody fragments, bispecific or multispecific antibodies, dimeric, tetrameric or multimeric antibodies, single chain antibodies, domain antibodies and any other modified configuration of the immunoglobulin molecule that comprises an antigen binding site of the required specificity. "Full length antibody molecules" are comprised of two heavy chains (HC) and two light chains (LC) inter-connected by disulfide bonds as well as multimers thereof (e.g. IgM). Each heavy chain is comprised of a heavy chain variable region (VH) and a heavy chain constant region (comprised of domains CH1, hinge, CH2 and CH3). Each light chain is comprised of a light chain variable region (VL) and a light chain constant region (CL). The VH and the VL regions may be further subdivided into regions of hyper variability, termed complementarity determining regions (CDR), interspersed with framework regions (FR). Each VH and VL is composed of three CDRs and four FR segments, arranged from amino-to-carboxyl-terminus in the following order: FR1, CDR1, FR2, CDR2, FR3, CDR3 and FR4.

"Complementarity determining regions (CDR)" are "antigen binding sites" in an antibody. CDRs may be defined using various terms: (i) Complementarity Determining Regions (CDRs), three in the VH (HCDR1, HCDR2, HCDR3) and three in the VL (LCDR1, LCDR2, LCDR3) are based on sequence variability (Wu et al. (1970) *J Exp Med* 132: 211-50) (Kabat et al., Sequences of Proteins of Immunological Interest, 5th Ed. Public Health Service, National Institutes of Health, Bethesda, Md., 1991). (ii) "Hypervariable regions", "HVR", or "HV", three in the VH (H1, H2, H3) and three in the VL (L1, L2, L3) refer to the regions of an antibody variable domains which are hypervariable in structure as defined by Chothia and Lesk (Chothia et al. (1987) *J Mol Biol* 196: 901-17). The International ImMunoGeneTics (IMGT) database (http://www_imgt_org) provides a standardized numbering and definition of antigen-binding sites. The correspondence between CDRs, HVs and IMGT delineations is described in (Lefranc et al. (2003) *Dev Comp Immunol* 27: 55-77). The term "CDR", "HCDR1", "HCDR2", "HCDR3", "LCDR1", "LCDR2" and "LCDR3" as used herein includes CDRs defined by any of the methods described supra, Kabat, Chothia or IMGT, unless otherwise explicitly stated in the specification.

Immunoglobulins may be assigned to five major classes, IgA, IgD, IgE, IgG and IgM, depending on the heavy chain constant region amino acid sequence. IgA and IgG are further sub-classified as the isotypes IgA1, IgA2, IgG1, IgG2, IgG3 and IgG4. Antibody light chains of any vertebrate species may be assigned to one of two clearly distinct types, namely kappa (κ) and lambda (λ), based on the amino acid sequences of their constant regions.

"Antibody fragments" refers to a portion of an immunoglobulin molecule that retains the heavy chain and/or the light chain antigen binding site, such as heavy chain complementarity determining regions (HCDR) 1, 2 and 3, light chain complementarity determining regions (LCDR) 1, 2 and 3, a heavy chain variable region (VH), or a light chain variable region (VL). Antibody fragments include well known Fab, F(ab')2, Fd and Fv fragments as well as domain antibodies (dAb) consisting of one VH domain or one VL domain. VH and VL domains may be linked together via a synthetic linker to form various types of single chain antibody designs where the VH/VL domains may pair intramolecularly, or intermolecularly in those cases when the VH and VL domains are expressed by separate single chain antibody constructs, to form a monovalent antigen binding site, such as single chain Fv (scFv) or diabody; described for example in Int. Patent Publ. Nos. WO1998/44001, WO1988/01649, WO1994/13804 and WO1992/01047.

"Monoclonal antibody" refers to an antibody population with single amino acid composition in each heavy and each light chain, except for possible well known alterations such as removal of C-terminal lysine from the antibody heavy chain or alterations due to post-translational modification(s) of amino acids, such as methionine oxidation or asparagine or glutamine deamidation. Monoclonal antibodies typically specifically bind one antigenic epitope, except that bispecific or multispecific monoclonal antibodies specifically bind two or more distinct antigenic epitopes. Monoclonal antibodies may have heterogeneous glycosylation within the antibody population. Monoclonal antibody may be monospecific or multispecific, or monovalent, bivalent or multivalent. A bispecific antibody is included in the term monoclonal antibody.

"Humanized antibody" refers to an antibody in which the antigen binding sites are derived from non-human species and the variable region frameworks are derived from human immunoglobulin sequences. Humanized antibody may include substitutions in the framework so that the framework may not be an exact copy of expressed human immunoglobulin or human immunoglobulin germline gene sequences.

"Human antibody" refers to an antibody having heavy and light chain variable regions in which both the framework and the antigen binding site are derived from sequences of human origin and is optimized to have minimal immune response when administered to a human subject. If the antibody contains a constant region or a portion of the constant region, the constant region also is derived from sequences of human origin.

Human antibody comprises heavy or light chain variable regions that are "derived from" sequences of human origin if the variable regions of the antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci as described herein. "Human antibody" may contain amino acid differences when compared to the human germline immunoglobulin or rearranged immunoglobulin genes due to differences between the systems used to obtain the antibody and human immunoglobulin loci, introduction of somatic mutations or intentional introduction of substitutions into the framework or antigen binding site, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin or rearranged immunoglobulin genes. In some cases, "human antibody" may contain consensus framework sequences derived from human framework sequence analyses, for example as described in (Knappik et al. (2000) *J Mol Biol* 296: 57-86), or synthetic HCDR3 incorporated into human immunoglobulin gene libraries displayed on phage, for example as described in (Shi et al. (2010) *J Mol Biol* 397: 385-96), and in Int. Patent Publ. No. WO2009/085462.

Human antibodies derived from human immunoglobulin sequences may be generated using systems such as phage display incorporating synthetic CDRs and/or synthetic frameworks, or may be subjected to in vitro mutagenesis to improve antibody properties, resulting in antibodies that are not expressed by the human antibody germline repertoire in vivo.

Antibodies in which antigen binding sites are derived from a non-human species are not included in the definition of "human antibody".

"Anti-tumor necrosis factor receptor (TNFR) superfamily member antibody" or anti-TNFR superfamily member antibody refers to an antibody that specifically binds a TNFR superfamily member. Exemplary TNFR superfamily members are tumor necrosis factor receptor 1 (CD120a), tumor necrosis factor receptor 2 (CD120b), lymphotoxin beta receptor (CD18), OX40 (CD134), CD40, Fas receptor (CD95), Decoy receptor 3 (TR6), CD27, CD30, 4-1BB (CD137), Death receptor 4 (TRAILR1), Death receptor 5 (TRAILR2), Decoy receptor 1 (TRAILR3), Decoy receptor 2 (TRAILR4), RANK (CD265), Osteoprotegerin, TWEAK receptor, TACI (CD267), BAFF receptor (CD268), Herpesvirus entry mediator (CD270), Nerve growth factor receptor (CD271), B-cell maturation antigen (CD269), Glucocorticoid-induced TNFR-related (CD357), TROY (TRADE), Death receptor 6 (CD358), Death receptor 3 (Apo-3) and Ectodysplasin A2 receptor (XEDAR).

"Binds", "binding", "specifically binds" or "specific binding" refers to the ability of the molecule of the invention (such as an FN3 domain) to bind a specific antigen (such as FcγRII) with a dissociation constant ($K_D$) of about $1 \times 10^{-6}$ M or less, for example about $1 \times 10^{-7}$ M or less, about $1 \times 10^{-8}$ M or less, about $1 \times 10^{-9}$ M or less, about $1 \times 10^{-10}$ M or less, about $1 \times 10^{-11}$ M or less, about $1 \times 10^{-12}$ M or less, or about $1 \times 10^{-13}$ M or less. Alternatively, "binds" refers to the ability of the molecule of the invention to bind the specific antigen at least 5-fold above the negative control in standard ELISA assay. The isolated molecule of the invention that binds FcγRII may, however, have cross-reactivity to other related antigens, for example to the same predetermined antigen from other species (homologs), such as *Macaca Fascicularis* (cynomolgous monkey, cyno) or *Pan troglodytes* (chimpanzee).

"Multispecific" refers to a molecule that binds two or more distinct antigens or two or more distinct epitopes within the same antigen.

"Bispecific" refers to a molecule that binds two distinct antigens or two distinct epitopes within the same antigen. The bispecific molecule may have cross-reactivity to other related antigens, for example to the same antigen from other species (homologs), such as human or monkey, for example *Macaca fascicularis* (cynomolgus, cyno), *Pan troglodytes* (chimpanzee, chimp) or *Callithrix jacchus* (common marmoset, marmoset), or may bind an epitope that is shared between two or more distinct antigens.

"Recombinant" refers to antibodies and other proteins that are prepared, expressed, created or isolated by recombinant means.

"Isolated" refers to a homogenous population of molecules (such as synthetic polynucleotides or a polypeptide such as FN3 domains) which have been substantially separated and/or purified away from other components of the system the molecules are produced in, such as a recombinant cell, as well as a protein that has been subjected to at least one purification or isolation step. "Isolated FN3 domain" refers to an FN3 domain that is substantially free of other cellular material and/or chemicals and encompasses FN3 domains that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"Vector" refers to a polynucleotide capable of being duplicated within a biological system or that can be moved between such systems. Vector polynucleotides typically contain elements, such as origins of replication, polyadenylation signal or selection markers that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

"Expression vector" refers to a vector that can be utilized in a biological system or in a reconstituted biological system to direct the translation of a polypeptide encoded by a polynucleotide sequence present in the expression vector.

"Polynucleotide" refers to a synthetic molecule comprising a chain of nucleotides covalently linked by a sugar-phosphate backbone or other equivalent covalent chemistry. cDNA is a typical example of a polynucleotide.

"Polypeptide" or "protein" refers to a molecule that comprises at least two amino acid residues linked by a peptide bond to form a polypeptide Small polypeptides of less than about 50 amino acids may be referred to as "peptides".

"Sample" refers to a collection of similar fluids, cells, or tissues isolated from a subject, as well as fluids, cells, or tissues present within a subject. Exemplary samples are tissue biopsies, fine needle aspirations, surgically resected tissue, organ cultures, cell cultures and biological fluids such as blood, serum and serosal fluids, plasma, lymph, urine, saliva, cystic fluid, tear drops, feces, sputum, mucosal secretions of the secretory tissues and organs, vaginal secretions, ascites fluids, fluids of the pleural, pericardial, peritoneal, abdominal and other body cavities, fluids collected by bronchial lavage, synovial fluid, liquid solutions contacted with a subject or biological source, for example, cell and organ culture medium including cell or organ conditioned medium and lavage fluids and the like.

"Subject" includes any human or nonhuman animal "Nonhuman animal" includes all vertebrates, e.g., mammals and non-mammals, such as nonhuman primates, sheep, dogs, cats, horses, cows, chickens, amphibians, reptiles, etc. Except when noted, the terms "patient" or "subject" are used interchangeably.

"Agonist" refers to a molecule that induces at least one biological activity of the TNFR superfamily member the molecule binds to that is induced by a natural ligand of the TNFR superfamily member. Exemplary agonistic activities include induction of production of a secreted embryonic alkaline phosphatase (SEAP) expressed under the control of NFκB-inducible promoter in an in vitro assay, induction of dendritic cell (DC) differentiation assessed by increased CD80, CD83, CD86 and HLA-DR surface expression on DC, activation of B cells assessed by increased B cell proliferation or increased CD23, CD80, CD83, CD86 and HLA-DR surface expression on B cells, induction of antigen-specific T cell recall responses assessed by production of interferon-γ (IFN-γ) by PBMCs isolated from patients previously exposed to the antigen, and induction of proliferation of activated T cells or IFN-γ or TNF-α production by activated T cells. Agonistic activity (e.g., agonism) may be cross-linking dependent or independent of antibody cross-linking.

"Enhanced agonistic activity" or "enhanced agonism" refers to improvement in agonism of a test molecule when compared to a reference molecule or a negative control. "Enhanced" may be an enhancement of about 10%, 20%, 30%, 40%, 50%, 60%, 70%, 80%, 90%, 100% or more, or a statistically significant enhancement mediated by the test molecule when compared to a negative control.

"Cross-linking" refers to the higher order multimerization of an anti-TNFR superfamily member antibody on cells expressing the TNFR superfamily member, induced by the antibody binding to FcγR, for example FcγRIIB cis or trans, and subsequent induction of TNFR agonistic activity. Cross-linking may be evaluated in vitro by using anti-human F(ab')2 as a cross-linker, or cells expressing FcγRIIB, such as Raji cells.

"Agonistic activity independent of antibody cross-linking" means that the antibody displays agonistic activity in solution in the absence of a cross-linker, such as Raji cells expressing FcγR, for example FcγRIIB.

The numbering of amino acid residues in the antibody constant region throughout the specification is according to the EU index as described in Kabat et al., Sequences of Proteins of Immunological Interest, 5th Ed. Public Health Service, National Institutes of Health, Bethesda, Md. (1991), unless otherwise explicitly stated.

Conventional one and three-letter amino acid codes are used herein as shown in Table 1.

TABLE 1

| Amino acid | Three-letter code | One-letter code |
|---|---|---|
| Alanine | Ala | A |
| Arginine | Arg | R |
| Asparagine | Asn | N |
| Aspartate | Asp | D |
| Cysteine | Cys | C |
| Glutamate | Gln | E |
| Glutamine | Glu | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Compositions of Matter

The invention provides for FcγRII binding FN3 domains and their fusion proteins. The FN3 domains are useful for example as imaging agents and/or as therapeutic agents.

Isolation of FcγRII binding FN3 domains from a library based on Tencon sequence

Tencon (SEQ ID NO: 4) is a non-naturally occurring fibronectin type III (FN3) domain designed from a consensus sequence of fifteen FN3 domains from human tenascin-C (U.S. Pat. Publ. No. 2010/0216708). The crystal structure of Tencon shows six surface-exposed loops that connect seven beta-strands as is characteristic to the FN3 domains, the beta-strands referred to as A, B, C, D, E, F, and G, and the loops referred to as AB, BC, CD, DE, EF, and FG loops (Bork and Doolittle (1992) *Proc Natl Acad Sci USA* 89: 8990-8994). These loops, or selected residues within each loop, may be randomized to construct libraries of fibronectin type III (FN3) domains that may be used to select novel molecules that bind FcγRII. Table 2 shows positions and sequences of each loop and beta-strand in Tencon (SEQ ID NO: 4). Library designed based on Tencon sequence may thus have randomized FG loop, or randomized BC and FG loops. Tencon BC loop is 7 amino acids long, thus 1, 2, 3, 4, 5, 6 or 7 amino acids may be randomized in the library diversified at the BC loop and designed based on Tencon sequence. Tencon FG loop is 7 amino acids long, thus 1, 2, 3, 4, 5, 6 or 7 amino acids may be randomized in the library diversified at the FG loop and designed based on Tencon sequence. Further diversity at loops in the Tencon libraries may be achieved by insertion and/or deletions of residues at loops. For example, the FG and/or BC loops may be extended by 1-22 amino acids, or decreased by 1-3 amino acids. The FG loop in Tencon is 7 amino acids long, whereas the corresponding loop in antibody heavy chains ranges from 4-28 residues. To provide maximum diversity, the FG loop may be diversified in sequence as well as in length to correspond to the antibody CDR3 length range of 4-28 residues. For example, the FG loop can further be diversified in length by extending the loop by additional 1, 2, 3, 4 or 5 amino acids. Library designed based on Tencon sequence may also have randomized alternative surfaces that form on a side of the FN3 domain and comprise two or more beta strands, and at least one loop. One such alternative surface is formed by amino acids in the C and the F beta-strands and the CD and the FG loops (a C-CD-F-FG surface). A library design based on Tencon alternative C-CD-F-FG surface is described in U.S. Pat. Publ. No. US2013/0226834. Library designed based on Tencon sequence also includes libraries designed based on Tencon variants, such as Tencon variants having substitutions at residues positions 11, 14, 17, 37, 46, 73, or 86 (residue numbering corresponding to SEQ ID NO: 4), and which variants display improve thermal stability. Exemplary Tencon variants are described in US Pat. Publ. No. 2011/0274623, and include Tencon27 (SEQ ID NO: 5) having substitutions E11R, L17A, N46V and E86I when compared to Tencon of SEQ ID NO: 4.

TABLE 2

| FN3 domain | Tencon (SEQ ID NO: 4) |
|---|---|
| A strand | 1-12 |
| AB loop | 13-16 |
| B strand | 17-21 |
| BC loop | 22-28 |
| C strand | 29-37 |
| CD loop | 38-43 |
| D strand | 44-50 |
| DE loop | 51-54 |
| E strand | 55-59 |
| EF loop | 60-64 |
| F strand | 65-74 |
| FG loop | 75-81 |
| G strand | 82-89 |

Tencon based libraries may be randomized at chosen residue positions using a random or defined set of amino acids. For example, variants in the library having random substitutions may be generated using NNK codons, which encode all 20 naturally occurring amino acids. In other diversification schemes, DVK codons may be used to encode amino acids Ala, Trp, Tyr, Lys, Thr, Asn, Lys, Ser, Arg, Asp, Glu, Gly, and Cys. Alternatively, NNS codons may be used to give rise to all 20 amino acid residues and simultaneously reducing the frequency of stop codons. Libraries of FN3 domains with biased amino acid distribution at positions to be diversified may be synthesized for example using Slonomics® technology (http:_//www_sloning_com). This technology uses a library of pre-made double stranded triplets that act as universal building blocks sufficient for thousands of gene synthesis processes. The triplet library represents all possible sequence combinations necessary to build any desired DNA molecule. The codon designations are according to the well-known IUB code.

FcγRII binding FN3 domains of the invention may be isolated by producing the FN3 library such as the Tencon library using cis display to ligate DNA fragments encoding the scaffold proteins to a DNA fragment encoding RepA to generate a pool of protein-DNA complexes formed after in vitro translation wherein each protein is stably associated with the DNA that encodes it (U.S. Pat. No. 7,842,476; Odegrip, Coomber et al. (2004) *Proc Natl Acad Sci USA* 101: 2806-2810), and assaying the library for binding to FcγRII by any method known in the art and described in the Example. Exemplary well known methods which can be used are ELISA, sandwich immunoassays, and competitive and non-competitive assays. The identified FcγRII binding FN3 domains can be further evaluated for their desired characteristics.

FcγRII Binding FN3 Domains

The invention provides for an isolated FcγRII binding FN3 domain. In some embodiments, the isolated FN3 domain is based on Tencon amino acid sequence of SEQ ID NO: 4 or Tencon27 amino acid sequence of SEQ ID NO: 5, SEQ ID NO: 4 or SEQ ID NO: 5 optionally having substitutions at residues positions 11, 14, 17, 37, 46, 73, and/or 86.

The invention also provides for an isolated FcγRII binding FN3 domain comprising an amino acid sequence of SEQ ID NO: 16. In some embodiments, the FcγRII binding FN3 domain is encoded by a polynucleotide sequence of SEQ ID NO: 23.

The invention also provides for an isolated FcγRII binding FN3 domain comprising an amino acid sequence of SEQ ID NO: 17. In some embodiments, the FcγRII binding FN3 domain is encoded by a polynucleotide sequence of SEQ ID NO: 24.

The invention also provides for an isolated FcγRII binding FN3 domain comprising an amino acid sequence of SEQ ID NO: 18. In some embodiments, the FcγRII binding FN3 domain is encoded by a polynucleotide sequence of SEQ ID NO: 25.

The invention also provides for an isolated FcγRII binding FN3 domain comprising an amino acid sequence of SEQ ID NO: 19. In some embodiments, the FcγRII binding FN3 domain is encoded by a polynucleotide sequence of SEQ ID NO: 26.

The invention also provides for an isolated FcγRII binding FN3 domain comprising an amino acid sequence of SEQ ID NO: 20. In some embodiments, the FcγRII binding FN3 domain is encoded by a polynucleotide sequence of SEQ ID NO: 27.

The invention also provides for an isolated FcγRII binding FN3 domain comprising an amino acid sequence of SEQ ID NO: 21. In some embodiments, the FcγRII binding FN3 domain is encoded by a polynucleotide sequence of SEQ ID NO: 28.

The invention also provides for an isolated FcγRII binding FN3 domain comprising an amino acid sequence of SEQ ID NO: 22. In some embodiments, the FcγRII binding FN3 domain is encoded by a polynucleotide sequence of SEQ ID NO: 29.

The FcγRII binding FN3 domains of the invention may be modified to improve their properties such as improve thermal stability and reversibility of thermal folding and unfolding. Several methods have been applied to increase the apparent thermal stability of proteins and enzymes, including rational design based on comparison to highly similar thermostable sequences, design of stabilizing disulfide bridges, mutations to increase alpha-helix propensity, engineering of salt bridges, alteration of the surface charge of the protein, directed evolution, and composition of consensus sequences (Lehmann and Wyss, Curr Opin Biotechnol, 12, 371-375, 2001). High thermal stability may increase the yield of the expressed protein, improve solubility or activity, decrease immunogenicity, and minimize the need of a cold chain in manufacturing. Residues that may be substituted to improve thermal stability of Tencon (SEQ ID NO: 4) are residue positions 11, 14, 17, 37, 46, 73, and/or 86, and are described in US Pat. Publ. No. 2011/0274623. Substitutions corresponding to these residues may be incorporated to the FcγRII binding FN3 domains of the invention.

Measurement of protein stability and protein lability can be viewed as the same or different aspects of protein integrity. Proteins are sensitive or "labile" to denaturation caused by heat, by ultraviolet or ionizing radiation, changes in the ambient osmolarity and pH if in liquid solution, mechanical shear force imposed by small pore-size filtration, ultraviolet radiation, ionizing radiation, such as by gamma irradiation, chemical or heat dehydration, or any other action or force that may cause protein structure disruption. The stability of the molecule can be determined using standard methods. For example, the stability of a molecule can be determined by measuring the thermal melting ("$T_m$") temperature, the temperature in ° Celsius (° C.) at which half of the molecules become unfolded, using standard methods. Typically, the higher the $T_m$, the more stable the molecule. In addition to heat, the chemical environment also changes the ability of the protein to maintain a particular three-dimensional structure.

Chemical denaturation can likewise be measured by a variety of methods. Chemical denaturants include guanidinium hydrochloride, guanidinium thiocyanate, urea, acetone, organic solvents (DMF, benzene, acetonitrile), salts (ammonium sulfate, lithium bromide, lithium chloride, sodium bromide, calcium chloride, sodium chloride); reducing agents (e.g. dithiothreitol, beta-mercaptoethanol, dinitrothiobenzene, and hydrides, such as sodium borohydride), non-ionic and ionic detergents, acids (e.g. hydrochloric acid (HCl), acetic acid ($CH_3COOH$), halogenated acetic acids), hydrophobic molecules (e.g. phosopholipids), and targeted denaturants. Quantitation of the extent of denaturation can rely on loss of a functional property, such as ability to bind a target molecule, or by physiochemical properties, such as tendency to aggregation, exposure of formerly solvent inaccessible residues, or disruption or formation of disulfide bonds.

The FcγRII binding FN3 domains of the invention may be generated as monomers, dimers, or multimers, for example, to increase the valency and thus the avidity of target molecule binding, or to generate bi- or multispecific scaffolds simultaneously binding two or more different target molecules. The dimers and multimers may be generated by linking monospecific, bi- or multispecific protein scaffolds, for example, by the inclusion of an amino acid linker, for example a linker containing poly-glycine, glycine and serine, or alanine and proline. Exemplary linker include GSGS, (SEQ ID NO: 6), GGGSGGGS (SEQ ID NO: 7), GGGGSGGGGSGGGGSGGGGSGGGGS (SEQ ID NO: 8), APAP (SEQ ID NO: 9), APAPAPAPAP (SEQ ID NO: 10), APAPAPAPAPAPAPAPAPAP (SEQ ID NO: 11), APAPAPAPAPAPAPAPAPAPAPAPAPAPAPAP (SEQ ID NO: 12), AEAAAKEAAAKEAAAKEAAAKEA AAK AAA (SEQ ID NO: 13) and GGGGGSGGGGSGG GGSGGGGS (SEQ ID NO: 14). The dimers and multimers may be linked to each other in a N- to C-direction. The use of naturally occurring as well as artificial peptide linkers to connect polypeptides into novel linked fusion polypeptides is well known in the literature (Hallewell, Laria et al. (1989) *J Biol Chem* 264: 5260-5268, Alfthan, Takkinen et al. (1995) *Protein Eng* 8: 725-731, Robinson and Sauer (1996) *Biochemistry* 35: 109-116; U.S. Pat. No. 5,856,456).

FcγRII Binding FN3 Domain Conjugates

The invention also provides FcγRII binding FN3 domain conjugated to a heterologous molecule. In some embodiments, the FcγRII binding FN3 domain is conjugated to a polypeptide. In some embodiments, the FcγRII binding FN3 domain is conjugated to an antibody. In some embodiments, the FcγRII binding FN3 domain is conjugated to a half-life extending moiety. In some embodiments, the FcγRII binding FN3 domain is conjugated to a detectable label. In some embodiments, the FcγRII binding FN3 domain is conjugated to a cytotoxic drug. Conjugation may be via a peptide bond with the FN3 domain and may be generated by standard cloning and expression techniques. Alternatively, well known chemical coupling methods may be used to attach the moieties to recombinantly produced FN3 domains of the invention. FcγRII binding FN3 domains of the invention conjugated to heterologous molecules may be compared for functionality by several well-known assays. For example, altered properties due to incorporation of Fc domains and/or Fc domain variants may be assayed in Fc receptor binding assays using soluble forms of the receptors, such as the FcγRI, FcγRII, FcγRIII or FcRn receptors, or using well known cell-based assays measuring for example ADCC or CDC, or evaluating pharmacokinetic properties of the molecules of the invention in in vivo models.

Half-Life Extending Moieties

Exemplary half-life extending moieties are albumin, albumin variants, albumin-binding proteins and/or domains, transferrin and fragments and analogues thereof, and Fc regions. An exemplary albumin variant is shown in SEQ ID NO: 15 Amino acid sequences of the human Fc regions are well known, and include IgG1, IgG2, IgG3, IgG4, IgM, IgA and IgE Fc regions.

```
                                             SEQ ID NO: 15
DAHKSEVAHRFKDLGEENFKALVLIAFAQYLQQCPFEDHVKLVNEVTEFA

KTCVADESAENCDKSLHTLFGDKLCTVATLRETYGEMADCCAKQEPERN

ECFLQHKDDNPNLPRLVRPEVDVMCTAFHDNEETFLKKYLYEIARRHPYF

YAPELLFFAKRYKAAFTECCQAADKAACLLPKLDELRDEGKASSAKQRLK

CASLQKFGERAFKAWAVARLSQRFPKAEFAEVSKLVTDLTKVHTECCHG

DLLECADDRADLAKYICENQDSISSKLKECCEKPLLEKSHCIAEVENDEMP

ADLPSLAADFVESKDVCKNYAEAKDVFLGMFLYEYARRHPDYSVVLLLR

LAKTYETTLEKCCAAADPHECYAKVFDEFKPLVEEPQNLIKQNCELFEQLG

EYKFQNALLVRYTKKVPQVSTPTLVEVSRNLGKVGSKCCKHPEAKRMPC

AEDYLSVVLNQLCVLHEKTPVSDRVTKCCTESLVNRRPCFSALEVDETYV

PKEFNAETFTFHADICTLSEKERQIKKQTALVELVKHKPKATKEQLKAVM

DDFAAFVEKCCKADDKETCFAEEGKKLVAASQAALGL
```

All or a portion of an antibody constant region may be attached to the FcγRII binding FN3 domain of the invention to extend half-life and also impart antibody-like properties, especially those properties associated with the Fc region, such as Fc effector functions such as C1q binding, complement dependent cytotoxicity (CDC), Fc receptor binding, antibody-dependent cell-mediated cytotoxicity (ADCC), phagocytosis, down regulation of cell surface receptors (e.g., B cell receptor; BCR), and may be further modified by modifying residues in the Fc responsible for these activities (for review; see (Strohl (2009) *Curr Opin Biotechnol* 20: 685-691).

Other half-life extending moieties may be incorporated into the FcγRII binding FN3 domains of the invention are polyethylene glycol (PEG) molecules, such as PEG5000 or PEG20,000, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties.

A pegyl moiety may for example be added to the FcγRII binding FN3 domain of the invention by incorporating a cysteine residue to the C-terminus of the molecule, or engineering cysteines into residue positions that face away from the FcγRII binding face of the molecule, and attaching a pegyl group to the cysteine using well known methods.

Detectable Labels

The FcγRII binding FN3 domains of the invention conjugated to a detectable label may be used for example to evaluate expression of FcγRII on tissue or cell samples such as samples from a subject, or in in vivo imaging to detect FcγRII expressing cells, such as lymphocytes, in a subject.

Detectable label includes compositions that when conjugated to the FcγRII binding FN3 domains of the invention renders the FN3 domains detectable, via spectroscopic, photochemical, biochemical, immunochemical, or chemical means.

Exemplary detectable labels include radioactive isotopes, magnetic beads, metallic beads, colloidal particles, fluorescent dyes, electron-dense reagents, enzymes (for example, as commonly used in an ELISA), biotin, digoxigenin, haptens, luminescent molecules, chemilumine scent molecules, fluorochromes, fluorophores, fluorescent quenching agents, colored molecules, radioactive isotopes, cintillants, avidin, streptavidin, protein A, protein G, antibodies or fragments thereof, polyhistidine, Flag tags, myc tags, heavy metals, enzymes, alkaline phosphatase, peroxidase, luciferase, electron donors/acceptors, acridinium esters, and colorimetric substrates.

A detectable label may emit a signal spontaneously, such as when the detectable label is a radioactive isotope. The detectable label may also emit a signal because of being stimulated by an external field.

Exemplary radioactive isotopes may be γ-emitting, Auger-emitting, β-emitting, an alpha-emitting or positron-emitting radioactive isotope. Exemplary radioactive isotopes include $^3H$, $^{11}C$, $^{13}C$, $^{15}N$, $^{18}F$, $^{19}F$, $^{55}CO$, $^{57}Co$, $^{60}Co$, $^{61}Cu$, $^{62}Cu$, $^{64}Cu$, $^{67}Cu$, $^{68}Ga$, $^{72}As$, $^{75}Br$, $^{86}Y$, $^{89}Zr$, $^{90}Sr$, $^{94m}Tc$, $^{99m}Tc$, $^{99m}Tc$, $^{115}In$, $^{123}I$, $^{124}I$, $^{125}I$, $^{131}I$, $^{211}At$, $^{212}Bi$, $^{213}Bi$, $^{223}Ra$, $^{226}Ra$, $^{225}Ac$ and $^{227}AC$.

Exemplary metal atoms are metals with an atomic number greater than 20, such as calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, lead atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, *neptunium* atoms, plutonium atoms, americium atoms, curium atoms, berkelium atoms, californium atoms, einsteinium atoms, fermium atoms, mendelevium atoms, nobelium atoms, or lawrencium atoms.

In some embodiments, the metal atoms may be alkaline earth metals with an atomic number greater than twenty.

In some embodiments, the metal atoms may be lanthanides.

In some embodiments, the metal atoms may be actinides.

In some embodiments, the metal atoms may be transition metals.

In some embodiments, the metal atoms may be poor metals.

In some embodiments, the metal atoms may be gold atoms, bismuth atoms, tantalum atoms, and gadolinium atoms.

In some embodiments, the metal atoms may be metals with an atomic number of 53 (i.e. iodine) to 83 (i.e. bismuth).

In some embodiments, the metal atoms may be atoms suitable for magnetic resonance imaging.

The metal atoms may be metal ions in the form of +1, +2, or +3 oxidation states, such as $Ba^{2+}$, $Bi^{3+}$, $Cs^+$, $Ca^{2+}$, $Cr^{2+}$, $Cr^{3+}$, $Cr^{6+}$, $Co^{2+}$, $Co^{3+}$, $Cu^+$, $Cu^{2+}$, $Cu^{3+}$, $Ga^{3+}$, $Gd^{3+}$, $Au^+$, $Au^{3+}$, $Fe^{2+}$, $Fe^{3+}$, $F^{3+}$, $Pb^{2+}$, $Mn^{2+}$, $Mn^{3+}$, $Mn^{4+}$, $Mn^{7+}$, $Hg^{2+}$, $Ni^{2+}$, $Ni^{3+}$, $Ag^+$, $Sr^{2+}$, $Sn^{2+}$, $Sn^{4+}$, and $Zn^{2+}$. The metal atoms may comprise a metal oxide, such as iron oxide, manganese oxide, or gadolinium oxide.

Suitable dyes include any commercially available dyes such as, for example, 5(6)-carboxyfluorescein, IRDye 680RD maleimide or IRDye 800CW, ruthenium polypyridyl dyes, and the like.

Suitable fluorophores are fluorescein isothiocyante (FITC), fluorescein thiosemicarbazide, rhodamine, Texas Red, CyDyes (e.g., Cy3, Cys, Cy5.5), Alexa Fluors (e.g., Alexa488, Alexa555, Alexa594; Alexa647), near infrared (NIR) (700-900 nm) fluorescent dyes, and carbocyanine and aminostyryl dyes.

The invention also provides for a method of detecting FcγRII expressing cells in a subject, comprising
  conjugating the FcγRII binding FN3 domain comprising the amino acid sequence of SEQ ID NOs: 16, 17, 18, 19, 20, 21 or 22 to a detectable label to form a conjugate;
  administering the conjugate to a subject; and
  visualizing the FcγRII expressing cells to which the conjugate is bound.

The invention also provides for a method of detecting FcγRII expressing cells in a sample; comprising
  obtaining the sample;
  contacting the sample with the FcγRII binding FN3 domain comprising the amino acid sequence of SEQ ID NOs: 16, 17, 18, 19, 20, 21 or 22; and
  detecting binding of the FcγRII binding FN3 domain.

Cytotoxic Agents

The FcγRII binding FN3 domains of the invention conjugated to a cytotoxic agent may be used for example in the targeted delivery of the cytotoxic agent to FcγRII expressing cells, and intracellular accumulation therein, wherein systemic administration of these unconjugated cytotoxic agents may result in unacceptable levels of toxicity to normal cells.

In some embodiments, the cytotoxic agent is daunomycin, doxorubicin, methotrexate, vindesine, bacterial toxins such as diphtheria toxin, ricin, geldanamycin, maytansinoids or calicheamicin. The cytotoxic agent may elicit their cytotoxic and cytostatic effects by mechanisms including tubulin binding, DNA binding, or topoisomerase inhibition.

In some embodiments, the cytotoxic agent is an enzymatically active toxins such as diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In some embodiments, the cytotoxic agent is a radionuclide, such as $^{212}Bi$, $^{131}I$, $^{131}In$, $^{90}Y$, and $^{186}Re$.

In some embodiments, the cytotoxic agent is dolastatins or dolostatin peptidic analogs and derivatives, auristatin or monomethyl auristatin phenylalanine. Exemplary molecules are disclosed in U.S. Pat. Nos. 5,635,483 and 5,780,588. Dolastatins and auristatins have been shown to interfere with microtubule dynamics, GTP hydrolysis, and nuclear and cellular division (Woyke, Pettit et al. (2001) *Antimicrob Agents Chemother* 45: 3580-3584) and have anticancer and antifungal activity. The dolastatin or auristatin drug moiety may be attached to the FN3 domain of the invention through the N (amino) terminus or the C (carboxyl) terminus of the peptidic drug moiety (WO 02/088172), or via any cysteine engineered into the FN3 domain.

The FcγRII binding FN3 domains of the invention may be conjugated to a detectable label or a cytotoxic agent using known methods.

In some embodiments, the detectable label or the cytotoxic agent is complexed with a chelating agent.

In some embodiments, the detectable label is conjugated to the FcγRII binding FN3 domains of the invention via a linker.

The detectable label or the cytotoxic agent may be linked directly, or indirectly, to the FcγRII binding FN3 domains of the invention using known methods. Suitable linkers are known in the art and include, for example, prosthetic groups, non-phenolic linkers (derivatives of N-succimidyl-benzoates; dodecaborate), chelating moieties of both macrocyclics and acyclic chelators, such as derivatives of 1,4,7,10-tet-raazacyclododecane-1,4,7,10,tetraacetic acid (DOTA), derivatives of diethylenetriaminepentaacetic avid (DTPA), derivatives of S-2-(4-Isothiocyanatobenzyl)-1,4,7-triazacy-clononane-1,4,7-triacetic acid (NOTA) and derivatives of 1,4,8,11-tetraazacyclodocedan-1,4,8,11-tetraacetic acid (TETA), N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene) and other chelating moieties. Suitable peptide linkers are well known.

In some embodiment, the FcγRII binding FN3 domains of the invention is removed from the blood via renal clearance.

Polypeptide and Antibody Conjugates

The FcγRII binding FN3 domains may be conjugated to any polypeptide to provide FcγRII binding characteristics to the polypeptide. For example, antibodies with engineered effector silent Fc may be conjugated to the FcγRII binding FN3 domains of the invention to selectively rescue ADCP activity. Polypeptides that bind tumor antigens may be conjugated to the FcγRII binding FN3 domains of the invention to eliminate the tumor cells via ADCP.

The invention also provides for a method of enhancing antibody dependent cellular phagocytosis (ADCP) activity of a polypeptide, comprising conjugating to the polypeptide to a FcγRII binding FN3 domain and measuring enhanced ADCP activity of the polypeptide. In some embodiments, the FN3 domain comprises the polypeptide sequence of SEQ ID NOs: 16, 17, 18, 19, 20, 21 or 22. "Enhanced ADCP"

refers to enhancement i of about 10%, 20%, 30%, 40%, 50%, 60%, 70%, 80%, 90%, 100% or more, or a statistically significant enhancement mediated by the test molecule when compared to a negative control. ADCP activity may be measured using know protocols and those described herein.

Multispecific Molecules

The invention also provides for multispecific molecules comprising an anti-tumor necrosis factor receptor (TNFR) superfamily member antibody comprising a heavy chain or a fragment thereof and a light chain or a fragment thereof and a FcγRII binding FN3 domain. Conjugation of the FcγRII binding FN3 domain to anti-TNFR superfamily member antibodies enhance agonistic activity of the antibodies and provide ADCP activity in effector silent Fc antibodies.

In some embodiments, the anti-TNFR superfamily member antibody and the FcγRII binding FN3 domain are covalently coupled via a peptide bond.

In some embodiments, the FcγRII binding FN3 domain is coupled to the C-terminus of the heavy chain or a fragment thereof. In some embodiments, the FcγRII binding FN3 domain is coupled to the N-terminus of the heavy chain or a fragment thereof. In some embodiments, the FcγRII binding FN3 domain is coupled to the C-terminus of the light chain or a fragment thereof. In some embodiments, the FcγRII binding FN3 domain is coupled to the N-terminus of the light chain or a fragment thereof.

In some embodiments, the anti-TNFR superfamily member antibody is an IgG1 isotype. In some embodiments, the anti-TNFR superfamily member antibody is an IgG2 isotype. In some embodiments, the anti-TNFR superfamily member antibody is an IgG3 isotype. In some embodiments, the anti-TNFR superfamily member antibody is an IgG4 isotype. In some embodiments, the anti-TNFR superfamily member antibody comprises an effector silent Fc. "Effector silent" refers to an antibody that has no measurable ADCC, ADCP and CDC over the background. ADCC, ADCP and CDC can be measured using known methods and assays described herein. Fc positions that may be mutated to reduce binding of the antibody to the activating FcγR and subsequently to reduce effector function include positions 214, 233, 234, 235, 236, 237, 238, 265, 267, 268, 270, 295, 297, 309, 327, 328, 329, 330, 331 and 365. Exemplary mutations that may be made singularly or in combination are mutations K214T, E233P, L234V, L234A, deletion of G236, V234A, F234A, L235A, G237A, P238A, P238S, D265A, S267E, H268A, H268Q, Q268A, N297A, A327Q, P329A, D270A, Q295A, V309L, A327S, L328F, A330S and P331S in IgG1, IgG2, IgG3 or IgG4. Exemplary combination mutations that result in antibodies with reduced ADCC are mutations L234A/L235A on IgG1, V234A/G237A/P238S/H268A/V309L/A330S/P331S on IgG2, F234A/L235A on IgG4, S228P/F234A/L235A on IgG4, N297A on all Ig isotypes, V234A/G237A on IgG2, K214T/E233P/L234V/L235A/G236-deleted/A327G/P331A/D365E/L358M on IgG1, H268Q/V309L/A330S/P331S on IgG2, S267E/L328F on IgG1, L234F/L235E/D265A on IgG1, L234A/L235A/G237A/P238S/H268A/A330S/P331S on IgG1, S228P/F234A/L235A/G237A/P238S on IgG4, and S228P/F234A/L235A/G236-deleted/G237A/P238S on IgG4. Hybrid IgG2/4 Fc domains may also be used, such as Fc with residues 117-260 from IgG2 and residues 261-447 from IgG4. Exemplary mutation that result in antibodies with reduced CDC is a K322A mutation.

In some embodiments, the multispecific molecule comprising an anti-tumor necrosis factor receptor (TNFR) superfamily member antibody comprising a heavy chain or a fragment thereof and a light chain or a fragment thereof and a FcγRII binding FN3 domain binds OX40. In some embodiments, the multispecific molecule comprising an anti-tumor necrosis factor receptor (TNFR) superfamily member antibody comprising a heavy chain or a fragment thereof and a light chain or a fragment thereof and a FcγRII binding FN3 domain binds CD27. In some embodiments, the multispecific molecule comprising an anti-tumor necrosis factor receptor (TNFR) superfamily member antibody comprising a heavy chain or a fragment thereof and a light chain or a fragment thereof and a FcγRII binding FN3 domain binds CD40. In some embodiments, the multispecific molecule comprising an anti-tumor necrosis factor receptor (TNFR) superfamily member antibody comprising a heavy chain or a fragment thereof and a light chain or a fragment thereof and a FcγRII binding FN3 domain binds CD137. In some embodiments, the multispecific molecule comprising an anti-tumor necrosis factor receptor (TNFR) superfamily member antibody comprising a heavy chain or a fragment thereof and a light chain or a fragment thereof and a FcγRII binding FN3 domain binds GITR.

The invention also provides for multispecific molecules comprising an anti-tumor necrosis factor receptor (TNFR) superfamily member antibody comprising a heavy chain or a fragment thereof and a light chain or a fragment thereof and a FcγRII binding FN3 domain, wherein the FN3 domain comprises the amino acid sequence of SEQ ID NO: 16. In some embodiments, the FN3 domain is encoded by the polynucleotide of SEQ ID NO: 23. The invention also provides for multispecific molecules comprising an anti-tumor necrosis factor receptor (TNFR) superfamily member antibody comprising a heavy chain or a fragment thereof and a light chain or a fragment thereof and a FcγRII binding FN3 domain, wherein the FN3 domain comprises the amino acid sequence of SEQ ID NO: 17. In some embodiments, the FN3 domain is encoded by the polynucleotide of SEQ ID NO: 24. The invention also provides for multispecific molecules comprising an anti-tumor necrosis factor receptor (TNFR) superfamily member antibody comprising a heavy chain or a fragment thereof and a light chain or a fragment thereof and a FcγRII binding FN3 domain, wherein the FN3 domain comprises the amino acid sequence of SEQ ID NO: 18. In some embodiments, the FN3 domain is encoded by the polynucleotide of SEQ ID NO: 25. The invention also provides for multispecific molecules comprising an anti-tumor necrosis factor receptor (TNFR) superfamily member antibody comprising a heavy chain or a fragment thereof and a light chain or a fragment thereof and a FcγRII binding FN3 domain, wherein the FN3 domain comprises the amino acid sequence of SEQ ID NO: 19. In some embodiments, the FN3 domain is encoded by the polynucleotide of SEQ ID NO: 26 The invention also provides for multispecific molecules comprising an anti-tumor necrosis factor receptor (TNFR) superfamily member antibody comprising a heavy chain or a fragment thereof and a light chain or a fragment thereof and a FcγRII binding FN3 domain, wherein the FN3 domain comprises the amino acid sequence of SEQ ID NO: 20. In some embodiments, the FN3 domain is encoded by the polynucleotide of SEQ ID NO: 27. The invention also provides for multispecific molecules comprising an anti-tumor necrosis factor receptor (TNFR) superfamily member antibody comprising a heavy chain or a fragment thereof and a light chain or a fragment thereof and a FcγRII binding FN3 domain, wherein the FN3 domain comprises the amino acid sequence of SEQ ID NO: 21. In some embodiments, the FN3 domain is encoded by the polynucleotide of SEQ ID NO: 28. The invention also provides for multispecific molecules comprising an anti-tumor necrosis factor receptor (TNFR) superfamily member antibody comprising a heavy chain or a fragment thereof and a light chain or a fragment thereof and a FcγRII binding FN3 domain, wherein the FN3 domain comprises the amino acid sequence of SEQ ID NO: 22. In some embodiments, the FN3 domain is encoded by the polynucleotide of SEQ ID NO: 29.

The invention also provides for a multispecific molecule comprising an anti-tumor necrosis factor receptor (TNFR) superfamily member antibody comprising a heavy chain and a light chain and a FcγRII binding FN3 domain, wherein the multispecific molecule comprises polypeptides of SEQ ID NOs: 30 and 31. In some embodiments, the polypeptides are encoded by polynucleotides of SEQ ID NOs: 46 and 47.

The invention also provides for a multispecific molecule comprising an anti-tumor necrosis factor receptor (TNFR) superfamily member antibody comprising a heavy chain and a light chain and a FcγRII binding FN3 domain, wherein the multispecific molecule comprises polypeptides SEQ ID NOs: 32 and 31. In some embodiments, the polypeptides are encoded by polynucleotides of SEQ ID NOs: 48 and 47.

The invention also provides for a multispecific molecule comprising an anti-tumor necrosis factor receptor (TNFR) superfamily member antibody comprising a heavy chain and a light chain and a FcγRII binding FN3 domain, wherein the multispecific molecule comprises polypeptides SEQ ID NOs: 33 and 31. In some embodiments, the polypeptides are encoded by polynucleotides of SEQ ID NOs: 49 and 47.

The invention also provides for a multispecific molecule comprising an anti-tumor necrosis factor receptor (TNFR) superfamily member antibody comprising a heavy chain and a light chain and a FcγRII binding FN3 domain, wherein the multispecific molecule comprises polypeptides SEQ ID NOs: 34 and 31. In some embodiments, the polypeptides are encoded by polynucleotides of SEQ ID NOs: 50 and 47.

The invention also provides for a multispecific molecule comprising an anti-tumor necrosis factor receptor (TNFR) superfamily member antibody comprising a heavy chain and a light chain and a FcγRII binding FN3 domain, wherein the multispecific molecule comprises polypeptides SEQ ID NOs: 35 and 31. In some embodiments, the polypeptides are encoded by polynucleotides of SEQ ID NOs: 51 and 47

The invention also provides for a multispecific molecule comprising an anti-tumor necrosis factor receptor (TNFR) superfamily member antibody comprising a heavy chain and a light chain and a FcγRII binding FN3 domain, wherein the multispecific molecule comprises polypeptides SEQ ID NOs: 36 and 31. In some embodiments, the polypeptides are encoded by polynucleotides of SEQ ID NOs: 52 and 47.

The invention also provides for a multispecific molecule comprising an anti-tumor necrosis factor receptor (TNFR) superfamily member antibody comprising a heavy chain and a light chain and a FcγRII binding FN3 domain, wherein the multispecific molecule comprises polypeptides SEQ ID NOs: 37 and 31. In some embodiments, the polypeptides are encoded by polynucleotides of SEQ ID NOs: 53 and 47.

The invention also provides for a multispecific molecule comprising an anti-tumor necrosis factor receptor (TNFR) superfamily member antibody comprising a heavy chain and a light chain and a FcγRII binding FN3 domain, wherein the multispecific molecule comprises polypeptides SEQ ID NOs: 38 and 31. In some embodiments, the polypeptides are encoded by polynucleotides of SEQ ID NOs: 54 and 47.

The invention also provides for a multispecific molecule comprising an anti-tumor necrosis factor receptor (TNFR) superfamily member antibody comprising a heavy chain and a light chain and a FcγRII binding FN3 domain, wherein the multispecific molecule comprises polypeptides SEQ ID NOs: 39 and 31. In some embodiments, the polypeptides are encoded by polynucleotides of SEQ ID NOs: 55 and 47.

The invention also provides for a multispecific molecule comprising an anti-tumor necrosis factor receptor (TNFR) superfamily member antibody comprising a heavy chain and a light chain and a FcγRII binding FN3 domain, wherein the multispecific molecule comprises polypeptides SEQ ID NOs: 40 and 31. In some embodiments, the polypeptides are encoded by polynucleotides of SEQ ID NOs: 56 and 47.

The invention also provides for a multispecific molecule comprising an anti-tumor necrosis factor receptor (TNFR) superfamily member antibody comprising a heavy chain and a light chain and a FcγRII binding FN3 domain, wherein the multispecific molecule comprises polypeptides SEQ ID NOs: 30 and 41. In some embodiments, the polypeptides are encoded by polynucleotides of SEQ ID NOs: 46 and 57.

The invention also provides for a multispecific molecule comprising an anti-tumor necrosis factor receptor (TNFR) superfamily member antibody comprising a heavy chain and a light chain and a FcγRII binding FN3 domain, wherein the multispecific molecule comprises polypeptides SEQ ID NOs: 30 and 42. In some embodiments, the polypeptides are encoded by polynucleotides of SEQ ID NOs: 46 and 58.

The invention also provides for a multispecific molecule comprising an anti-tumor necrosis factor receptor (TNFR) superfamily member antibody comprising a heavy chain and a light chain and a FcγRII binding FN3 domain, wherein the multispecific molecule comprises polypeptides SEQ ID NOs: 43 and 31. In some embodiments, the polypeptides are encoded by polynucleotides of SEQ ID NOs: 59 and 47.

The invention also provides for a multispecific molecule comprising an anti-tumor necrosis factor receptor (TNFR) superfamily member antibody comprising a heavy chain and a light chain and a FcγRII binding FN3 domain, wherein the multispecific molecule comprises polypeptides SEQ ID NOs: 39 and 42. In some embodiments, the polypeptides are encoded by polynucleotides of SEQ ID NOs: 55 and 58.

The invention also provides for a method of enhancing agonistic activity of an anti-TNFR superfamily member antibody, comprising conjugating the antibody to a FcγRIIB binding FN3 domain to generate an engineered anti-TNFR superfamily member antibody and measuring the enhanced agonistic activity of the engineered anti-TNFR superfamily member antibody.

Polynucleotides, Vectors, Host Cells

The invention also provides nucleic acids encoding the FcγRII binding FN3 domains or the multispecific molecules of the invention as isolated polynucleotides or as portions of expression vectors or as portions of linear DNA sequences, including linear DNA sequences used for in vitro transcription/translation, vectors compatible with prokaryotic, eukaryotic or filamentous phage expression, secretion and/or display of the compositions or directed mutagens thereof. Certain exemplary polynucleotides are disclosed herein, however, other polynucleotides which, given the degeneracy of the genetic code or codon preferences in a given expression system, encode the FN3 domains or the multispecific molecules of the invention are also within the scope of the invention.

The invention also provides for an isolated polynucleotide encoding the FcγRII binding FN3 domain of SEQ ID NO: 16. The invention also provides for an isolated polynucleotide comprising the polynucleotide sequence of SEEQ ID NO: 23.

The invention also provides for an isolated polynucleotide encoding the FcγRII binding FN3 domain of SEQ ID NO:

17. The invention also provides for an isolated polynucleotide comprising the polynucleotide sequence of SEEQ ID NO: 24.

The invention also provides for an isolated polynucleotide encoding the FcγRII binding FN3 domain of SEQ ID NO: 18. The invention also provides for an isolated polynucleotide comprising the polynucleotide sequence of SEEQ ID NO: 25.

The invention also provides for an isolated polynucleotide encoding the FcγRII binding FN3 domain of SEQ ID NO: 19. The invention also provides for an isolated polynucleotide comprising the polynucleotide sequence of SEEQ ID NO: 26.

The invention also provides for an isolated polynucleotide encoding the FcγRII binding FN3 domain of SEQ ID NO: 20. The invention also provides for an isolated polynucleotide comprising the polynucleotide sequence of SEEQ ID NO: 27.

The invention also provides for an isolated polynucleotide encoding the FcγRII binding FN3 domain of SEQ ID NO: 21. The invention also provides for an isolated polynucleotide comprising the polynucleotide sequence of SEEQ ID NO: 28.

The invention also provides for an isolated polynucleotide encoding the FcγRII binding FN3 domain of SEQ ID NO: 22. The invention also provides for an isolated polynucleotide comprising the polynucleotide sequence of SEEQ ID NO: 29.

The invention also provides for an isolated polynucleotide encoding the polypeptide of SEQ ID NOs: 30, 31, 32, 33, 34, 35, 36, 37, 38, 39, 40, 41, 42 or 43.

The invention also provides for an isolated polynucleotide comprising the polynucleotide sequence of SEQ ID NOs: 46, 47, 48, 49, 50, 51, 52, 53, 54, 55, 56, 57, 58 or 59.

The polynucleotides of the invention may be produced by chemical synthesis such as solid phase polynucleotide synthesis on an automated polynucleotide synthesizer and assembled into complete single or double stranded molecules. Alternatively, the polynucleotides of the invention may be produced by other techniques such as PCR followed by routine cloning. Techniques for producing or obtaining polynucleotides of a given known sequence are well known in the art.

The polynucleotides of the invention may comprise at least one non-coding sequence, such as a promoter or enhancer sequence, intron, polyadenylation signal, a cis sequence facilitating RepA binding, and the like. The polynucleotide sequences may also comprise additional sequences encoding additional amino acids that encode for example a marker or a tag sequence such as a histidine tag or an HA tag to facilitate purification or detection of the protein, a signal sequence, a fusion protein partner such as RepA, Fc or bacteriophage coat protein such as pIX or pIII.

The invention also provides for a vector comprising at least one polynucleotide of the invention. Such vectors may be plasmid vectors, viral vectors, vectors for baculovirus expression, transposon based vectors or any other vector suitable for introduction of the polynucleotides of the invention into a given organism or genetic background by any means. Such vectors may be expression vectors comprising nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art.

The invention also provides for a host cell comprising the vector of the invention. The polypeptides of the invention may be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, NY (1987-2001); Sambrook, et al., Molecular Cloning: A Laboratory Manual, $2^{nd}$ Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

The host cell chosen for expression may be of mammalian origin or may be selected from COS-1, COS-7, HEK293, BHK21, CHO, BSC-1, He G2, SP2/0, HeLa, myeloma, lymphoma, yeast, insect or plant cells, or any derivative, immortalized or transformed cell thereof. Alternatively, the host cell may be selected from a species or organism incapable of glycosylating polypeptides, e.g. a prokaryotic cell or organism, such as BL21, BL21(DE3), BL21-GOLD (DE3), XL1-Blue, JM109, HMS174, HMS174(DE3), and any of the natural or engineered *E. coli* spp, *Klebsiella* spp., or *Pseudomonas* spp strains.

The invention also provides for a method of producing the isolated FcγRII binding FN3 domain of the invention, comprising culturing the isolated host cell of the invention under conditions such that the isolated FN3 domain is expressed, and purifying the FN3 domain.

The FcγRII binding FN3 domains may be purified from recombinant cell cultures by well-known methods, for example by protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography, or high performance liquid chromatography (HPLC).

Anti-Idiotypic Antibodies

The present invention also provides for an anti-idiotypic antibody binding to the FcγRII binding FN3 domain of the invention.

The invention also provides an anti-idiotypic antibody that specifically binds the FcγRII binding FN3 domain of SEQ ID NOs: 16, 17, 18, 19, 20, 21 or 22.

Kits

The invention also provides a kit comprising the FcγRII binding FN3 domain of the invention.

The kit may be used for therapeutic uses and as a diagnostic kit.

In some embodiments, the kit comprises the FcγRII binding FN3 domain of the invention and reagents for detecting the FN3 domain. The kit can include one or more other elements including: instructions for use; other reagents, e.g., a label, an agent useful for chelating, or otherwise coupling, a radioprotective composition; devices or other materials for preparing the FcγRII binding FN3 domain of the invention for administration for imaging, diagnostic or therapeutic purpose; pharmaceutically acceptable carriers; and devices or other materials for administration to a subject.

In some embodiments, the kit comprises the FcγRII binding FN3 domain of SEQ ID NOs: 16, 17, 18, 19, 20, 21 or 22.

Uses of the FcγRII Binding FN3 Domains and the Multispecific Molecule Comprising an Anti-Tumor Necrosis Factor Receptor (TNFR) Superfamily Member Antibody Comprising a Heavy Chain and a Light Chain and a FcγRII Binding FN3 Domain.

The FcγRII binding FN3 domains are useful to monitor activated immune cells engaged in endocytosis and phagocytosis as well as leukocytes except for NK and T cells.

Blocking human FcγRIIA, which contains an immunoreceptor tyrosine-based activation motif (ITAM) in its intracellular domain using the FN3 domains of the invention may block downstream signaling events leading to release of calcium from the endoplasmic reticulum (ER). Blocking FcγRIIA usign the FN3 domains of the invention may lower the immune response of hyper-activated patients with RA, psoriasis, Chrohn's disease, ulcerative colitis, or diabetes.

Antibody binding to cellular FγRs efficiently induces pro-inflammatory responses that lead to the removal of virus-infected or malignant cells, but it can also lead to the destruction of healthy tissues during autoimmune responses. Therefore, antibody specificity, as well as class switching to antibody isotypes that efficiently trigger pro-inflammatory reactions through their interaction with cellular FcγRs have to be tightly controlled. Several central and peripheral checkpoints exist throughout B-cell development to prevent the generation of autoreactive antibodies. Blocking of human FcγRIIB using the FN3 domains of the invention may block potential crosslinking of the receptor that leads to phosphorylation of the ITIM (immunoreceptor tyrosine-based inhibitory motif) in the cytoplasmic tail of FcγRIIB by LYN. This signaling cascade results in the recruitment of SRC-homology-2-domain-containing inositol-5-phosphatase (SHIP) and the hydrolysis of PtdIns(3,4,5)P3 into phosphatidylinositol-4,5-bisphosphate (PtdIns(4,5)P2), which ultimately inhibits recruitment of pleckstrin homology (PH)-domain containing proteins such as BTK and PLCγ. Thus blocking of FcγRIIB usign the FN3 domains of the invention may lower the ability of cancer cells or chronic viral infection inhibition of the immune response that they use to evade the human immune response.

The invention also provides for a method of treating an autoimmune disease, comprising administering to a subject in need thereof a therapeutically effective amount of the FcγRII binding FN3 domain of the invention to treat the autoimmune disease. In some embodiments, the FcγRII binding FN3 domain of the invention comprises the amino acid sequence of SEQ ID NOs: 16, 17, 18, 19, 20, 21 or 22. In some embodiments, FcγRII is FcγRIIB.

In some embodiments, the autoimmune disease is rheumatoid arthritis (RA). In some embodiments, the autoimmune disease is psoriasis. In some embodiments, the autoimmune disease is Chrohn's disease. In some embodiments, the autoimmune disease is uncerative colitis. In some embodiments, the autoimmune disease is diabetes.

The invention also provides for a method of treating a viral infection, comprising administering to a subject in need thereof a therapeutically effective amount of the FcγRII binding FN3 domain of the invention to treat the viral infection. In some embodiments, the FcγRII binding FN3 domain of the invention comprises the amino acid sequence of SEQ ID NOs: 16, 17, 18, 19, 20, 21 or 22. In some embodiments, FcγRII is FcγRIIB.

The invention also provides for a method of treating a cancer, comprising administering to a subject in need thereof a therapeutically effective amount of the FcγRII binding FN3 domain of the invention to treat the cancer. In some embodiments, the FcγRII binding FN3 domain of the invention comprises the amino acid sequence of SEQ ID NOs: 16, 17, 18, 19, 20, 21 or 22. In some embodiments, FcγRII is FcγRIIB.

The invention also provides for a method of treating a cancer, comprising administering to a subject in need thereof a therapeutically effective amount of the multispecific molecule comprising an anti-tumor necrosis factor receptor (TNFR) superfamily member antibody comprising a heavy chain or a fragment thereof and a light chain or a fragment thereof and a FcγRII binding FN3 domain of the invention. In some embodiments, FcγRII is FcγRIIB.

The invention also provides for a method of treating a cancer, comprising administering to a subject in need thereof a therapeutically effective amount of the multispecific molecule comprising an anti-tumor necrosis factor receptor (TNFR) superfamily member antibody comprising a heavy chain and a light chain and a FcγRII binding FN3 domain of the invention. In some embodiments, FcγRII is FcγRIIB.

In some embodiments, the TNFR superfamily member is OX40, CD27, CD40, CD137 or GITR.

In some embodiments, the cancer is a solid tumor. In some embodiments, the solid tumor is a melanoma, a lung cancer, a squamous non-small cell lung cancer (NSCLC), a non-squamous NSCLC, a colorectal cancer, a prostate cancer, a castration-resistant prostate cancer, a stomach cancer, an ovarian cancer, a gastric cancer, a liver cancer, a pancreatic cancer, a thyroid cancer, a squamous cell carcinoma of the head and neck, a carcinoma of the esophagus or gastrointestinal tract, a breast cancer, a fallopian tube cancer, a brain cancer, an urethral cancer, a genitourinary cancer, an endometriosis, a cervical cancer or a metastatic lesion of the cancer.

Many of the TNFR superfamily members and their ligands have been implicated as targets for cancer therapy, including TNFR1/2/TNF-α, CD70/CD27, CD137/4-1BB, OX40/OX40L, CD40/CD40L, GITR/GITRL and several agonistic antibodies targeting the TNFR superfamily members, such as anti-CD40, anti-OX-40, anti-GITR, anti-CD27, anti-CD137 antibodies are in clinical development for various solid tumors as well as heme malignancies such as non-Hodgkin's lymphoma and B-cell malignancies. It can be expected that anti-CD40, anti-OX40, anti-GITR, anti-CD27, anti-CD137 and other anti-TNFR superfamily member antibodies of the invention with improved properties in terms of their enhanced agonistic activity optionally coupled with effector functionality will be therapeutically effective in the treatment of various cancers, including solid tumors.

Pharmaceutical Compositions/Administration

The invention also provides for pharmaceutical compositions comprising the FcγRII binding FN3 domains or the multispecific molecules of the invention and a pharmaceutically acceptable carrier. For therapeutic use, the FcγRII binding FN3 domains or the multispecific molecules of the invention may be prepared as pharmaceutical compositions containing an effective amount of the antibody or the Fc domain containing molecule as an active ingredient in a pharmaceutically acceptable carrier. Exemplary pharmaceutically acceptable carriers are solvents, dispersion media, coatings, antibacterial and antifungal agents, isotonic and absorption delaying agents, and the like that are physiologically compatible, such as salts, buffers, antioxidants, saccharides, aqueous or non-aqueous carriers such as vegetable oil or peanut oil, preservatives, wetting agents, surfactants or emulsifying agents, or combinations thereof.

Exemplary buffers that may be used are acetic acid, citric acid, formic acid, succinic acid, phosphoric acid, carbonic acid, malic acid, aspartic acid, histidine, boric acid, Tris buffers, HEPPSO and HEPES. The concentration of the buffers in the pharmaceutical composition may be about 10 mM, about 15 mM, about 20 mM, about 25 mM, about 30 mM, about 35 mM, about 40 mM, about 45 mM or about 50 mM.

Exemplary amino acids that may be used are histidine, isoleucine, methionine, glycine, arginine, lysine, L-leucine, tri-leucine, alanine, glutamic acid, L-threonine, and 2-phenylamine. The concentration of the amino acids in the pharmaceutical compositions may be 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM or about 50 mM.

Exemplary surfactants that may be used are polysorbates (e.g., polysorbate-20 or polysorbate-80); polyoxamers (e.g., poloxamer 188); Triton; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUA™ series (Mona Industries, Inc., Paterson, N.J.), polyethyl glycol, polypropyl glycol, and copolymers of ethylene and propylene glycol (e.g., PLURONICS™, PF68, etc). The concentration of the surfactants in the pharmaceutical compositions may be about 0.01% w/v, 0.02% w/v, 0.03% w/v, 0.04% w/v, 0.05% w/v, 0.06% w/v, 0.07% w/v, 0.08% w/v, 0.09% w/v or 0.1% w/v.

Exemplary saccharides that may be used are monosaccharides, disaccharides, trisaccharides, polysaccharides, sugar alcohols, reducing sugars, nonreducing sugars such as glucose, sucrose, trehalose, lactose, fructose, maltose, dextran, glycerin, dextran, erythritol, glycerol, arabitol, sylitol, sorbitol, mannitol, mellibiose, melezitose, raffinose, mannotriose, stachyose, maltose, lactulose, maltulose, glucitol, maltitol, lactitol or iso-maltulose. The concentration of the saccharides in the pharmaceutical compositions may be about 100 mM, about 110 mM, about 120 mM, about 130 mM, about 140 mM, about 150 mM, about 160 mM, about 170 mM, about 180 mM, about 190 mM, about 200 mM, about 210 mM, about 220 mM, about 230 mM, about 240 mM, about 250 mM, about 260 mM, about 270 mM, about 280 mM, about 290 mM, about 300 mM, about 310 mM, about 320 mM, about 330 mM, about 340 mM, about 350 mM, about 360 mM, about 370 mM, about 380 mM, about 390 mM, about 400 mM, about 410 mM, about 420 mM, about 430 mM, about 440 mM, about 450 mM, about 460 mM, about 470 mM, about 480 mM, about 490 mM or about 500 mM.

Exemplary salts that may be used are acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like. The concentration of the salts in the pharmaceutical compositions may be about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM or about 100 mM.

Exemplary antioxidants that may be used are ascorbic acid, methionine, cysteine hydrochloride, sodium bisulfate, sodium metabisulfite, sodium sulfite, lecithin, citric acid, ethylenediamine tetraacetic acid (EDTA), sorbitol and tartaric acid.

Exemplary preservatives that may be used are phenol, m-cresol, p-cresol, o-cresol, chlorocresol, benzyl alcohol, phenylmercuric nitrite, phenoxyethanol, formaldehyde, chlorobutanol, magnesium chloride, alkylparaben (methyl, ethyl, propyl, butyl and the like), benzalkonium chloride, benzethonium chloride, sodium dehydroacetate and thimerosal, or mixtures thereof.

The amounts of pharmaceutically acceptable carrier(s) in the pharmaceutical compositions may be determined experimentally based on the activities of the carrier(s) and the desired characteristics of the formulation, such as stability and/or minimal oxidation. The concentration of the FcγRII binding FN3 domains or the multispecific molecules of the invention in such pharmaceutical formulation may hence vary, from less than about 0.5%, usually to at least about 1% to as much as 15 or 20% by weight and may be selected primarily based on required dose, fluid volumes, viscosities, etc., according to the particular mode of administration selected.

An exemplary pharmaceutical composition comprises 20 mM L-Histidine, 100 mM NaCl, 15 mM L-Methionine and 0.02% Polysorbate 80. The pharmaceutical compositions are sterile and generally free of particulate matter. They may be sterilized by conventional, well-known sterilization techniques (e.g., filtration).

The mode of administration for therapeutic use of the FcγRII binding FN3 domains or the multispecific molecules of the invention may be any suitable route that delivers the antibody to the host, such as parenteral administration, e.g., intradermal, intramuscular, intraperitoneal, intravenous or subcutaneous, pulmonary, transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intratumoral, intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

The FcγRII binding FN3 domains or the multispecific molecules of the invention may be administered to a subject by any suitable route, for example parentally by intravenous (i.v.) infusion or bolus injection, intramuscularly or subcutaneously or intraperitoneally. i.v. infusion may be given over for example 15, 30, 60, 90, 120, 180, or 240 minutes, or from 1, 2, 3, 4, 5, 6, 7, 8, 9, 10, 11 or 12 hr.

The dose given to a subject is sufficient to alleviate or at least partially arrest the disease being treated ("therapeutically effective amount") and may be sometimes 0.005 mg to about 100 mg/kg, e.g. about 0.05 mg to about 30 mg/kg or about 5 mg to about 25 mg/kg, or about 4 mg/kg, about 8 mg/kg, about 16 mg/kg or about 24 mg/kg, or for example about 1, 2, 3, 4, 5, 6, 7, 8, 9 or 10 mg/kg, but may even higher, for example about 15, 16, 17, 18, 19, 20, 21, 22, 23, 24, 25, 30, 40, 50, 60, 70, 80, 90 or 100 mg/kg.

A fixed unit dose may also be given, for example, 50, 100, 200, 500 or 1000 mg, or the dose may be based on the patient's surface area, e.g., 500, 400, 300, 250, 200, or 100 mg/m$^2$. Usually between 1 and 8 doses, (e.g., 1, 2, 3, 4, 5, 6, 7 or 8) may be administered to treat the patient, but 9, 10, 11, 12, 13, 14, 15, 16, 17, 18, 19, 20 or more doses may be given.

The administration of the FcγRII binding FN3 domains or the multispecific molecules of the invention may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose. For example, the FcγRII binding FN3 domains or the multispecific molecules of the invention may be administered at 8 mg/kg or at 16 mg/kg at weekly interval for 8 weeks, followed by administration at 8 mg/kg or at 16 mg/kg every two weeks for an additional 16 weeks, followed by administration at 8 mg/kg or at 16 mg/kg every four weeks by intravenous infusion.

For example, the FcγRII binding FN3 domains or the multispecific molecules of the invention may be provided as a daily dosage in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hr, or any combination thereof.

The FcγRII binding FN3 domains or the multispecific molecules of the invention may also be administered prophylactically to reduce the risk of developing cancer, delay the onset of the occurrence of an event in cancer progression, and/or reduce the risk of recurrence when a cancer is in remission.

The FcγRII binding FN3 domains or the multispecific molecules of the invention may be lyophilized for storage and reconstituted in a suitable carrier prior to use. This technique has been shown to be effective with conventional protein preparations and well known lyophilization and reconstitution techniques can be employed.

While having described the invention in general terms, the embodiments of the invention will be further disclosed in the following examples that should not be construed as limiting the scope of the claims.

Example 1. Selection of Fibronectin Type III (FN3) Domains that Bind FcγRII

FcγRII binding FN3 domains were selected from libraries based on stabilized Tencon27 (SEQ ID NO: 5).

Antigens were labeled with SureLINK Biotin Kit (KPL #86-00-01) using 10-fold molar excess of biotin to antigen in 1×PBS Panning was performed through 5 successive rounds beginning to enrich for specific binding clones. Multiple panning approaches were executed, including biotinylated (bt) FcγRIIB bound to beads, bt-FcγRIIB bound to beads with unlabeled FcγRIIA in excess in library blocking, bt-FcγRIIA bound to negative selection beads prior to bt-FcγRIIB bound to positive selection beads, and an epitope blocking panning.

FN3 domain panning outputs were screened for binding to FcγRIIA and FcγRIIB by ELISA at rounds three and five. Specifically, output material was amplified by PCR and subcloned into a pET15 E. coli expression vector [BL21 competent cells (Agilent #230132)] using the Clontech InFusion system (Clontech #639649). Subcloned FN3 domain expressing plasmids were then selected overnight on carbenicillin agar plates. Approximately one-hundred colonies from each panning and library were picked from each library panned (~4000 total from the 4 panning methods), scaled for growth, induced for expression, isolated, and lysed for primary ELISA screenings.

For primary ELISA, Maxisorp 96-well plates were loaded with 100 μL per well of streptavidin (Promega; 5 μg/mL in PBS) and then held at 4° C. overnight. The next day, the streptavidin-coated plates were washed 3×TBST and then blocked with 250 μL Starting Block T20 (Pierce-cat #37543). After a 1 h incubation, all plates were washed 3 times with 1×TBST, loaded with 100 μL per well of either bt-FcγRIIA, bt-FcγRIIB, or bt-HSA (negative screen) all at 1 μg/mL, and held at room temperature for 1 h. The previously lysed FN3 domains were centrifuged at 3500 rpm for 10 minutes, diluted 1:10 in Starting Block T20 and added 100 μL each to the plates. After a 1 h incubation at room temperature, the plates were washed 3× with 1×TBST and the wells were loaded with 100 μL of a HRP conjugated rabbit polyclonal antibody against tencon 27. After a final 1 h incubation at room temperature, the plates were washed 3× with 1×TBST, loaded with 100 μL per well of the chemiluminescence substrate POD (Roche), and read in a Perkin Elmer Envision plate reader. Positive binding colonies (those clones showing 5-fold higher binding to FcγRIIA or FcγRIIB when compared to HSA) were subjected to Sanger sequencing and identified coding sequences were in silico translated to amino acid sequences. Sequence unique FN3 domains were expressed in BL21 cells and purified using nickel sepharose plates. Antigen binding of purified FN3 domains in a dilution series was performed. Specifically, in an ELISA format, Streptavidin coated plates (Promega #Z7041) were used to capture 50 μL of 1 μg/mL of either bt-FcγRIIB, bt-FcγRIIA, or as a negative control against sticky FN3 domains bt-HSA. To this FN3 domains were added at 10 μM then diluted 1:5 down to 128 pM, and detected for binding using a HRP conjugated rabbit polyclonal against tencon 27 and POD substrate (Roche #11582950001). Binding curves and EC50 values were calculated using X=log(x) transformation and non-linear regression (curved slope) calculations of Prism GraphPad.

Purified FN3 domains were assessed by size exclusion chromatography HPLC (Agilent 1100) in 1×PBS using a Superdex 75 5/150 GL column (SE Lifesciences #28-9205-04). Monomeric content was quantitated by monitored absorbance (280 nm) corrected for light scattering. Monomeric Tencon27 was used as a reference control to identify FN3 domains with a similar apparent size based on elution time. Percent of monomeric material at appropriate times was calculated by integrative analysis using OpenLab ECM (Agilent Systems). Those clones with a peak in the expected time range around +/−1 minute from Tencon27 with generally greater than 50% area were summarized as monomeric. Those clones with no visible peak in time range were considered not monomeric.

Based on initial binding and size exclusion chromatography and subsequent functional screening using NFκB reporter assay, seven FN3 domains that bind FcγRII were characterized further. These FN3 domains originated from the Tencon alternative C-CD-F-FG surface library described in U.S. Pat. Publ. No. US2013/0226834 having diversified C strand, CD loop, F strand and FG loop. The amino acid and cDNA sequences of the selected FN3 domains are shown in Table 3 and Table 4, respectively. FIG. 1 shows the amino acid alignment of the FN3 domains. The EC50 values for binding to FcγRIIa and FcγRIIb are shown in Table 5. From the clones shown in Table 5, R2BS6, R2B12, R2B29 add R2B56 were monomeric.

TABLE 3

| FN3 domain | AA Sequence | SEQ ID NO: |
|---|---|---|
| R2BS6 | LPAPKNLVVSRVTEDSARLSWTAPDAAFDSFLIQY QESEKVGEAIVLTVPGSERSYDLTGLKPGTEYTVS IYGVQYAAWYLPRHHEASNPLSAIFTT | 16 |
| R2BS9 | LPAPKNLVVSRVTEDSARLSWTAPDAAFDSFWIY YLEYWRGGEAIVLTVPGSERSYDLTGLKPGTEYF VQIHGVKGGQYSYPLSAIFTT | 17 |
| R2BS12 | LPAPKNLVVSRVTEDSARLSWTAPDAAFDSFLIAY AEYWEGGEAVVLTVPGSERSYDLTGLKPGTEYFV QINGVKGGFWSIPLSAIFTT | 18 |
| R2BS26 | LPAPKNLVVSRVTEDSARLSWTAPDAAFDSFPIAY IEYWTGGEAIVLTVPGSERSYDLTGLKPGTEYFV WIHGVKGGAWSSPLSAIFTT | 19 |
| R2BS29 | LPAPKNLVVSRVTEDSARLSWTAPDAAFDSFPIYY WEYRVGGEAIVLTVPGSERSYDLTGLKPGTEYFV YINGVKGGEESRPLSAIFTT | 20 |
| R2BS39 | LPAPKNLVVSRVTEDSARLSWTAPDAAFDSFLIQY QESEKVGEAIVLTVPGSERSYDLTGLKPGTEYTVS IYGVSHGPWYNYGEWRSNPLSAIFTT | 21 |
| R2BS56 | LPAPKNLVVSRVTEDSARLSWTAPDAAFDSFSIAY WEYRKGGEAIVLTVPGSERSYDLTGLKPGTEYFV LIYGVKGGWQSKPLSAIFTT | 22 |

TABLE 4

| FN3 domain | cDNA sequence | SEQ ID NO: |
|---|---|---|
| R2BS6 | ctgccggcgccgaaaaacctggttgtttctcgtgttaccgaagactctgcgcgt ctgtcttggaccgcgccggacgcggcgttcgactcttcctgatccagtaccag gaatctgaaaaagttggtgaagcgatcgtgctgaccgttccgggttctgaacgt tcttacgacctgaccggtctgaaaccgggtaccgaatacaccgtttctatctacg gtgttcaatatgcggcgtggtatctgccgcgtcaccacgaggcgagcaaccc gctgtctgcgatcttcaccacc | 23 |
| R2BS9 | ctgccggcgccgaaaaacctggttgtttctcgtgttaccgaagactctgcgcgt ctgtcttggaccgcgccggacgcggcgttcgactcttctggatttattacctgg agtattggcgtggcggtgaagcgatcgttctgaccgttccgggttctgaacgtt cttacgacctgaccggtctgaaaccgggtaccgaatatttcgttcaaattcacg gcgttaagggcggtcaatatagttatccactgtctgcgatcttcaccacc | 24 |
| R2BS12 | ctgccggcgccgaaaaacctggttgtttctcgtgttaccgaagactctgcgcgt ctgtcttggaccgcgccggacgcggcgttcgactcttttctgatcgcgtatgcg gaatattgggagggcggtgaagcggtcgttctgaccgttccgggttctgaacg ttcttacgacctgaccggtctgaaaccgggtaccgaatatttcgttcaaatcaat ggcgttaagggtggtttctggagtatcccactgtctgcgatcttcaccacc | 25 |
| R2BS26 | ctgccggcgccgaaaaacctggttgtttctcgtgttaccgaagactctgcgcgt ctgtcttggaccgcgccggacgcggcgttcgactcttttccgatcgcgtatatc gagtattggactggcggtgaagcgatcgttctgaccgttccgggttctgaacgt tcttacgacctgaccggtctgaaaccgggtaccgaatatttcgtttggattcacg gcgttaagggtggtgcgtggccagcccgctgtctgcgatcttcaccacc | 26 |
| R2BS29 | ctgccggcgccgaaaaacctggttgtttctcgtgttaccgaagactctgcgcgt ctgtcttggaccgcgccggacgcggcgttcgactcttttccgatctattattggg aatatcgtgttggcggtgaagcgatcgttctgaccgttccgggttctgaacgttc ttacgacctgaccggtctgaaaccgggtaccgaatacttcgtttatatcaatggt gttaaaggtggcgaggagagtcgtccgctgtctgcgatcttcaccacc | 27 |
| R2BS39 | ctgccggcgccgaaaaacctggttgtttctcgtgttaccgaagactctgcgcgt ctgtcttggaccgcgccggacgcggcgttcgactcttcctgatccagtaccag gaatctgaaaaagttggtgaagcgatcgtgctgaccgttccgggttctgaacgt tcttacgacctgaccggtctgaaaccgggtaccgaatacaccgtttctatctacg gtgtgagccacgcccgtgtataattatggcgagtggcgttctaacccgctgt ctgcgatcttcaccacc | 28 |

TABLE 4-continued

| FN3 domain | cDNA sequence | SEQ ID NO: |
|---|---|---|
| R2BS56 | ctgccggcgccgaaaaacctggttgtttctcgtgttaccgaagactctgcgcgt ctgtcttggaccgcgccggacgcggcgttcgactcttttagcattgcgtactgg gagtatcgtaaaggcggtgaagcgatcgttctgaccgttccgggtctgaacgt tcttacgacctgaccggtctgaaaccgggtaccgaatatttcgactgatctatg gtgtcaagggcggttggcaatccaaaccactgtctgcgatcttcaccacc | 29 |

TABLE 5

| FN3 domain | FcγRIIA EC$_{50}$ (M) | FcγRIIb EC$_{50}$ (M) |
|---|---|---|
| R2BS6 | 2.73E−08 | 7.59E−09 |
| R2BS9 | 5.49E−09 | 4.51E−09 |
| R2BS12 | 9.60E−09 | 4.30E−08 |
| R2BS26 | 6.51E−09 | 5.30E−09 |
| R2BS29 | 3.22E−09 | 3.57E−09 |
| R2BS39 | 1.55E−08 | 4.19E−07 |
| R2BS56 | 5.50E−09 | 7.32E−09 |

Example 2: Generation of OX40-FcγRII mAbtyrins

To generate mAbtyrins, select FcγRII FN3 domains were engineered at the C-terminus of the heavy chain of an anti-OX40 antibody OX40SF2IgG2sigma (HC SEQ ID NO: 30, LC SEQ ID NO: 31) cloned as IgG2 sigma isotype (effector silent Fc having substitutions V234A, G237A, P238S, H268A, V309L, A330S and P331S when compared to the wild type IgG2). The binding to FcγRII, agonism in NF-kB reporter assay and ADCC/ADCP effector activities of the candidate mAbtyrins were evaluated. The parental antibody OX40SF2IgG2sigma was used as a control in the experiments. Table 6 shows the generated mAbtyrins.

TABLE 6

| mAbtyrin* | Heavy Chain name |
|---|---|
| OX40SF2IgG2sigma_R2BS6_HC-C | hcOX40SF2IgG2sigma_R2BS6_HC-C (SEQ ID NO: 32) |
| OX40SF2IgG2sigma_R2BS9_HC-C | hcOX40SF2IgG2sigma_R2BS9_HC-C (SEQ ID NO: 33) |
| OX40SF2IgG2sigma_R2BS12_HC-C | hcOX40SF2IgG2sigma_R2BS12_HC-C (SEQ ID NO: 34) |
| OX40SF2IgG2sigma_R2BS26_HC-C | hcOX40SF2IgG2sigma_R2BS26_HC-C (SEQ ID NO: 35) |
| OX40SF2IgG2sigma_R2BS29_HC-C | hcOX40SF2IgG2sigma_R2BS29_HC-C (SEQ ID NO: 36) |
| OX40SF2IgG2sigma_R2BS39_HC-C | hcOX40SF2IgG2sigma_R2BS39_HC-C (SEQ ID NO: 37) |
| OX40SF2IgG2sigma_R2BS56_HC-C | hcOX40SF2IgG2sigma_R2BS56_HC-C (SEQ ID NO: 38) |

*All mAbtyrins share the same light chain lcOX40SF2_LC (SEQ ID NO: 31)

```
hcOX40SF2IgG2sigma_HC amino acid
                                                                    (SEQ ID NO: 30)
QVQLVQSGAEVKKPGSSVKVSCKASGYTFKDYTMHWVRQAPGQGLEWIGGIYP

NNGGSTYNQNFKDRVTLTADKSTSTAYMELSSLRSEDTAVYYCARMGYHGPHL

DFDVWGQGTTVTVSSASTKGPSVFPLAPCSRSTSESTAALGCLVKDYFPEPVTVS

WNSGALTSGVHTFPAVLQSSGLYSLSSVVTVPSSNFGTQTYTCNVDHKPSNTKVD

KTVERKCCVECPPCPAPPAAASSVFLFPPKPKDTLMISRTPEVTCVVVDVSAEDPE

VQFNWYVDGVEVHNAKTKPREEQFNSTFRVVSVLTVLHQDWLNGKEYKCKVSN

KGLPSSIEKTISKTKGQPREPQVYTLPPSREEMTKNQVSLTCLVKGFYPSDIAVEWE

SNGQPENNYKTTPPMLDSDGSFFLYSKLTVDKSRWQQGNVFSCSVMHEALHNHY

TQKSLSLSPGK

OX40SF2_LC amino acid
                                                                    (SEQ ID NO: 31)
DIQMTQSPSSLSASVGDRVTITCKASQDVGAAVAWYQQKPGKAPKLLIYWASTR

HTGVPSRFSGSGSGTDFTLTISSLQPEDFATYYCQQYINYPLTFGGGTKVEIKRTVA

APSVFIFPPSDEQLKSGTASVVCLLNNFYPREAKVQWKVDNALQSGNSQESVTEQ

DSKDSTYSLSSTLTLSKADYEKHKVYACEVTHQGLSSPVTKSFNRGEC
```

-continued hcOX40SF2IgG2sigma_R2BS6_HC-C amino acid (hcOX40SF2IgG2sigma_HC + linker + R2BS6 FN3 domain)

(SEQ ID NO: 32)

QVQLVQSGAEVKKPGSSVKVSCKASGYTFKDYTMHWVRQAPGQGLEWIGGIYP

NNGGSTYNQNFKDRVTLTADKSTSTAYMELSSLRSEDTAVYYCARMGYHGPHL

DFDVWGQGTTVTVSSASTKGPSVFPLAPCSRSTSESTAALGCLVKDYFPEPVTVS

WNSGALTSGVHTFPAVLQSSGLYSLSSVVTVPSSNFGTQTYTCNVDHKPSNTKVD

KTVERKCCVECPPCPAPPAAASSVFLFPPKPKDTLMISRTPEVTCVVVDVSAEDPE

VQFNWYVDGVEVHNAKTKPREEQFNSTFRVVSVLTVLHQDWLNGKEYKCKVSN

KGLPSSIEKTISKTKGQPREPQVYTLPPSREEMTKNQVSLTCLVKGFYPSDIAVEWE

SNGQPENNYKTTPPMLDSDGSFFLYSKLTVDKSRWQQGNVFSCSVMHEALHNHY

TQKSLSLSPGKGGGGGSGGGGSGGGGSGGGGSLPAPKNLVVSRVTEDSARLSWT

APDAAFDSFLIQYQESEKVGEAIVLTVPGSERSYDLTGLKPGTEYTVSIYGVQYAA

WYLPRHHEASNPLSAIFTT hcOX40SF2IgG2sigma_R2BS9_HC-C amino acid (hcOX40SF2IgG2sigma_HC + linker + R2BS9 FN3 domain)

(SEQ ID NO: 33)

QVQLVQSGAEVKKPGSSVKVSCKASGYTFKDYTMHWVRQAPGQGLEWIGGIYP

NNGGSTYNQNFKDRVTLTADKSTSTAYMELSSLRSEDTAVYYCARMGYHGPHL

DFDVWGQGTTVTVSSASTKGPSVFPLAPCSRSTSESTAALGCLVKDYFPEPVTVS

WNSGALTSGVHTFPAVLQSSGLYSLSSVVTVPSSNFGTQTYTCNVDHKPSNTKVD

KTVERKCCVECPPCPAPPAAASSVFLFPPKPKDTLMISRTPEVTCVVVDVSAEDPE

VQFNWYVDGVEVHNAKTKPREEQFNSTFRVVSVLTVLHQDWLNGKEYKCKVSN

KGLPSSIEKTISKTKGQPREPQVYTLPPSREEMTKNQVSLTCLVKGFYPSDIAVEWE

SNGQPENNYKTTPPMLDSDGSFFLYSKLTVDKSRWQQGNVFSCSVMHEALHNHY

TQKSLSLSPGKGGGGGSGGGGSGGGGSGGGGSLPAPKNLVVSRVTEDSARLSWT

APDAAFDSFWIYYLEYWRGGEAIVLTVPGSERSYDLTGLKPGTEYFVQIHGVKGG

QYSYPLSAIFTT hcOX40SF2IgG2sigma_R2BS12_HC-C amino acid (hcOX40SF2IgG2sigma_HC + linker + R2BS12 FN3 domain)

(SEQ ID NO: 34)

QVQLVQSGAEVKKPGSSVKVSCKASGYTFKDYTMHWVRQAPGQGLEWIGGIYP

NNGGSTYNQNFKDRVTLTADKSTSTAYMELSSLRSEDTAVYYCARMGYHGPHL

DFDVWGQGTTVTVSSASTKGPSVFPLAPCSRSTSESTAALGCLVKDYFPEPVTVS

WNSGALTSGVHTFPAVLQSSGLYSLSSVVTVPSSNFGTQTYTCNVDHKPSNTKVD

KTVERKCCVECPPCPAPPAAASSVFLFPPKPKDTLMISRTPEVTCVVVDVSAEDPE

VQFNWYVDGVEVHNAKTKPREEQFNSTFRVVSVLTVLHQDWLNGKEYKCKVSN

KGLPSSIEKTISKTKGQPREPQVYTLPPSREEMTKNQVSLTCLVKGFYPSDIAVEWE

SNGQPENNYKTTPPMLDSDGSFFLYSKLTVDKSRWQQGNVFSCSVMHEALHNHY

TQKSLSLSPGKGGGGGSGGGGSGGGGSGGGGSLPAPKNLVVSRVTEDSARLSWT

APDAAFDSFLIAYAEYWEGGEAVVLTVPGSERSYDLTGLKPGTEYFVQINGVKGG

FWSIPLSAIFTT hcOX40SF2IgG2sigma_R2BS26_HC-C amino acid (hcOX40SF2IgG2sigma_HC + linker + R2BS26 FN3 domain)

(SEQ ID NO: 35)

QVQLVQSGAEVKKPGSSVKVSCKASGYTFKDYTMHWVRQAPGQGLEWIGGIYP

NNGGSTYNQNFKDRVTLTADKSTSTAYMELSSLRSEDTAVYYCARMGYHGPHL

```
DFDVWGQGTTVTVSSASTKGPSVFPLAPCSRSTSESTAALGCLVKDYFPEPVTVS

WNSGALTSGVHTFPAVLQSSGLYSLSSVVTVPSSNFGTQTYTCNVDHKPSNTKVD

KTVERKCCVECPPCPAPPAAASSVFLFPPKPKDTLMISRTPEVTCVVVDVSAEDPE

VQFNWYVDGVEVHNAKTKPREEQFNSTFRVVSVLTVLHQDWLNGKEYKCKVSN

KGLPSSIEKTISKTKGQPREPQVYTLPPSREEMTKNQVSLTCLVKGFYPSDIAVEWE

SNGQPENNYKTTPPMLDSDGSFFLYSKLTVDKSRWQQGNVFSCSVMHEALHNHY

TQKSLSLSPGKGGGGGSGGGGSGGGGSGGGGSLPAPKNLVVSRVTEDSARLSWT

APDAAFDSFPIAYIEYWTGGEAIVLTVPGSERSYDLTGLKPGTEYFVWIHGVKGGA

WSSPLSAIFTT hcOX40SF2IgG2sigma_R2BS29_HC-C amino acid (hcOX40SF2IgG2sigma_HC +
linker + R2BS29 FN3 domain)

(SEQ ID NO: 36)
QVQLVQSGAEVKKPGSSVKVSCKASGYTFKDYTMHWVRQAPGQGLEWIGGIYP

NNGGSTYNQNFKDRVTLTADKSTSTAYMELSSLRSEDTAVYYCARMGYHGPHL

DFDVWGQGTTVTVSSASTKGPSVFPLAPCSRSTSESTAALGCLVKDYFPEPVTVS

WNSGALTSGVHTFPAVLQSSGLYSLSSVVTVPSSNFGTQTYTCNVDHKPSNTKVD

KTVERKCCVECPPCPAPPAAASSVFLFPPKPKDTLMISRTPEVTCVVVDVSAEDPE

VQFNWYVDGVEVHNAKTKPREEQFNSTFRVVSVLTVLHQDWLNGKEYKCKVSN

KGLPSSIEKTISKTKGQPREPQVYTLPPSREEMTKNQVSLTCLVKGFYPSDIAVEWE

SNGQPENNYKTTPPMLDSDGSFFLYSKLTVDKSRWQQGNVFSCSVMHEALHNHY

TQKSLSLSPGKGGGGGSGGGGSGGGGSGGGGSLPAPKNLVVSRVTEDSARLSWT

APDAAFDSFPIYYWEYRVGGEAIVLTVPGSERSYDLTGLKPGTEYFVYINGVKGG

EESRPLSAIFTT hcOX40SF2IgG2sigma_R2BS39_HC-C amino acid (hcOX40SF2IgG2sigma_HC +
linker + R2BS39 FN3 domain)

(SEQ ID NO: 37)
QVQLVQSGAEVKKPGSSVKVSCKASGYTFKDYTMHWVRQAPGQGLEWIGGIYP

NNGGSTYNQNFKDRVTLTADKSTSTAYMELSSLRSEDTAVYYCARMGYHGPHL

DFDVWGQGTTVTVSSASTKGPSVFPLAPCSRSTSESTAALGCLVKDYFPEPVTVS

WNSGALTSGVHTFPAVLQSSGLYSLSSVVTVPSSNFGTQTYTCNVDHKPSNTKVD

KTVERKCCVECPPCPAPPAAASSVFLFPPKPKDTLMISRTPEVTCVVVDVSAEDPE

VQFNWYVDGVEVHNAKTKPREEQFNSTFRVVSVLTVLHQDWLNGKEYKCKVSN

KGLPSSIEKTISKTKGQPREPQVYTLPPSREEMTKNQVSLTCLVKGFYPSDIAVEWE

SNGQPENNYKTTPPMLDSDGSFFLYSKLTVDKSRWQQGNVFSCSVMHEALHNHY

TQKSLSLSPGKGGGGGSGGGGSGGGGSGGGGSLPAPKNLVVSRVTEDSARLSWT

APDAAFDSFLIQYQESEKVGEAIVLTVPGSERSYDLTGLKPGTEYTVSIYGVSHGP

WYNYGEWRSNPLSAIFTT hcOX40SF2IgG2sigma_R2BS56_HC-C amino acid (hcOX40SF2IgG2sigma_HC +
linker + R2BS56 FN3 domain)

(SEQ ID NO: 38)
QVQLVQSGAEVKKPGSSVKVSCKASGYTFKDYTMHWVRQAPGQGLEWIGGIYP

NNGGSTYNQNFKDRVTLTADKSTSTAYMELSSLRSEDTAVYYCARMGYHGPHL

DFDVWGQGTTVTVSSASTKGPSVFPLAPCSRSTSESTAALGCLVKDYFPEPVTVS

WNSGALTSGVHTFPAVLQSSGLYSLSSVVTVPSSNFGTQTYTCNVDHKPSNTKVD

KTVERKCCVECPPCPAPPAAASSVFLFPPKPKDTLMISRTPEVTCVVVDVSAEDPE
```

-continued

VQFNWYVDGVEVHNAKTKPREEQFNSTFRVVSVLTVLHQDWLNGKEYKCKVSN

KGLPSSIEKTISKTKGQPREPQVYTLPPSREEMTKNQVSLTCLVKGFYPSDIAVEWE

SNGQPENNYKTTPPMLDSDGSFFLYSKLTVDKSRWQQGNVFSCSVMHEALHNHY

TQKSLSLSPGKGGGGGSGGGGSGGGGSGGGGSLPAPKNLVVSRVTEDSARLSWT

APDAAFDSFSIAYWEYRKGGEAIVLTVPGSERSYDLTGLKPGTEYFVLIYGVKGG

WQSKPLSAIFTT hcOX40SF2IgG2sigma_HC cDNA (SEQ ID NO: 46)

CAGGTGCAGCTGGTCCAGAGCGGAGCCGAGGTGAAGAAGCCCGGCTCCAGCG

TGAAGGTGAGCTGCAAGGCCAGCGGCTACACCTTCAAGGACTACACCATGCA

CTGGGTGAGACAGGCCCCTGGACAGGGCCTGGAATGGATCGGCGGCATCTAC

CCCAACAACGGCGGCTCCACCTACAACCAGAACTTCAAGGACAGGGTGACCC

TGACCGCCGACAAGAGCACCAGCACCGCTTACATGGAGCTGAGCAGCCTGAG

GAGCGAGGACACCGCCGTGTACTACTGCGCCAGGATGGGCTACCACGGCCCTC

ACCTGGACTTCGACGTGTGGGGCCAGGGCACCACCGTGACAGTGAGCTCCGCC

TCCACCAAGGGCCCATCGGTCTTCCCCCTGGCGCCCTGCTCCAGGAGCACCTC

CGAGAGCACAGCCGCCCTGGGCTGCCTGGTCAAGGACTACTTCCCCGAACCGG

TGACGGTGTCGTGGAACTCAGGCGCTCTGACCAGCGGCGTGCACACCTTCCCA

GCTGTCCTACAGTCCTCAGGACTCTACTCCCTCAGCAGCGTGGTGACCGTGCC

CTCCAGCAACTTCGGCACCCAGACCTACACCTGCAACGTAGATCACAAGCCCA

GCAACACCAAGGTGGACAAGACAGTTGAGCGCAAATGTTGTGTCGAGTGCCC

ACCGTGCCCAGCACCACCTGCCGCAGCCAGCTCAGTCTTCCTCTTCCCCCCAA

AACCCAAGGACACCCTCATGATCTCCCGGACCCCTGAGGTCACGTGCGTGGTG

GTGGACGTGAGCGCCGAAGACCCCGAGGTCCAGTTCAACTGGTACGTGGACG

GCGTGGAGGTGCATAATGCCAAGACAAAGCCACGGGAGGAGCAGTTCAACAG

CACGTTCCGTGTGGTCAGCGTCCTCACCGTTCTGCACCAGGACTGGCTGAACG

GCAAGGAGTACAAGTGCAAGGTCTCCAACAAAGGCCTCCCATCCTCCATCGAG

AAAACCATCTCCAAAACCAAAGGGCAGCCCCGAGAACCACAGGTGTACACCC

TGCCCCCATCCCGGGAGGAGATGACCAAGAACCAGGTCAGCCTGACCTGCCTG

GTCAAAGGCTTCTACCCCAGCGACATCGCCGTGGAGTGGGAGAGCAATGGGC

AGCCGGAGAACAACTACAAGACCACACCTCCCATGCTGGACTCCGACGGCTCC

TTCTTCCTCTACAGCAAGCTCACCGTGGACAAGAGCAGGTGGCAGCAGGGGA

ACGTCTTCTCATGCTCCGTGATGCATGAGGCTCTGCACAACCACTACACGCAG

AAGAGCCTCTCCCTGTCTCCGGGTAAA

OX40SF2_LC cDNA (SEQ ID NO: 47)

GACATCCAGATGACCCAGAGCCCTAGCAGCCTGAGCGCTAGCGTGGGCGACA

GAGTGACCATCACCTGCAAGGCCAGCCAGGATGTGGGAGCCGCCGTGGCCTG

GTATCAGCAGAAGCCCGGAAAGGCCCCCAAGCTGCTGATCTACTGGGCCAGC

ACCAGACACACCGGCGTGCCTAGCAGGTTTAGCGGCAGCGGCAGCGGCACCG

ACTTTACCCTGACCATCAGCAGCCTGCAGCCCGAGGATTTCGCCACCTACTAC

TGCCAGCAGTACATCAACTACCCCCTGACCTTCGGCGGCGGCACCAAAGTGGA

-continued

GATCAAGCGTACGGTGGCTGCACCATCTGTCTTCATCTTCCCGCCATCTGATGA

GCAGTTGAAATCTGGAACTGCCTCTGTTGTGTGCCTGCTGAATAACTTCTATCC

CAGAGAGGCCAAAGTACAGTGGAAGGTGGATAACGCCCTCCAATCGGGTAAC

TCCCAGGAGAGTGTCACAGAGCAGGACAGCAAGGACAGCACCTACAGCCTCA

GCAGCACCCTGACGCTGAGCAAAGCAGACTACGAGAAACACAAAGTCTACGC

CTGCGAAGTCACCCATCAGGGCCTGAGCTCGCCCGTCACAAAGAGCTTCAACA

GGGGAGAGTGT hcOX40SF2IgG2sigma_R2BS6_HC-C cDNA    (SEQ ID NO: 48)

CAGGTGCAGCTGGTCCAGAGCGGAGCCGAGGTGAAGAAGCCCGGCTCCAGCG

TGAAGGTGAGCTGCAAGGCCAGCGGCTACACCTTCAAGGACTACACCATGCA

CTGGGTGAGACAGGCCCCTGGACAGGGCCTGGAATGGATCGGCGGCATCTAC

CCCAACAACGGCGGCTCCACCTACAACCAGAACTTCAAGGACAGGGTGACCC

TGACCGCCGACAAGAGCACCAGCACCGCTTACATGGAGCTGAGCAGCCTGAG

GAGCGAGGACACCGCCGTGTACTACTGCGCCAGGATGGGCTACCACGGCCCTC

ACCTGGACTTCGACGTGTGGGGCCAGGGCACCACCGTGACAGTGAGCTCCGCC

TCCACCAAGGGCCCATCGGTCTTCCCCCTGGCGCCCTGCTCCAGGAGCACCTC

CGAGAGCACAGCCGCCCTGGGCTGCCTGGTCAAGGACTACTTCCCCGAACCGG

TGACGGTGTCGTGGAACTCAGGCGCTCTGACCAGCGGCGTGCACACCTTCCCA

GCTGTCCTACAGTCCTCAGGACTCTACTCCCTCAGCAGCGTGGTGACCGTGCC

CTCCAGCAACTTCGGCACCCAGACCTACACCTGCAACGTAGATCACAAGCCCA

GCAACACCAAGGTGGACAAGACAGTTGAGCGCAAATGTTGTGTCGAGTGCCC

ACCGTGCCCAGCACCACCTGCCGCAGCCAGCTCAGTCTTCCTCTTCCCCCCAA

AACCCAAGGACACCCTCATGATCTCCCGGACCCCTGAGGTCACGTGCGTGGTG

GTGGACGTGAGCGCCGAAGACCCCGAGGTCCAGTTCAACTGGTACGTGGACG

GCGTGGAGGTGCATAATGCCAAGACAAAGCCACGGGAGGAGCAGTTCAACAG

CACGTTCCGTGTGGTCAGCGTCCTCACCGTTCTGCACCAGGACTGGCTGAACG

GCAAGGAGTACAAGTGCAAGGTCTCCAACAAAGGCCTCCCATCCTCCATCGAG

AAAACCATCTCCAAAACCAAAGGGCAGCCCCGAGAACCACAGGTGTACACCC

TGCCCCCATCCCGGAGGAGATGACCAAGAACCAGGTCAGCCTGACCTGCCTG

GTCAAAGGCTTCTACCCCAGCGACATCGCCGTGGAGTGGGAGAGCAATGGGC

AGCCGGAGAACAACTACAAGACCACACCTCCCATGCTGGACTCCGACGGCTCC

TTCTTCCTCTACAGCAAGCTCACCGTGGACAAGAGCAGGTGGCAGCAGGGGA

ACGTCTTCTCATGCTCCGTGATGCATGAGGCTCTGCACAACCACTACACGCAG

AAGAGCCTCTCCCTGTCTCCGGGTAAAGGAGGCGGAGGGAGTGGCGGGGGAG

GCTCTGGCGGCGGAGGATCCGGCGGCGGAGGAAGCCTGCCGGCGCCGAAAA

CCTGGTTGTTTCTCGTGTTACCGAAGACTCTGCGCGTCTGTCTTGGACCGCGCC

GGACGCGGCGTTCGACTCTTTCCTGATCCAGTACCAGGAATCTGAAAAAGTTG

GTGAAGCGATCGTGCTGACCGTTCCGGGTTCTGAACGTTCTTACGACCTGACC

GGTCTGAAACCGGGTACCGAATACACCGTTTCTATCTACGGTGTTCAATATGC

GGCGTGGTATCTGCCGCGTCACCACGAGGCGAGCAACCCGCTGTCTGCGATCT

TCACCACC hcOX40SF2IgG2sigma_R2BS9_HC-C cDNA (SEQ ID NO: 49)

CAGGTGCAGCTGGTCCAGAGCGGAGCCGAGGTGAAGAAGCCCGGCTCCAGCG

TGAAGGTGAGCTGCAAGGCCAGCGGCTACACCTTCAAGGACTACACCATGCA

CTGGGTGAGACAGGCCCCTGGACAGGGCCTGGAATGGATCGGCGGCATCTAC

CCCAACAACGGCGGCTCCACCTACAACCAGAACTTCAAGGACAGGGTGACCC

TGACCGCCGACAAGAGCACCAGCACCGCTTACATGGAGCTGAGCAGCCTGAG

GAGCGAGGACACCGCCGTGTACTACTGCGCCAGGATGGGCTACCACGGCCCTC

ACCTGGACTTCGACGTGTGGGGCCAGGGCACCACCGTGACAGTGAGCTCCGCC

TCCACCAAGGGCCCATCGGTCTTCCCCCTGGCGCCCTGCTCCAGGAGCACCTC

CGAGAGCACAGCCGCCCTGGGCTGCCTGGTCAAGGACTACTTCCCCGAACCGG

TGACGGTGTCGTGGAACTCAGGCGCTCTGACCAGCGGCGTGCACACCTTCCCA

GCTGTCCTACAGTCCTCAGGACTCTACTCCCTCAGCAGCGTGGTGACCGTGCC

CTCCAGCAACTTCGGCACCCAGACCTACACCTGCAACGTAGATCACAAGCCCA

GCAACACCAAGGTGGACAAGACAGTTGAGCGCAAATGTTGTGTCGAGTGCCC

ACCGTGCCCAGCACCACCTGCCGCAGCCAGCTCAGTCTTCCTCTTCCCCCCAA

AACCCAAGGACACCCTCATGATCTCCCGGACCCCTGAGGTCACGTGCGTGGTG

GTGGACGTGAGCGCCGAAGACCCCGAGGTCCAGTTCAACTGGTACGTGGACG

GCGTGGAGGTGCATAATGCCAAGACAAAGCCACGGGAGGAGCAGTTCAACAG

CACGTTCCGTGTGGTCAGCGTCCTCACCGTTCTGCACCAGGACTGGCTGAACG

GCAAGGAGTACAAGTGCAAGGTCTCCAACAAAGGCCTCCCATCCTCCATCGAG

AAAACCATCTCCAAAACCAAAGGGCAGCCCCGAGAACCACAGGTGTACACCC

TGCCCCCATCCCGGGAGGAGATGACCAAGAACCAGGTCAGCCTGACCTGCCTG

GTCAAAGGCTTCTACCCCAGCGACATCGCCGTGGAGTGGGAGAGCAATGGGC

AGCCGGAGAACAACTACAAGACCACACCTCCCATGCTGGACTCCGACGGCTCC

TTCTTCCTCTACAGCAAGCTCACCGTGGACAAGAGCAGGTGGCAGCAGGGGA

ACGTCTTCTCATGCTCCGTGATGCATGAGGCTCTGCACAACCACTACACGCAG

AAGAGCCTCTCCCTGTCTCCGGGTAAAGGAGGCGGAGGGAGTGGCGGGGGAG

GCTCTGGCGGCGGAGGATCCGGCGGCGGAGGAAGCCTGCCGGCGCCGAAAAA

CCTGGTTGTTTCTCGTGTTACCGAAGACTCTGCGCGTCTGTCTTGGACCGCGCC

GGACGCGGCGTTCGACTCTTTCTGGATTTATTACCTGGAGTATTGGCGTGGCG

GTGAAGCGATCGTTCTGACCGTTCCGGGTTCTGAACGTTCTTACGACCTGACC

GGTCTGAAACCGGGTACCGAATATTTCGTTCAAATTCACGGCGTTAAGGGCGG

TCAATATAGTTATCCACTGTCTGCGATCTTCACCACC hcOX40SF2IgG2sigma_R2BS12_HC-C cDNA (SEQ ID NO: 50)

CAGGTGCAGCTGGTCCAGAGCGGAGCCGAGGTGAAGAAGCCCGGCTCCAGCG

TGAAGGTGAGCTGCAAGGCCAGCGGCTACACCTTCAAGGACTACACCATGCA

CTGGGTGAGACAGGCCCCTGGACAGGGCCTGGAATGGATCGGCGGCATCTAC

CCCAACAACGGCGGCTCCACCTACAACCAGAACTTCAAGGACAGGGTGACCC

TGACCGCCGACAAGAGCACCAGCACCGCTTACATGGAGCTGAGCAGCCTGAG

GAGCGAGGACACCGCCGTGTACTACTGCGCCAGGATGGGCTACCACGGCCCTC

-continued

```
ACCTGGACTTCGACGTGTGGGCCAGGGCACCACCGTGACAGTGAGCTCCGCC
TCCACCAAGGGCCCATCGGTCTTCCCCCTGGCGCCCTGCTCCAGGAGCACCTC
CGAGAGCACAGCCGCCCTGGGCTGCCTGGTCAAGGACTACTTCCCCGAACCGG
TGACGGTGTCGTGGAACTCAGGCGCTCTGACCAGCGGCGTGCACACCTTCCCA
GCTGTCCTACAGTCCTCAGGACTCTACTCCCTCAGCAGCGTGGTGACCGTGCC
CTCCAGCAACTTCGGCACCCAGACCTACACCTGCAACGTAGATCACAAGCCCA
GCAACACCAAGGTGGACAAGACAGTTGAGCGCAAATGTTGTGTCGAGTGCCC
ACCGTGCCCAGCACCACCTGCCGCAGCCAGCTCAGTCTTCCTCTTCCCCCCAA
AACCCAAGGACACCCTCATGATCTCCCGGACCCCTGAGGTCACGTGCGTGGTG
GTGGACGTGAGCGCCGAAGACCCCGAGGTCCAGTTCAACTGGTACGTGGACG
GCGTGGAGGTGCATAATGCCAAGACAAAGCCACGGGAGGAGCAGTTCAACAG
CACGTTCCGTGTGGTCAGCGTCCTCACCGTTCTGCACCAGGACTGGCTGAACG
GCAAGGAGTACAAGTGCAAGGTCTCCAACAAAGGCCTCCCATCCTCCATCGAG
AAAACCATCTCCAAAACCAAAGGGCAGCCCCGAGAACCACAGGTGTACACCC
TGCCCCCATCCCGGGAGGAGATGACCAAGAACCAGGTCAGCCTGACCTGCCTG
GTCAAAGGCTTCTACCCCAGCGACATCGCCGTGGAGTGGGAGAGCAATGGGC
AGCCGGAGAACAACTACAAGACCACACCTCCCATGCTGGACTCCGACGGCTCC
TTCTTCCTCTACAGCAAGCTCACCGTGGACAAGAGCAGGTGGCAGCAGGGGA
ACGTCTTCTCATGCTCCGTGATGCATGAGGCTCTGCACAACCACTACACGCAG
AAGAGCCTCTCCCTGTCTCCGGGTAAAGGAGGCGGAGGGAGTGGCGGGGGAG
GCTCTGGCGGCGGAGGATCCGGCGGCGGAGGAAGCCTGCCGGCGCCGAAAAA
CCTGGTTGTTTCTCGTGTTACCGAAGACTCTGCGCGTCTGTCTTGGACCGCGCC
GGACGCGGCGTTCGACTCTTTTCTGATCGCGTATGCGGAATATTGGGAGGGCG
GTGAAGCGGTCGTTCTGACCGTTCCGGGTTCTGAACGTTCTTACGACCTGACC
GGTCTGAAACCGGGTACCGAATATTTCGTTCAAATCAATGGCGTTAAGGGTGG
TTTCTGGAGTATCCCACTGTCTGCGATCTTCACCACC
hcOX40SF2IgG2sigma_R2BS26_HC-C cDNA                              (SEQ ID NO: 51)
CAGGTGCAGCTGGTCCAGAGCGGAGCCGAGGTGAAGAAGCCCGGCTCCAGCG
TGAAGGTGAGCTGCAAGGCCAGCGGCTACACCTTCAAGGACTACACCATGCA
CTGGGTGAGACAGGCCCCTGGACAGGGCCTGGAATGGATCGGCGGCATCTAC
CCCAACAACGGCGGCTCCACCTACAACCAGAACTTCAAGGACAGGGTGACCC
TGACCGCCGACAAGAGCACCAGCACCGCTTACATGGAGCTGAGCAGCCTGAG
GAGCGAGGACACCGCCGTGTACTACTGCGCCAGGATGGGCTACCACGGCCCTC
ACCTGGACTTCGACGTGTGGGCCAGGGCACCACCGTGACAGTGAGCTCCGCC
TCCACCAAGGGCCCATCGGTCTTCCCCCTGGCGCCCTGCTCCAGGAGCACCTC
CGAGAGCACAGCCGCCCTGGGCTGCCTGGTCAAGGACTACTTCCCCGAACCGG
TGACGGTGTCGTGGAACTCAGGCGCTCTGACCAGCGGCGTGCACACCTTCCCA
GCTGTCCTACAGTCCTCAGGACTCTACTCCCTCAGCAGCGTGGTGACCGTGCC
CTCCAGCAACTTCGGCACCCAGACCTACACCTGCAACGTAGATCACAAGCCCA
GCAACACCAAGGTGGACAAGACAGTTGAGCGCAAATGTTGTGTCGAGTGCCC
ACCGTGCCCAGCACCACCTGCCGCAGCCAGCTCAGTCTTCCTCTTCCCCCCAA
```

-continued

```
AACCCAAGGACACCCTCATGATCTCCCGGACCCCTGAGGTCACGTGCGTGGTG
GTGGACGTGAGCGCCGAAGACCCCGAGGTCCAGTTCAACTGGTACGTGGACG
GCGTGGAGGTGCATAATGCCAAGACAAAGCCACGGGAGGAGCAGTTCAACAG
CACGTTCCGTGTGGTCAGCGTCCTCACCGTTCTGCACCAGGACTGGCTGAACG
GCAAGGAGTACAAGTGCAAGGTCTCCAACAAAGGCCTCCCATCCTCCATCGAG
AAAACCATCTCCAAAACCAAAGGGCAGCCCCGAGAACCACAGGTGTACACCC
TGCCCCCATCCCGGGAGGAGATGACCAAGAACCAGGTCAGCCTGACCTGCCTG
GTCAAAGGCTTCTACCCCAGCGACATCGCCGTGGAGTGGGAGAGCAATGGGC
AGCCGGAGAACAACTACAAGACCACACCTCCCATGCTGGACTCCGACGGCTCC
TTCTTCCTCTACAGCAAGCTCACCGTGGACAAGAGCAGGTGGCAGCAGGGGA
ACGTCTTCTCATGCTCCGTGATGCATGAGGCTCTGCACAACCACTACACGCAG
AAGAGCCTCTCCCTGTCTCCGGGTAAAGGAGGCGGAGGGAGTGGCGGGGGAG
GCTCTGGCGGCGGAGGATCCGGCGGCGGAGGAAGCCTGCCGGCGCCGAAAAA
CCTGGTTGTTTCTCGTGTTACCGAAGACTCTGCGCGTCTGTCTTGGACCGCGCC
GGACGCGGCGTTCGACTCTTTTCCGATCGCGTATATCGAGTATTGGACTGGCG
GTGAAGCGATCGTTCTGACCGTTCCGGGTTCTGAACGTTCTTACGACCTGACC
GGTCTGAAACCGGGTACCGAATATTTCGTTTGGATTCACGGCGTTAAGGGTGG
TGCGTGGTCCAGCCCGCTGTCTGCGATCTTCACCACC
hcOX40SF2IgG2sigma_R2BS29_HC-C cDNA
                                                           (SEQ ID NO: 52)
CAGGTGCAGCTGGTCCAGAGCGGAGCCGAGGTGAAGAAGCCCGGCTCCAGCG
TGAAGGTGAGCTGCAAGGCCAGCGGCTACACCTTCAAGGACTACACCATGCA
CTGGGTGAGACAGGCCCCTGGACAGGGCCTGGAATGGATCGGCGGCATCTAC
CCCAACAACGGCGGCTCCACCTACAACCAGAACTTCAAGGACAGGGTGACCC
TGACCGCCGACAAGAGCACCAGCACCGCTTACATGGAGCTGAGCAGCCTGAG
GAGCGAGGACACCGCCGTGTACTACTGCGCCAGGATGGGCTACCACGGCCCTC
ACCTGGACTTCGACGTGTGGGGCCAGGGCACCACCGTGACAGTGAGCTCCGCC
TCCACCAAGGGCCCATCGGTCTTCCCCCTGGCGCCCTGCTCCAGGAGCACCTC
CGAGAGCACAGCCGCCCTGGGCTGCCTGGTCAAGGACTACTTCCCCGAACCGG
TGACGGTGTCGTGGAACTCAGGCGCTCTGACCAGCGGCGTGCACACCTTCCCA
GCTGTCCTACAGTCCTCAGGACTCTACTCCCTCAGCAGCGTGGTGACCGTGCC
CTCCAGCAACTTCGGCACCCAGACCTACACCTGCAACGTAGATCACAAGCCCA
GCAACACCAAGGTGGACAAGACAGTTGAGCGCAAATGTTGTGTCGAGTGCCC
ACCGTGCCCAGCACCACCTGCCGCAGCCAGCTCAGTCTTCCTCTTCCCCCCAA
AACCCAAGGACACCCTCATGATCTCCCGGACCCCTGAGGTCACGTGCGTGGTG
GTGGACGTGAGCGCCGAAGACCCCGAGGTCCAGTTCAACTGGTACGTGGACG
GCGTGGAGGTGCATAATGCCAAGACAAAGCCACGGGAGGAGCAGTTCAACAG
CACGTTCCGTGTGGTCAGCGTCCTCACCGTTCTGCACCAGGACTGGCTGAACG
GCAAGGAGTACAAGTGCAAGGTCTCCAACAAAGGCCTCCCATCCTCCATCGAG
AAAACCATCTCCAAAACCAAAGGGCAGCCCCGAGAACCACAGGTGTACACCC
TGCCCCCATCCCGGGAGGAGATGACCAAGAACCAGGTCAGCCTGACCTGCCTG
```

-continued

GTCAAAGGCTTCTACCCCAGCGACATCGCCGTGGAGTGGGAGAGCAATGGGC

AGCCGGAGAACAACTACAAGACCACACCTCCCATGCTGGACTCCGACGGCTCC

TTCTTCCTCTACAGCAAGCTCACCGTGGACAAGAGCAGGTGGCAGCAGGGGA

ACGTCTTCTCATGCTCCGTGATGCATGAGGCTCTGCACAACCACTACACGCAG

AAGAGCCTCTCCCTGTCTCCGGGTAAAGGAGGCGGAGGGAGTGGCGGGGGAG

GCTCTGGCGGCGGAGGATCCGGCGGCGGAGGAAGCCTGCCCGCCCCCAAGAA

CCTGGTGGTGAGCAGGGTGACCGAGGACAGCGCCAGGCTGAGCTGGACAGCT

CCTGACGCCGCCTTCGACAGCTTCCCCATCTATTACTGGGAGTACAGGGTGGG

CGGAGAGGCCATCGTGCTGACAGTGCCCGGCAGCGAGAGGAGCTACGACCTG

ACCGGCCTGAAGCCTGGCACCGAGTACTTCGTGTACATCAACGGCGTGAAGGG

CGGCGAGGAATCCAGACCCCTGAGCGCCATCTTCACCACC hcOX40SF2IgG2sigma_R2BS39_HC-C cDNA (SEQ ID NO: 53)

CAGGTGCAGCTGGTCCAGAGCGGAGCCGAGGTGAAGAAGCCCGGCTCCAGCG

TGAAGGTGAGCTGCAAGGCCAGCGGCTACACCTTCAAGGACTACACCATGCA

CTGGGTGAGACAGGCCCCTGGACAGGGCCTGGAATGGATCGGCGGCATCTAC

CCCAACAACGGCGGCTCCACCTACAACCAGAACTTCAAGGACAGGGTGACCC

TGACCGCCGACAAGAGCACCAGCACCGCTTACATGGAGCTGAGCAGCCTGAG

GAGCGAGGACACCGCCGTGTACTACTGCGCCAGGATGGGCTACCACGGCCCTC

ACCTGGACTTCGACGTGTGGGGCCAGGGCACCACCGTGACAGTGAGCTCCGCC

TCCACCAAGGGCCCATCGGTCTTCCCCCTGGCGCCCTGCTCCAGGAGCACCTC

CGAGAGCACAGCCGCCCTGGGCTGCCTGGTCAAGGACTACTTCCCCGAACCGG

TGACGGTGTCGTGGAACTCAGGCGCTCTGACCAGCGGCGTGCACACCTTCCCA

GCTGTCCTACAGTCCTCAGGACTCTACTCCCTCAGCAGCGTGGTGACCGTGCC

CTCCAGCAACTTCGGCACCCAGACCTACACCTGCAACGTAGATCACAAGCCCA

GCAACACCAAGGTGGACAAGACAGTTGAGCGCAAATGTTGTGTCGAGTGCCC

ACCGTGCCCAGCACCACCTGCCGCAGCCAGCTCAGTCTTCCTCTTCCCCCCAA

AACCCAAGGACACCCTCATGATCTCCCGGACCCCTGAGGTCACGTGCGTGGTG

GTGGACGTGAGCGCCGAAGACCCCGAGGTCCAGTTCAACTGGTACGTGGACG

GCGTGGAGGTGCATAATGCCAAGACAAAGCCACGGGAGGAGCAGTTCAACAG

CACGTTCCGTGTGGTCAGCGTCCTCACCGTTCTGCACCAGGACTGGCTGAACG

GCAAGGAGTACAAGTGCAAGGTCTCCAACAAAGGCCTCCCATCCTCCATCGAG

AAAACCATCTCCAAAACCAAAGGGCAGCCCCGAGAACCACAGGTGTACACCC

TGCCCCCATCCCGGGAGGAGATGACCAAGAACCAGGTCAGCCTGACCTGCCTG

GTCAAAGGCTTCTACCCCAGCGACATCGCCGTGGAGTGGGAGAGCAATGGGC

AGCCGGAGAACAACTACAAGACCACACCTCCCATGCTGGACTCCGACGGCTCC

TTCTTCCTCTACAGCAAGCTCACCGTGGACAAGAGCAGGTGGCAGCAGGGGA

ACGTCTTCTCATGCTCCGTGATGCATGAGGCTCTGCACAACCACTACACGCAG

AAGAGCCTCTCCCTGTCTCCGGGTAAAGGAGGCGGAGGGAGTGGCGGGGGAG

GCTCTGGCGGCGGAGGATCCGGCGGCGGAGGAAGCCTGCCGGCGCCGAAAAA

CCTGGTTGTTTCTCGTGTTACCGAAGACTCTGCGCGTCTGTCTTGGACCGCGCC

GGACGCGGCGTTCGACTCTTTCCTGATCCAGTACCAGGAATCTGAAAAAGTTG

-continued

```
GTGAAGCGATCGTGCTGACCGTTCCGGGTTCTGAACGTTCTTACGACCTGACC

GGTCTGAAACCGGGTACCGAATACACCGTTTCTATCTACGGTGTGAGCCACGG

CCCGTGGTATAATTATGGCGAGTGGCGTTCTAACCCGCTGTCTGCGATCTTCAC

CACC hcOX40SF2IgG2sigma_R2BS56_HC-C cDNA

CAGGTGCAGCTGGTCCAGAGCGGAGCCGAGGTGAAGAAGCCCGGCTCCAGCG

TGAAGGTGAGCTGCAAGGCCAGCGGCTACACCTTCAAGGACTACACCATGCA

CTGGGTGAGACAGGCCCCTGGACAGGGCCTGGAATGGATCGGCGGCATCTAC

CCCAACAACGGCGGCTCCACCTACAACCAGAACTTCAAGGACAGGGTGACCC

TGACCGCCGACAAGAGCACCAGCACCGCTTACATGGAGCTGAGCAGCCTGAG

GAGCGAGGACACCGCCGTGTACTACTGCGCCAGGATGGGCTACCACGGCCCTC

ACCTGGACTTCGACGTGTGGGGCCAGGGCACCACCGTGACAGTGAGCTCCGCC

TCCACCAAGGGCCCATCGGTCTTCCCCCTGGCGCCCTGCTCCAGGAGCACCTC

CGAGAGCACAGCCGCCCTGGGCTGCCTGGTCAAGGACTACTTCCCCGAACCGG

TGACGGTGTCGTGGAACTCAGGCGCTCTGACCAGCGGCGTGCACACCTTCCCA

GCTGTCCTACAGTCCTCAGGACTCTACTCCCTCAGCAGCGTGGTGACCGTGCC

CTCCAGCAACTTCGGCACCCAGACCTACACCTGCAACGTAGATCACAAGCCCA

GCAACACCAAGGTGGACAAGACAGTTGAGCGCAAATGTTGTGTCGAGTGCCC

ACCGTGCCCAGCACCACCTGCCGCAGCCAGCTCAGTCTTCCTCTTCCCCCCAA

AACCCAAGGACACCCTCATGATCTCCCGGACCCCTGAGGTCACGTGCGTGGTG

GTGGACGTGAGCGCCGAAGACCCCGAGGTCCAGTTCAACTGGTACGTGGACG

GCGTGGAGGTGCATAATGCCAAGACAAAGCCACGGGAGGAGCAGTTCAACAG

CACGTTCCGTGTGGTCAGCGTCCTCACCGTTCTGCACCAGGACTGGCTGAACG

GCAAGGAGTACAAGTGCAAGGTCTCCAACAAAGGCCTCCCATCCTCCATCGAG

AAAACCATCTCCAAAACCAAAGGGCAGCCCCGAGAACCACAGGTGTACACCC

TGCCCCCATCCCGGGAGGAGATGACCAAGAACCAGGTCAGCCTGACCTGCCTG

GTCAAAGGCTTCTACCCCAGCGACATCGCCGTGGAGTGGGAGAGCAATGGGC

AGCCGGAGAACAACTACAAGACCACACCTCCCATGCTGGACTCCGACGGCTCC

TTCTTCCTCTACAGCAAGCTCACCGTGGACAAGAGCAGGTGGCAGCAGGGGA

ACGTCTTCTCATGCTCCGTGATGCATGAGGCTCTGCACAACCACTACACGCAG

AAGAGCCTCTCCCTGTCTCCGGGTAAAGGAGGCGGAGGGAGTGGCGGGGAG

GCTCTGGCGGCGGAGGATCCGGCGGCGGAGGAAGCCTGCCGGCGCCGAAAAA

CCTGGTTGTTTCTCGTGTTACCGAAGACTCTGCGCGTCTGTCTTGGACCGCGCC

GGACGCGGCGTTCGACTCTTTTAGCATTGCGTACTGGGAGTATCGTAAAGGCG

GTGAAGCGATCGTTCTGACCGTTCCGGGTTCTGAACGTTCTTACGACCTGACC

GGTCTGAAACCGGGTACCGAATATTTCGTTCTGATCTATGGTGTCAAGGGCGG

TTGGCAATCCAAACCACTGTCTGCGATCTTCACCACC
```

(SEQ ID NO: 54)

To express the mAbtyrins, the constructs expressing heavy chain and light chain were transiently transfected in Expi293F cells (Life Technologies) following the manufacturer's instructions. Briefly, Expi293F cells were co-transfected with expression constructs encoding the heavy chain (HC) and light chain (LC) of each IgG in a 1:3 ratios. After 5 days of expression at 37° C., supernatants were clarified by centrifugation and 0.2 µm filtration, and the mAbtyrins were purified by Protein A affinity chromatography. SDS-PAGE analysis of purified mAbtyrins revealed expected 170 kDa protein band at non-reducing (NR) condition and 60 kDa heavy chain and 25 kDa light chain protein bands at reducing (R) condition.

The aggregation states of mAbtyrins in solution were evaluated by Size Exclusion Chromatography. Briefly, mAbtyrins were injected onto a TSKgel G3SW column (Tosoh Bioscience LLC) and their sizes were resolved by chromatography. All mAbtyrins showed similar chromatography profiles with a protein peak eluted at about 16 minutes while the antibodies showed a protein peak eluted at about 17 minutes.

Example 3: Characterization of OX40-FcγRII mAbtyrins

The generated mAbtyrins were characterized for their binding to FcγR and agonistic activities. The parental OX40 antibody OX40SF2IgG2sigma was used as a comparator throughout assays.

Binding of mAbtyrins on FcγR Expressed on HEK293f Cells

Flow Cytometry Staining

Plasmids expressing cDNAs encoding human FcγRI (NM_000566) (SEQ ID NO: 44), FcγRIIA (NM_021642) (SEQ ID NO: 2), FcγRIIB (NM_004001) (SEQ ID NO: 3), and FcγRIIIA (NM_000569) (SEQ ID NO: 45) (Origene) were transiently transfected into Expi293F cells by Expi-Fectamine293 transfection kit (Life Technologies). Flow cytometry assays were performed 48 h after transfection. To confirm the expression of transfected Fc receptors, their specific antibodies, 10.1 (BD Pharmingen) for FcγRI, IV.3 (StemCell Technologies) for FcγRIIA, 2B6 (in house preparation) for FcγRIIB (Veri et al. (2007) *Immunology* 121: 392-404), and 3G8 (BD Pharmingen) for FcγRIIIA, were employed in flow cytometry staining as positive controls.

$2 \times 10^5$ cells per well were seeded in 96-well plate and blocked in BSA Stain Buffer (BD Biosciences, San Jose, USA) for 30 min at 4° C. Cells were incubated with test mAbtyrin on ice for 1.5 h at 4° C. After being washed twice with BSA stain buffer, the cells were incubated with R-PE labeled anti-human or anti-mouse IgG secondary antibody (Jackson Immunoresearch Laboratories) for 45 min at 4° C. The cells were washed twice in stain buffer and then resuspended in 150 μL of Stain Buffer containing 1:200 diluted DRAQ7 live/dead stain (Cell Signaling Technology, Danvers, USA). PE and DRAQ7 signals of the stained cells were detected by Miltenyi MACSQuant flow cytometer (Miltenyi Biotec, Auburn, USA) using B2 and B4 channel respectively. Live cells were gated on DRAQ7 exclusion and the geometric mean fluorescence signals were determined for at least 10,000 live events collected. FlowJo software (Tree Star) was used for analysis. Data was plotted as the logarithm of antibody concentration versus mean fluorescence signals. Nonlinear regression analysis was performed by GraphPad Prism 6 (GraphPad Software, Inc.) and $EC_{50}$ values were calculated.

mAbtyrins bound to HEK293F cells expressing FcγRIIA with an $EC_{50}$ value between about 90-700 ng/ml (Table 7) and to HEK293F cells expressing FcγRIIB with an $EC_{50}$ value between about 500-1900 ng/ml (Table 7). As expected, OX40SF2IgG2sigma did not show binding activity to either FcγRIIA or FcγRIIB. Binding for FcγRI and FcγRIIIA was not tested for these constructs.

FcγRI

SEQ ID NO: 44

MWFLTTLLLWVPVDGQVDTTKAVITLQPPWVSVFQEETVTLHCEVLHLPG

SSSTQWFLNGTATQTSTPSYRITSASVNDSGEYRCQRGLSGRSDPIQLEIH

RGWLLLQVSSRVFTEGEPLALRCHAWKDKLVYNVLYYRNGKAFKFFHWNS

NLTILKTNISHNGTYHCSGMGKHRYTSAGISVTVKELFPAPVLNASVTSPL

LEGNLVTLSCETKLLLQRPGLQLYFSFYMGSKTLRGRNTSSEYQILTARRE

DSGLYWCEAATEDGNVLKRSPELELQVLGLQLPTPVWFHVLFYLAVGIMFL

VNTVLWVTIRKELKRKKKWDLEISLDSGHEKKVISSLQEDRHLEEELKCQE

QKEEQLQEGVHRKEPQGAT

FcγRIIIA

SEQ ID NO: 45

MAEGTLWQILCVSSDAQPQTFEGVKGADPPTLPPGSFLPGPVLWWGSLAR

LQTEKSDEVSRKGNWWVTEMGGGAGERLFTSSCLVGLVPLGLRISLVTCP

LQCGIMWQLLLPTALLLLVSAGMRTEDLPKAVVFLEPQWYRVLEKDSVTL

KCQGAYSPEDNSTQWFHNESLISSQASSYFIDAATVDDSGEYRCQTNLSTL

SDPVQLEVHIGWLLLQAPRWVFKEEDPIHLRCHSWKNTALHKVTYLQNG

KGRKYFHHNSDFYIPKATLKDSGSYFCRGLFGSKNVSSETVNITITQGLAV

STISSFFPPGYQVSFCLVMVLLFAVDTGLYFSVKTNIRSSTRDWKDHKFKW

RKDPQDK

TABLE 7

| | EC50 (ng/ml) | |
|---|---|---|
| Construct | Binding to Expi293F FcγRIIA | Binding to Expi293F FcγRIIB |
| OX40SF2IgG2sigma_R2BS6_HC-C | 700 | 1565 |
| OX40SF2IgG2sigma_R2BS9_HC-C | 498 | 1512 |
| OX40SF2IgG2sigma_R2BS12_HC-C | 302 | 926 |
| OX40SF2IgG2sigma_R2BS26_HC-C | 323 | 1377 |
| OX40SF2IgG2sigma_R2BS29_HC-C | 91 | 512 |
| OX40SF2IgG2sigma_R2BS39_HC-C | 532 | 1869 |
| OX40SF2IgG2sigma_R2BS56_HC-C | 287 | 1047 |
| OX40SF2IgG2sigma | >10,000 | >10,000 |

Binding of mAbtyrins on Raji Cells

Raji cell is a cell line derived from B cells that express predominantly FcγRIIB. The binding of mAbtyrins on Raji cells were investigated by flow cytometry assay described for testing mAbtyrin binding to FcγR. Binding of the mAbtyrins were detected by flow cytometry using a PE-labeled Goat F(ab') against Human IgG(γ).

Table 8 shows the $EC_{50}$ values of binding and mean signals at antibody concentration of 10 μg/ml. All mAbtyrins studied showed dose-dependent increased binding to Raji cells while OX40SF2IgG2sigma demonstrated no binding. At the concentration of 10 μg/mL, all mAbtyrins showed at least 6-fold higher binding signals compared to OX40SF2IgG2sigma. Among the mAbtyrins, OX40SF2IgG2sigma_R2BS29 showed the most potent binding to Raji cells.

TABLE 8

| Construct | Binding to Raji cells EC$_{50}$ (ng/ml) | Binding to Raji cells mean signals at 10 µg/ml |
| --- | --- | --- |
| OX40SF2IgG2sigma_R2BS6_HC-C | >10,000 | 5377 |
| OX40SF2IgG2sigma_R2BS9_HC-C | >10,000 | 3258 |
| OX40SF2IgG2sigma_R2BS12_HC-C | >10,000 | 2606 |
| OX40SF2IgG2sigma_R2BS26_HC-C | >10,000 | 2291 |
| OX40SF2IgG2sigma_R2BS29_HC-C | 1442 | 11918 |
| OX40SF2IgG2sigma_R2BS39_HC-C | >10,000 | 8220 |
| OX40SF2IgG2sigma_R2BS56_HC-C | 9906 | 9123 |
| OX40SF2IgG2sigma | >10,000 | 330 |

Binding of mAbtyrins on HEK-Blue: OX40 Cells

The binding of mAbtyrins on OX40 expressed on cell surface were investigated by flow cytometry assay described for testing mAbtyrin binding to FcγR. A stable HEK-Blue reporter cell line expressing human OX40 (HEK-Blue: OX40) was established by transfection OX40 expression plasmid (pUNO1-hOX40) into HEK-Blue™ Null 1 cells engineered to express a secreted embryonic alkaline phosphatase (SEAP) reporter gene under the control of NF-κB-inducible promoter (IFN-β minimal promoter). mAbtyrins were incubated with HEK-Blue: OX40 cells and the binding was detected by flow cytometry using a PE-labeled Goat F(ab')$_2$ against Human IgG(γ).

All mAbtyrins studied showed comparable binding to HEK-Blue: OX40 when compared to OX40SF2IgG2sigma at 1 µg/m (Table 9).

TABLE 9

| Construct | Binding to HEK-Blue: OX40 cells (mean signal at 1 µg/ml) |
| --- | --- |
| OX40SF2IgG2sigma_R2BS6_HC-C | 10388 |
| OX40SF2IgG2sigma_R2BS9_HC-C | 8903 |
| OX40SF2IgG2sigma_R2BS12_HC-C | 9706 |
| OX40SF2IgG2sigma_R2BS26_HC-C | 10179 |
| OX40SF2IgG2sigma_R2BS29_HC-C | 9181 |
| OX40SF2IgG2sigma_R2BS39_HC-C | 9318 |
| OX40SF2IgG2sigma_R2BS56_HC-C | 16875 |
| OX40SF2IgG2sigma | 13946 |

Agonistic Activity of mAbtyrins

Agonistic activity of mAbtyrins were evaluated using HEK-Blue NF-κB reporter assay. Briefly, 1×10$^5$ HEK-Blue: OX40 cells resuspended in 200 µl culture media were aliquoted in each well of the 96-well assay plate and the OX40 ligand or mAbtyrins were added. To test the cross-linking effect, either 1 µl of protein G magnetic beads (Pierce) or 1×10$^5$ Raji cell was added in the same assay well. After incubation at 37° C. overnight, the agonistic activities of mAbtyrins were evaluated by the quantification of the induced secreted alkaline phosphatase (SEAP) reporter gene expression using Quanti-Blue detection kit (Invivogen). Briefly, 40 µl cell culture supernatant was mixed with 160 µl Quanti-Blue reagent and incubated at 37° C. until appropriate blue color developed. The OD at 650 nm was measured using a SpectraMax microplate reader (Molecular Devices, Sunnyvale, Calif.). The agonistic activity of mAbtyrins was normalized as percent activity relative to that induced by 1 µg/mL OX40 ligand.

OX40 ligand dose-dependently stimulated reporter gene expression from the established HEK-Blue: OX40 cell line, indicating functional expression of transfected OX40.

All tested mAbtyrins demonstrated weak crosslinking independent agonistic activities in HEL-Blue, similar to what was observed for OX40SF2IgG2sigma. Cross-linking with Raji cells boosted the agonistic activity of the tested mAbtyrins but had no effect on OX40SF2IgG2sigma. Blocking interaction of mAbtyrins OX40SF2IgG2sigma_R2BS9_HC-C and OX40SF2IgG2sigma_R2BS26_HC-C with FcγR using either FcγRIIB or FcγRIIA binding antibodies (2B6 and IV.3, respectively) or corresponding FN3 domains (R2B29 and R2BS26, respectively) reduced the agonistic activity of mAbtyrins. This indicated that the interaction of FcγRII FN3 domain and FcγR on Raji cells was required to boost the agonistic activity of mAbtyrins. Table 10 shows the agonistic activity of 1 µg/ml mAbtyrins with or without cross-linking with Raji cells expressed as percent activity relative to 1 µg/ml OX40 ligand as well as fold of agonism enhancement upon cross-linking Table 11 shows the agonistic activity of select mAbtyrins after pre-blocking with anti-FcγRII mAbs or the corresponding FN3 domains.

TABLE 10

| | % activity at 1 µg/ml | | fold of agonism enhancement upon crosslinking |
| --- | --- | --- | --- |
| Construct | Without Raji cells | With Raji cells | |
| OX40SF2IgG2sigma_R2BS6_HC-C | 4.8 | 83.5 | 17 |
| OX40SF2IgG2sigma_R2BS9_HC-C | 4.1 | 88.1 | 21 |
| OX40SF2IgG2sigma_R2BS12_HC-C | 3.1 | 96.3 | 31 |
| OX40SF2IgG2sigma_R2BS26_HC-C | 4.1 | 102.9 | 25 |
| OX40SF2IgG2sigma_R2BS29_HC-C | 5.9 | 86.0 | 15 |
| OX40SF2IgG2sigma_R2BS39_HC-C | 4.2 | 99.5 | 24 |
| OX40SF2IgG2sigma_R2BS56_HC-C | 6.9 | 106.7 | 15 |
| OX40SF2IgG2sigma | 3.2 | 2.2 | 1 |

TABLE 11

| | % activity at 1 µg/ml | | |
| --- | --- | --- | --- |
| mAbtyrin | without preblocking | preblocking by 2B6 + IV.3 | preblocking by corresponding FN3 domain |
| OX40SF2IgG2sigma_R2BS9_HC-C | 102.0 | 40.0 | 62.0 |
| OX40SF2IgG2sigma_R2BS26_HC-C | 110.0 | 25.0 | 25.0 |

Similar to Raji cells, Daudi cells are also derived from B cells and express predominantly FcγRIIB. OX40SF2IgG2sigma_R2BS29_HC-C demonstrated binding to Daudi cells. Cross-linking with Daudi cells boosted the agonistic activity of OX40SF2IgG2sigma_R2BS29_HC-C, indicating that FcγRII receptors on Daudi cells also provided the crosslinking activity to facilitate the agonism of mAbtyrins. Table 12 shows the agonistic activity of mAbtyrins with or without cross-linking using Daudi cells and fold of agonism enhancement upon cross-linking expressed as percent activity when compared to the OX40 ligand.

TABLE 12

| Construct | % activity at 1 μg/ml | | fold of agonism |
| --- | --- | --- | --- |
| | without Daudi cells | with Daudi cells | enhancement upon crosslinking |
| OX40SF2IgG2sigma | 1.0 | 1.4 | 1 |
| OX40SF2IgG2sigma_R2BS29_HC-C | 2.3 | 103.9 | 45 |

Effector Functions of mAbtyrins

ADCC and ADCP Activities of the Generated mAbtyrins were Evaluated.

ADCC Assay

The ADCC activities of mAbtyrins were evaluated by an ADCC reporter bioassay as instructed by the manufacturer (Promega). Briefly, 25,000 HEK-Blue: OX40 cells per well plated in a 96-well plate overnight were mixed with the engineered effector cells in which the activation of FcγRIIIA receptor leads to the expression of a luciferase reporter. mAbtyrins were added to the cells and incubated at 37° C. for 6 h. Then Bio-Glo luciferase reagent was added and the luciferase signals were quantitated by Envision. The ADCC activities of mAbtyrins were expressed as fold of activation of luciferase signals over that without test antibody added.

ADCP Assay

An OX40 target cell line expressing GFP was established by infection HEK-Blue: OX40 cells with a Turbo GFP transduction particle (Sigma Aldrich). Stable GFP-expressing cells were selected with puromycin. The human $CD14^+$ $CD16^+$ monocytes were isolated from PBMCs (Biologics Specialty) using a negative human monocyte enrichment kit without CD16 depletion (StemCell Technologies). Isolated monocytes were plated in X-VIVO-10 medium (Lonza) containing 10% FBS and macrophages were differentiated from monocytes by the addition of 25 ng/mL macrophage colony-stimulating factor (R&D Systems) for 7 days. IFNγ (50 ng/mL; R&D Systems) was added for the final 24 h of differentiation. For the ADCP assay, $1\times10^5$ cells/well differentiated macrophages were mixed with $0.25\times10^5$ cells/well GFP-expressing HEK-Blue: OX40 cells (4:1 ratio) in 200 μl medium (DMEM+10% FBS) in 96-well U-bottom plates. The test mAbtyrins were added and the plate was incubated in a 37° C. incubator for 24 h. Then the cells were detached using Accutase (Sigma) and resuspended in BSA Stain Buffer. Macrophages were stained with anti-CD11b and anti-CD14 antibodies (BD Biosciences) coupled to Alexa Fluor 647 (Invitrogen). GFP positive HEK-Blue: OX40 target cells and Alexa647 positive macrophages were identified by flow cytometry using Miltenyi MACSQuant flow cytometer (Miltenyi Biotec, Auburn, USA). The data were analyzed using FlowJo software (Tree Star) and ADCP-mediated cell killing was determined by measuring the reduction in GFP fluorescence using the following equation: Percentage of target cells killed=((Percentage of $GFP^+$, $CD11b^-$, $CD14^-$ cells with the lowest concentration of antibody)−(Percentage of $GFP^+$, $CD11b^-$, $CD14^-$ cells with the test concentration of antibody))/(Percentage of $GFP^+$, $CD11b^-$, $CD14^-$ cells with the lowest concentration of antibody)×100.

Results

Neither mAbtyrins nor OX40SF2IgG2sigma had ADCC activity due to an effector silent Fc. This data indicated that the FN3 domains identified had no interaction with FcγRIIIA and the addition of the FN3 to the C-terminus of the parental antibody had no effect on ADCC (data not shown). All tested mAbtyrins mediated significant ADCP of OX40 expressing cells, while OX40SF2IgG2sigma did not mediate ADCP. Table 13 shows the percentage of OX40 cells killed by 1 μg/ml test mAbtyrin in the ADCP assay. The ADCP activity of mAbtyrins was presumably mediated by the interaction of mAbtyrin with FcγRIIA on macrophages.

TABLE 13

| Construct | % OX40 cell killed by macrophages |
| --- | --- |
| OX40SF2IgG2sigma_R2BS6_HC-C | 82 |
| OX40SF2IgG2sigma_R2BS9_HC-C | 85 |
| OX40SF2IgG2sigma_R2BS12_HC-C | 92 |
| OX40SF2IgG2sigma_R2BS26_HC-C | 92 |
| OX40SF2IgG2sigma_R2BS29_HC-C | 88 |
| OX40SF2IgG2sigma_R2BS39_HC-C | 83 |
| OX40SF2IgG2sigma_R2BS56_HC-C | 91 |
| OX40SF2IgG2sigma | 12 |

Example 4: Generation and Characterization of mAbtyrins with Varying Configurations To assess whether positioning of the FcγRII FN3 domains affect mAbtyrin characteristics, R2BS29 FN3 domain was engineered at different positions into an anti-OX40 antibody. Besides attaching the FN3 domain at the C-terminus of the antibody heavy chain, mAbtyrins with FN3 domain at the C-terminus of light chain (LC-C constructs), N-terminus of light chain (LC-N) constructs or N-terminus of heavy chain (HC-N constructs) of OX40 antibody were generated. Mabtyrins were cloned as wild-type IgG1 or effector silent IgG2sigma. mAbtyrins were generated by transfecting heavy chain and light chain constructs in Expi293F cells followed by mAbtyrin purification by Protein A affinity chromatography. SDS-PAGE analysis of purified mAbtyrins revealed expected 170 kDa protein band at non-reducing (NR) condition.

Table 14 shows the generated mAbtyrins. mAbtyrins were characterized for their binding to FcγR, agonism, effector functions and T cell activation using assays described herein. OX40SF2IgG1 (HC SEQ ID NO: 39; LC SEQ ID NO: 31) or OX40SF2IgG2sigma (HC SEQ ID NO: 30; LC SEQ ID NO: 31) was used as a control in the assays.

TABLE 14

| mAbtyrin | Heavy Chain/Light chain pair |
| --- | --- |
| OX40SF2IgG2sigma_R2BS29_HC-N | hcOX40SF2IgG2sigma_R2BS29_HC-N (SEQ ID NO: 40) lcOX40SF2_LC (SEQ ID NO: 31) |

TABLE 14-continued

| mAbtyrin | Heavy Chain/Light chain pair |
|---|---|
| OX40SF2IgG2sigma_R2BS29_LC-N | hcOX40SF2IgG2sigma_HC (SEQ ID NO: 30) lcOX40SF2_R2BS29_LC-N (SEQ ID NO: 41) |
| OX40SF2IgG2sigma_R2BS29_LC-C | hcOX40SF2IgG2sigma_HC (SEQ ID NO: 30) lcOX40SF2_R2BS29_LC-C (SEQ ID NO: 42) |
| OX40SF2IgG1_R2BS29_HC-C | hcOX40SF2IgG1_R2BS29_HC-C (SEQ ID NO: 43) lcOX40SF2_LC (SEQ ID NO: 31) |
| OX40SF2IgG1_R2BS29_LC-C | hcOX40SF2IgG1_HC (SEQ ID NO: 39) lcOX40SF2_R2BS29_LC-C (SEQ ID NO: 42) |

```
hcOX40SF2IgG1_HC (OX40SF2 Fv + IgG1 constant domain)
                                                         (SEQ ID NO: 39)
QVQLVQSGAEVKKPGSSVKVSCKASGYTFKDYTMHWVRQAPGQGLEWIGGI

YPNNGGSTYNQNFKDRVTLTADKSTSTAYMELSSLRSEDTAVYYCARMGYH

GPHLDFDVWGQGTTVTVSSASTKGPSVFPLAPSSKSTSGGTAALGCLVKDYFP

EPVTVSWNSGALTSGVHTFPAVLQSSGLYSLSSVVTVPSSSLGTQTYICNVNH

KPSNTKVDKKVEPKSCDKTHTCPPCPAPELLGGPSVFLFPPKPKDTLMISRTPE

VTCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDK

SRWQQGNVFSCSVMHEALHNHYTQKSLSLSPGK hcOX40SF2IgG2sigma_R2BS29_HC-N (R2BS29 FN3 domain + linker +
OX40SF2IgG2sigma) (SEQ ID NO: 40):
LPAPKNLVVSRVTEDSARLSWTAPDAAFDSFPIYYWEYRVGGEAIVLTVPGSE

RSYDLTGLKPGTEYFVYINGVKGGEESRPLSAIFTTGGGGSGGGGSGGGGSGG

GGSQVQLVQSGAEVKKPGSSVKVSCKASGYTFKDYTMHWVRQAPGQGLEW

IGGIYPNNGGSTYNQNFKDRVTLTADKSTSTAYMELSSLRSEDTAVYYCARM

GYHGPHLDFDVWGQGTTVTVSSASTKGPSVFPLAPCSRSTSESTAALGCLVKD

YFPEPVTVSWNSGALTSGVHTFPAVLQSSGLYSLSSVVTVPSSNFGTQTYTCN

VDHKPSNTKVDKTVERKCCVECPPCPAPPAAASSVFLFPPKPKDTLMISRTPEV

TCVVVDVSAEDPEVQFNWYVDGVEVHNAKTKPREEQFNSTFRVVSVLTVLH

QDWLNGKEYKCKVSNKGLPSSIEKTISKTKGQPREPQVYTLPPSREEMTKNQV

SLTCLVKGFYPSDIAVEWESNGQPENNYKTTPPMLDSDGSFFLYSKLTVDKSR

WQQGNVFSCSVMHEALHNHYTQKSLSLSPGK lcOX40SF2_R2BS29_LC-N (R2BS29 FN3 domain + linker +
OX40SF2 light chain)
                                                         (SEQ ID NO: 41)
LPAPKNLVVSRVTEDSARLSWTAPDAAFDSFPIYYWEYRVGGEAIVLTVPGSE

RSYDLTGLKPGTEYFVYINGVKGGEESRPLSAIFTTGGGGSGGGGSGGGGSGG

GGSDIQMTQSPSSLSASVGDRVTITCKASQDVGAAVAWYQQKPGKAPKLLIY

WASTRHTGVPSRFSGSGSGTDFTLTISSLQPEDFATYYCQQYINYPLTFGGGTK

VEIKRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSF
```

NRGEC lcOX40SF2_R2BS29_LC-C (OX40SF2 light chain + linker + R2BS29 FN3 domain
(SEQ ID NO: 42)
DIQMTQSPSSLSASVGDRVTITCKASQDVGAAVAWYQQKPGKAPKLLIYWAS

TRHTGVPSRFSGSGSGTDFTLTISSLQPEDFATYYCQQYINYPLTFGGGTKVEIK

RTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRG

ECGGGGSGGGGSGGGGSGGGGSMLPAPKNLVVSRVTEDSARLSWTAPDAAF

DSFPIYYWEYRVGGEAIVLTVPGSERSYDLTGLKPGTEYFVYINGVKGGEESR

PLSAIFTT hcOX40SF2IgG1_R2BS29_HC-C (SF2IgG1 heavy chain + linker + R2BS29 FN3 domain
(SEQ ID NO: 43)
QVQLVQSGAEVKKPGSSVKVSCKASGYTFKDYTMHWVRQAPGQGLEWIGGI

YPNNGGSTYNQNFKDRVTLTADKSTSTAYMELSSLRSEDTAVYYCARMGYH

GPHLDFDVWGQGTTVTVSSASTKGPSVFPLAPSSKSTSGGTAALGCLVKDYFP

EPVTVSWNSGALTSGVHTFPAVLQSSGLYSLSSVVTVPSSSLGTQTYICNVNH

KPSNTKVDKKVEPKSCDKTHTCPPCPAPELLGGPSVFLFPPKPKDTLMISRTPE

VTCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDK

SRWQQGNVFSCSVMHEALHNHYTQKSLSLSPGKGGGGGSGGGGSGGGGSGG

GGSLPAPKNLVVSRVTEDSARLSWTAPDAAFDSFPIYYWEYRVGGEAIVLTVP

GSERSYDLTGLKPGTEYFVYINGVKGGEESRPLSAIFTT hcOX40SF2IgG1 cDNA
(SEQ ID NO: 55)
CAGGTGCAGCTGGTCCAGAGCGGAGCCGAGGTGAAGAAGCCCGGCTCCAGCG

TGAAGGTGAGCTGCAAGGCCAGCGGCTACACCTTCAAGGACTACACCATGCA

CTGGGTGAGACAGGCCCCTGGACAGGGCCTGGAATGGATCGGCGGCATCTAC

CCCAACAACGGCGGCTCCACCTACAACCAGAACTTCAAGGACAGGGTGACCC

TGACCGCCGACAAGAGCACCAGCACCGCTTACATGGAGCTGAGCAGCCTGAG

GAGCGAGGACACCGCCGTGTACTACTGCGCCAGGATGGGCTACCACGGCCCTC

ACCTGGACTTCGACGTGTGGGGCCAGGGCACCACCGTGACAGTGAGCTCCGCC

TCCACCAAGGGCCCATCGGTCTTCCCCCTGGCACCCTCCTCCAAGAGCACCTCT

GGGGGCACAGCGGCCCTGGGCTGCCTGGTCAAGGACTACTTCCCCGAACCGGT

GACGGTGTCGTGGAACTCAGGCGCCCTGACCAGCGGCGTGCACACCTTCCCGG

CTGTCCTACAGTCCTCAGGACTCTACTCCCTCAGCAGCGTGGTGACCGTGCCCT

CCAGCAGCTTGGGCACCCAGACCTACATCTGCAACGTGAATCACAAGCCCAGC

AACACCAAGGTGGACAAGAAAGTTGAGCCCAAATCTTGTGACAAAACTCACA

CATGCCCACCGTGCCCAGCACCTGAACTCCTGGGGGGACCGTCAGTCTTCCTC

TTCCCCCCAAAACCCAAGGACACCCTCATGATCTCCCGGACCCCTGAGGTCAC

ATGCGTGGTGGTGGACGTGAGCCACGAAGACCCTGAGGTCAAGTTCAACTGGT

ACGTGGACGGCGTGGAGGTGCATAATGCCAAGACAAAGCCGCGGGAGGAGCA

GTACAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCAGC

CCCCATCGAGAAAACCATCTCCAAAGCCAAAGGGCAGCCCCGAGAACCACAG

GTGTACACCCTGCCCCCATCCCGGGAGGAGATGACCAAGAACCAGGTCAGCCT

GACCTGCCTGGTCAAAGGCTTCTATCCCAGCGACATCGCCGTGGAGTGGGAGA

GCAATGGGCAGCCGGAGAACAACTACAAGACCACGCCTCCCGTGCTGGACTC

CGACGGCTCCTTCTTCCTCTACAGCAAGCTCACCGTGGACAAGAGCAGGTGGC

AGCAGGGGAACGTCTTCTCATGCTCCGTGATGCATGAGGCTCTGCACAACCAC

TACACGCAGAAGAGCCTCTCCCTGTCTCCGGGTAAA hcOX40SF2IgG2sigma_R2BS29_HC-N cDNA (SEQ ID NO: 56)

CTGCCCGCCCCCAAGAACCTGGTCGTCAGCAGAGTGACCGAGGACTCCGCCAG

ACTGAGCTGGACAGCCCCTGACGCCGCCTTCGATTCCTTCCCCATCTACTACTG

GGAGTACAGAGTGGGCGGAGAGGCCATCGTGCTGACCGTGCCTGGCTCCGAG

AGGTCCTACGACCTGACCGGCCTGAAGCCTGGCACCGAGTACTTCGTGTACAT

CAACGGCGTGAAGGGCGGAGAGGAGTCCAGACCCCTGAGCGCCATTTTCACC

ACAGGCGGCGGCGGCTCCGGCGGAGGCGGCTCCGGCGGAGGAGGAAGCGGC

GGCGGAGGGAGCCAAGTGCAGCTCGTGCAGTCCGGCGCTGAGGTGAAGAAAC

CTGGCTCCAGCGTCAAGGTGAGCTGCAAGGCCAGCGGCTACACCTTCAAGGAC

TACACCATGCACTGGGTGAGGCAAGCCCCTGGCCAAGGCCTGGAGTGGATCG

GAGGCATCTACCCCAACAACGGCGGCTCCACCTATAACCAGAATTTCAAGGAC

AGGGTGACCCTGACCGCCGACAAGAGCACCAGCACCGCCTACATGGAGCTGA

GCAGCCTGAGATCCGAGGACACCGCCGTGTACTACTGCGCCAGGATGGGCTAT

CACGGCCCCCACCTGGACTTTGACGTGTGGGGCCAGGGCACAACCGTCACCGT

GTCCAGCGCCTCCACCAAGGGCCCATCGGTCTTCCCCCTGGCGCCCTGCTCCA

GGAGCACCTCCGAGAGCACAGCCGCCCTGGGCTGCCTGGTCAAGGACTACTTC

CCCGAACCGGTGACGGTGTCGTGGAACTCAGGCGCTCTGACCAGCGGCGTGCA

CACCTTCCCAGCTGTCCTACAGTCCTCAGGACTCTACTCCCTCAGCAGCGTGGT

GACCGTGCCCTCCAGCAACTTCGGCACCCAGACCTACACCTGCAACGTAGATC

ACAAGCCCAGCAACACCAAGGTGGACAAGACAGTTGAGCGCAAATGTTGTGT

CGAGTGCCCACCGTGCCCAGCACCACCTGCCGCAGCCAGCTCAGTCTTCCTCT

TCCCCCCAAAACCCAAGGACACCCTCATGATCTCCCGGACCCCTGAGGTCACG

TGCGTGGTGGTGGACGTGAGCGCCGAAGACCCCGAGGTCCAGTTCAACTGGTA

CGTGGACGGCGTGGAGGTGCATAATGCCAAGACAAAGCCACGGGAGGAGCAG

TTCAACAGCACGTTCCGTGTGGTCAGCGTCCTCACCGTTCTGCACCAGGACTG

GCTGAACGGCAAGGAGTACAAGTGCAAGGTCTCCAACAAAGGCCTCCCATCC

TCCATCGAGAAAACCATCTCCAAAACCAAAGGGCAGCCCCGAGAACCACAGG

TGTACACCCTGCCCCCATCCCGGGAGGAGATGACCAAGAACCAGGTCAGCCTG

ACCTGCCTGGTCAAAGGCTTCTACCCCAGCGACATCGCCGTGGAGTGGGAGAG

CAATGGGCAGCCGGAGAACAACTACAAGACCACACCTCCCATGCTGGACTCC

GACGGCTCCTTCTTCCTCTACAGCAAGCTCACCGTGGACAAGAGCAGGTGGCA

GCAGGGGAACGTCTTCTCATGCTCCGTGATGCATGAGGCTCTGCACAACCACT

ACACGCAGAAGAGCCTCTCCCTGTCTCCGGGTAAA

1cOX40SF2_R2BS29_LC-N cDNA (SEQ ID NO: 57)

CTGCCTGCCCCCAAGAACCTGGTGGTGAGCAGAGTGACCGAGGATAGCGCCA

GACTGTCCTGGACAGCCCCCGATGCCGCCTTCGACTCCTTCCCCATCTATTACT

GGGAGTACAGGGTGGGAGGCGAGGCCATCGTGCTGACCGTGCCTGGCTCCGA

GAGGAGCTACGATCTGACCGGCCTGAAGCCCGGCACCGAGTACTTCGTGTACA

TCAACGGCGTCAAGGGAGGCGAGGAGAGCAGACCCCTGTCCGCCATCTTCAC

CACAGGAGGCGGCGGCAGCGGCGGCGGAGGCAGCGGCGGCGGAGGCTCCGG

CGGCGGCGGCAGCGATATCCAGATGACCCAGAGCCCCAGCTCCCTGTCCGCTA

GCGTGGGCGACAGAGTGACCATCACCTGCAAGGCTAGCCAGGACGTGGGCGC

TGCTGTGGCCTGGTATCAGCAGAAGCCCGGCAAGGCCCCCAAGCTGCTGATCT

ACTGGGCCTCCACAAGGCACACCGGAGTGCCCAGCAGATTTTCCGGCAGCGGC

AGCGGCACCGATTTCACCCTGACCATCAGCTCCCTGCAGCCCGAGGACTTCGC

CACCTACTACTGCCAGCAGTACATCAATTACCCCCTGACCTTCGGCGGAGGCA

CCAAGGTGGAGATCAAACGTACGGTGGCTGCACCATCTGTCTTCATCTTCCCG

CCATCTGATGAGCAGTTGAAATCTGGAACTGCCTCTGTTGTGTGCCTGCTGAAT

AACTTCTATCCCAGAGAGGCCAAAGTACAGTGGAAGGTGGATAACGCCCTCC

AATCGGGTAACTCCCAGGAGAGTGTCACAGAGCAGGACAGCAAGGACAGCAC

CTACAGCCTCAGCAGCACCCTGACGCTGAGCAAAGCAGACTACGAGAAACAC

AAAGTCTACGCCTGCGAAGTCACCCATCAGGGCCTGAGCTCGCCCGTCACAAA

GAGCTTCAACAGGGGAGAGTGT

1cOX40SF2_R2BS29_LC-C cDNA (SEQ ID NO: 58)

GACATCCAGATGACCCAGAGCCCCAGCAGCCTGTCTGCCAGCGTGGGCGACA

GAGTGACCATCACATGCAAGGCCAGCCAGGACGTGGGAGCCGCCGTGGCTTG

GTATCAGCAGAAGCCTGGCAAGGCCCCCAAGCTGCTGATCTACTGGGCCAGCA

CCAGACACACCGGCGTGCCCAGCAGATTTTCTGGCAGCGGCTCCGGCACCGAC

TTCACCCTGACAATCAGCTCCCTGCAGCCCGAGGACTTCGCCACCTACTACTG

CCAGCAGTACATCAACTACCCCCTGACCTTCGGCGGAGGCACCAAGGTGGAA

ATCAAGCGTACGGTGGCTGCACCATCTGTCTTCATCTTCCCGCCATCTGATGAG

CAGTTGAAATCTGGAACTGCCTCTGTTGTGTGCCTGCTGAATAACTTCTATCCC

AGAGAGGCCAAAGTACAGTGGAAGGTGGATAACGCCCTCCAATCGGGTAACT

CCCAGGAGAGTGTCACAGAGCAGGACAGCAAGGACAGCACCTACAGCCTCAG

CAGCACCCTGACGCTGAGCAAAGCAGACTACGAGAAACACAAAGTCTACGCC

TGCGAAGTCACCCATCAGGGCCTGAGCTCGCCCGTCACAAAGAGCTTCAACAG

GGGAGAGTGTGGCGGCGGCGGCAGCGGCGGCGGCGGCAGCGGCGGCGGCGG

CAGCGGCGGAGGAGGATCCATGCTGCCTGCCCCCAAGAACCTGGTGGTGAGC

AGGGTGACCGAGGACAGCGCCAGACTGAGCTGGACAGCTCCCGACGCCGCCT

-continued
```
TCGACTCCTTCCCCATCTACTACTGGGAGTACAGAGTGGGCGGCGAAGCCATT
GTGCTGACCGTGCCCGGCAGCGAGAGGAGCTACGACCTGACCGGCCTGAAGC
CCGGCACCGAGTACTTCGTGTACATCAACGGCGTGAAGGGCGGCGAAGAGAG
CAGGCCTCTGAGCGCCATCTTCACCACA hcOX40SF2IgG1_R2BS29_HC-C cDNA CAGGTGCAGCTGGTCCAGAGCGGAGCCGAGGTGAAGAAGCCCGGCTCCAGCG
TGAAGGTGAGCTGCAAGGCCAGCGGCTACACCTTCAAGGACTACACCATGCA
CTGGGTGAGACAGGCCCCTGGACAGGGCCTGGAATGGATCGGCGGCATCTAC
CCCAACAACGGCGGCTCCACCTACAACCAGAACTTCAAGGACAGGGTGACCC
TGACCGCCGACAAGAGCACCAGCACCGCTTACATGGAGCTGAGCAGCCTGAG
GAGCGAGGACACCGCCGTGTACTACTGCGCCAGGATGGGCTACCACGGCCCTC
ACCTGGACTTCGACGTGTGGGGCCAGGGCACCACCGTGACAGTGAGCTCCGCC
TCCACCAAGGGCCCATCGGTCTTCCCCCTGGCACCCTCCTCCAAGAGCACCTCT
GGGGGCACAGCGGCCCTGGGCTGCCTGGTCAAGGACTACTTCCCCGAACCGGT
GACGGTGTCGTGGAACTCAGGCGCCCTGACCAGCGGCGTGCACACCTTCCCGG
CTGTCCTACAGTCCTCAGGACTCTACTCCCTCAGCAGCGTGGTGACCGTGCCCT
CCAGCAGCTTGGGCACCCAGACCTACATCTGCAACGTGAATCACAAGCCCAGC
AACACCAAGGTGGACAAGAAAGTTGAGCCCAAATCTTGTGACAAAACTCACA
CATGCCCACCGTGCCCAGCACCTGAACTCCTGGGGGGACCGTCAGTCTTCCTC
TTCCCCCCAAAACCCAAGGACACCCTCATGATCTCCCGGACCCCTGAGGTCAC
ATGCGTGGTGGTGGACGTGAGCCACGAAGACCCTGAGGTCAAGTTCAACTGGT
ACGTGGACGGCGTGGAGGTGCATAATGCCAAGACAAAGCCGCGGGAGGAGCA
GTACAACAGCACGTACCGTGTGGTCAGCGTCCTCACCGTCCTGCACCAGGACT
GGCTGAATGGCAAGGAGTACAAGTGCAAGGTCTCCAACAAAGCCCTCCCAGC
CCCCATCGAGAAAACCATCTCCAAAGCCAAAGGGCAGCCCCGAGAACCACAG
GTGTACACCCTGCCCCCATCCCGGGAGGAGATGACCAAGAACCAGGTCAGCCT
GACCTGCCTGGTCAAAGGCTTCTATCCCAGCGACATCGCCGTGGAGTGGGAGA
GCAATGGGCAGCCGGAGAACAACTACAAGACCACGCCTCCCGTGCTGGACTC
CGACGGCTCCTTCTTCCTCTACAGCAAGCTCACCGTGGACAAGAGCAGGTGGC
AGCAGGGGAACGTCTTCTCATGCTCCGTGATGCATGAGGCTCTGCACAACCAC
TACACGCAGAAGAGCCTCTCCCTGTCTCCGGGTAAAGGAGGCGGAGGGAGTG
GCGGGGGAGGCTCTGGCGGCGGAGGATCCGGCGGCGGAGGAAGCCTGCCCGC
CCCCAAGAACCTGGTGGTGAGCAGGGTGACCGAGGACAGCGCCAGGCTGAGC
TGGACAGCTCCTGACGCCGCCTTCGACAGCTTCCCCATCTATTACTGGGAGTA
CAGGGTGGGCGGAGAGGCCATCGTGCTGACAGTGCCCGGCAGCGAGAGGAGC
TACGACCTGACCGGCCTGAAGCCTGGCACCGAGTACTTCGTGTACATCAACGG
CGTGAAGGGCGGCGAGGAATCCAGACCCCTGAGCGCCATCTTCACCACC
```

(SEQ ID NO: 59)

Binding of mAbtyrins on Fcγ Receptors Expressed on Expi293F Cells

The binding of OX40 mAb×R2BS29 centyrin on FcγRIIA, FcγRIIB, FcγRI and FcγRIIIA transiently expressed on Expi293F cells were investigated by flow cytometry assay described above. mAbtyrins with R2BS29 FN3 domain bound FcγRIIA and FcγRIIB regardless of positioning of the FN3 domain and showed no binding to FcγRI and FcγRIIIA. Table 15 shows the EC50 values of binding of the mAbtyrins to various FcγR expressed on Expi293F cells.

TABLE 15

| Construct | EC50 (ng/ml) Binding to Expi293F expressing | | | |
|---|---|---|---|---|
| | FcγRIIA | FcγRIIB | FcγRI | FcγRIIIA |
| OX40SF2IgG2sigma_R2BS29_HC-C | 66 | 1518 | >10,000 | >10,000 |
| OX40SF2IgG2sigma_R2BS29_LC-C | 54 | 941 | >10,000 | >10,000 |
| OX40SF2IgG2sigma_R2BS29_HC-N | 42 | 1006 | >10,000 | >10,000 |
| OX40SF2IgG2sigma_R2BS29_LC-N | 46 | 1020 | >10,000 | >10,000 |
| OX40SF2IgG2sigma | >10,000 | >10,000 | >10,000 | >10,000 |
| OX40SF2IgG1_R2BS29_HC-C | 63 | 968 | 586 | 448 |
| OX40SF2IgG1_R2BS29_LC-C | 66 | 1002 | 397 | 585 |
| OX40SF2IgG1 | 3301 | >10,000 | 494 | 339 |

Binding of mAbtyrins to Raji Cells and HEK-Blue: OX40 Cells

The generated mAbtyrins demonstrated binding to Raji cells regardless of positioning of the FN3 domain, whereas the parental effector silent mAb OX40SF2IgG2sigma demonstrated no binding. All mAbtyrins demonstrated binding to OX40 expressed on HEK-Blue:OX40 cells regardless of the position of the FN3 domain. Table 16 shows the EC50 values of binding. The potencies of binding for the mAbtyrins were comparable to the corresponding native antibodies, suggesting that the attachment of R2BS29 FN3 domain on the antibodies at various positions did not affect the antibodies recognizing their targets.

TABLE 16

| Construct | Binding to Raji cells EC50 (ng/ml) | Binding to HEK-Blue OX40 cells EC50 (ng/ml) |
|---|---|---|
| OX40SF2IgG2sigma_R2BS29_HC-C | 1444 | 548 |
| OX40SF2IgG2sigma_R2BS29_LC-C | 3435 | 196 |
| OX40SF2IgG2sigma_R2BS29_HC-N | 1204 | 161 |
| OX40SF2IgG2sigma_R2BS29_LC-N | 3368 | 431 |
| OX40SF2IgG2sigma | >10000 | 166 |
| OX40SF2IgG1_R2BS29_HC-C | 1271 | 193 |
| OX40SF2IgG1_R2BS29_LC-C | 3296 | 111 |
| OX40SF2IgG1 | >10000 | 229 |

Agonism of mAbtyrins

All generated mAbtyrins demonstrated weak cross-linking independent agonistic activities on HEK-Blue: OX40 cells. Cross-linking with protein G boosted agonistic activity of the mAbtyrins. Cross-linking with Raji cells boosted the agonistic activity of mAbtyrins with C-terminally coupled FN3 domain in either heavy or light chain. However, Raji cells did not significantly boost the agonistic activity of mAbtyrins in which the FN3 domain was positioned at the N-terminus of either the heavy or the light chain Agonism was observed with mAbtyrins cloned as wild-type IgG1 or effector silent IgG2sigma, indicating that the isotype has no effect on agonism of FcγRII FN3 domain containing mAbtyrins. Table 17 shows the EC50 values obtained in the assay.

TABLE 17

| Construct | % activity at 1 μg/ml | | |
|---|---|---|---|
| | without Raji cells | with Raji cells | with protein G beads |
| OX40SF2IgG2sigma_R2BS29_HC-C | 5 | 93 | 123 |
| OX40SF2IgG2sigma_R2BS29_LC-C | 10 | 76 | 135 |

TABLE 17-continued

| Construct | % activity at 1 μg/ml | | |
|---|---|---|---|
| | without Raji cells | with Raji cells | with protein G beads |
| OX40SF2IgG2sigma_R2BS29_HC-N | 7 | 7 | 140 |
| OX40SF2IgG2sigma_R2BS29_LC-N | 5 | 11 | 142 |
| OX40SF2IgG2sigma | 3 | 2 | 147 |
| OX40SF2IgG1_R2BS29_HC-C | 4 | 90 | 130 |
| OX40SF2IgG1_R2BS29_LC-C | 10 | 76 | 135 |
| OX40SF2IgG1 | 3 | 9 | 144 | mAbtyrin Effector Functions

ADCC, ADCP and CDC activities of mAbtyrins were evaluated. ADCC and ADCP was assessed using protocols described above.

CDC Assay

Complement-dependent cytotoxicity (CDC) activities of anti-OX40 antibodies were evaluated by a complement-mediated cell killing assay. Briefly, 100,000 HEK-Blue: OX40 cells were incubated with rabbit complement (Cedar Lane Labs) and test mAbtyrins in a 96-well plate for one hour. The activities of lactate dehydrogenase (LDH) released from the cytosol of lysed HEK-Blue: OX40 cells into the supernatant were quantitated by cytotoxicity detection kit (Roche). The complement-mediated cytotoxicities were expressed as percent cytotoxicity relative to that lysed by Triton X-100.

FN3 domains did not further influence ADCC activity of mAbtyrins. All effector silent IgG2sigma mAbtyrins demonstrated no ADCC and IgG1 mAbtyrins demonstrated comparable ADCC to OX40SF2IgG1. FN3 domains on mAbtyrins facilitated efficient ADCP of OX40 expressing cells regardless of their position on mAbtyrins. mAbtyrins cloned as effector silent IgG2sigma demonstrated robust ADCP whereas OX40SF2IgG2sigma demonstrated no ADCP. IgG1 mAbtyrins demonstrated comparable ADCP activities as OX40SF2IgG1 while mAbtyrin in which the FN3 domain was located at the C-terminus of the light chain had somewhat improved potency when compared to OX40SF2IgG1. The FN3 domains on mAbtyrins had no effect on CDC when compared to OX40SF2IgG2sigma OX40SF2IgG1. Table 18 shows the degree of ADCC, CDC and ADCP for each tested mAbtyrin.

TABLE 18

| Construct | ADCC (fold activation) at 1 μg/ml | CDC (% cyto-toxicity) at 1 μg/ml | ADCP EC50 (ng/ml) |
|---|---|---|---|
| OX40SF2IgG2sigma_R2BS29_HC-C | 1 | 9 | 37.5 |
| OX40SF2IgG2sigma_R2BS29_LC-C | 1 | 4 | 16.5 |
| OX40SF2IgG2sigma_R2BS29_HC-N | 1 | 5 | 12 |
| OX40SF2IgG2sigma_R2BS29_LC-N | 1 | 8 | 8.9 |
| OX40SF2IgG2sigma | 1 | 6 | >1000 |
| OX40SF2IgG1_R2BS29_HC-C | 9 | 13 | 31.8 |
| OX40SF2IgG1_R2BS29_LC-C | 9 | 5 | 15.1 |
| OX40SF2IgG1 | 9 | 9 | 39.3 |

Effect of mAbtyrins on T Cell Activation

Effect of the mAbtyrins on T cell activation was evaluated. Briefly, recombinant FcγRIIB or FcγRIIA protein was coated on the plate to provide the crosslinking activity. For T cell activation assay, 100 μL of 30 ng/mL anti-CD3 antibody (OKT3) and 1 μg/mL FcγRIIB or FcγRIIA protein in DPBS were coated in U-bottomed 96-well tissue culture plate overnight. CD4 positive T cells were isolated from PBMC by negative selection. OX40 expression was induced by culturing the isolated T cells in the presence of 1 μg/mL PHA overnight. On the assay day, the coating solution in the plate were aspirated and 150 μL RPMI media was added to block the plate. The cultured T cells were washed three times by RPMI culture media and between 25,000 to 50,000 CD4 positive T cells were seeded in each well in the assay plate. Test mAbtyrins were added to the cells and the plate was incubated for 3 days. T cell activation was assessed by the induction of IFNγ or TNFα production, which was quantitated by human IFNγ or TNFα ELISA detection kit (Biolegend). Prior to T cell activation assay, the binding affinity of mAbtyrins to immobilized FcγRIIB or FcγRIIA protein were evaluated by an ELISA assay. In the assay, 100 μL of 1 μg/mL of FcγRIIB or FcγRIIA protein was coated on Maxisorp 96-well plate one day before. mAbtyrins were added to the assay well and incubated for 2 h. The binding of mAbtyrins to immobilized FcγRIIB or FcγRIIA protein were detected by HRP-conjugated anti-Human IgG(γ) secondary antibody and quantitated by ELISA assay using TMB substrate.

All tested mAbtyrins studied showed binding to immobilized FcγRIIB or FcγRIIA protein in a dose-dependent manner regardless of positioning of the FN3 domain in the mAbtyrin. Effector silent OX40SF2IgG2sigma demonstrated no binding to either receptor. OX40SF2IgG1 demonstrated no binding to immobilized FcγRIIB and some binding to immobilized FcγRIIA (data not shown).

Under the test conditions neither OX40SF2IgG1 nor OX40SF2IgG2sigma mAb had significant agonistic activity in this T cell activation assay, indicative of lack or reduced binding to immobilized FcγRII. mAbtyrins with the FN3 domain positioned on the C-terminus of heavy chain dose-dependently mediated IFNγ or TNFα production regardless of mAbtyrin isotype. Positioning of the FN3 domain to the N-terminus in the mAbtyrin did not confer the antibody with the ability to activate T cells. Table 19 shows mAbtyrin induced production of IFNγ or TNFα by activated T cells cross-linked by either FcγRIIB or FcγRIIA.

TABLE 19

| Construct | FcγRIIb IFNγ (pg/ml) | FcγRIIb TNFα (pg/ml) | FcγRIIA IFNγ (pg/ml) | FcγRIIA TNFα (pg/ml) |
|---|---|---|---|---|
| OX40SF2IgG2sigma_R2BS29_HC-C | 1326 | 250 | 1549 | 226 |
| OX40SF2IgG2sigma_R2BS29_LC-C | 89 | 30 | 153 | 30 |
| OX40SF2IgG2sigma_R2BS29_HC-N | 76 | 29 | 89 | 28 |
| OX40SF2IgG2sigma_R2BS29_LC-N | 72 | 29 | 103 | 29 |
| OX40SF2IgG2sigma | 70 | 30 | 97 | 28 |
| OX40SF2IgG1_R2BS29_HC-C | 1369 | 250 | 1756 | 335 |
| OX40SF2IgG1_R2BS29_LC-C | 177 | 37 | 125 | 33 |
| OX40SF2IgG1 | 70 | 30 | 92 | 28 |
| OX40 ligand | 1127 | 315 | 1674 | 507 |

We claim:

1. A method of enhancing antibody dependent cellular phagocytosis (ADCP) activity of a polypeptide, comprising:
    conjugating a FcγRII binding fibronectin type III (FN3) domain comprising the sequence of SEQ ID NO: 16, 17, 18, 19, 20, 21, or 22 to the polypeptide to thereby enhance the ADCP activity of the polypeptide.

2. The method of claim 1, wherein the FN3 domain comprises the sequence of SEQ ID NO: 16.

3. The method of claim 1, wherein the FN3 domain comprises the sequence of SEQ ID NO: 17.

4. The method of claim 1, wherein the FN3 domain comprises the sequence of SEQ ID NO: 18.

5. The method of claim 1, wherein the FN3 domain comprises the sequence of SEQ ID NO: 19.

6. The method of claim 1, wherein the FN3 domain comprises the sequence of SEQ ID NO: 20.

7. The method of claim 1, wherein the FN3 domain comprises the sequence of SEQ ID NO: 21.

8. The method of claim 1, wherein the FN3 domain comprises the sequence of SEQ ID NO: 22.

9. The method of claim 1, wherein the polypeptide is an antibody.

10. The method of claim 1, wherein the FN3 domain is conjugated to the N-terminus of the polypeptide.

11. The method of claim 1, wherein the FN3 domain is conjugated to the C-terminus of the polypeptide.

12. The method of claim 1, wherein the conjugating comprises cloning the FN3 domain and the polypeptide into a vector and expressing a FN3-polypeptide conjugate.

13. The method of claim 1, wherein the conjugating comprises chemically coupling the FN3 domain and the polypeptide.

* * * * *

SEQUENCE LISTING

<160> NUMBER OF SEQ ID NOS: 59

<210> SEQ ID NO 1
<211> LENGTH: 277
<212> TYPE: PRT
<213> ORGANISM: Homo sapiens

<400> SEQUENCE: 1

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
                20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
        50                  55                  60

```
Arg Pro Cys Gly Pro Gly Phe Tyr Asn Asp Val Val Ser Ser Lys Pro
 65                  70                  75                  80

Cys Lys Pro Cys Thr Trp Cys Asn Leu Arg Ser Gly Ser Glu Arg Lys
                 85                  90                  95

Gln Leu Cys Thr Ala Thr Gln Asp Thr Val Cys Arg Cys Arg Ala Gly
             100                 105                 110

Thr Gln Pro Leu Asp Ser Tyr Lys Pro Gly Val Asp Cys Ala Pro Cys
             115                 120                 125

Pro Pro Gly His Phe Ser Pro Gly Asp Asn Gln Ala Cys Lys Pro Trp
             130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                 165                 170                 175

Gln Glu Thr Gln Gly Pro Pro Ala Arg Pro Ile Thr Val Gln Pro Thr
             180                 185                 190

Glu Ala Trp Pro Arg Thr Ser Gln Gly Pro Ser Thr Arg Pro Val Glu
             195                 200                 205

Val Pro Gly Gly Arg Ala Val Ala Ala Ile Leu Gly Leu Gly Leu Val
210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                 245                 250                 255

Gly Ser Phe Arg Thr Pro Ile Gln Glu Glu Gln Ala Asp Ala His Ser
             260                 265                 270

Thr Leu Ala Lys Ile
             275

<210> SEQ ID NO 2
<211> LENGTH: 316
<212> TYPE: PRT
<213> ORGANISM: Homo sapiens

<400> SEQUENCE: 2

Met Thr Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
                 20                  25                  30

Ser Gln Ala Ala Pro Pro Lys Ala Val Leu Lys Leu Glu Pro Pro Trp
             35                  40                  45

Ile Asn Val Leu Gln Glu Asp Ser Val Thr Leu Thr Cys Gln Gly Ala
             50                  55                  60

Arg Ser Pro Glu Ser Asp Ser Ile Gln Trp Phe His Asn Gly Asn Leu
 65                  70                  75                  80

Ile Pro Thr His Thr Gln Pro Ser Tyr Arg Phe Lys Ala Asn Asn Asn
                 85                  90                  95

Asp Ser Gly Glu Tyr Thr Cys Gln Thr Gly Gln Thr Ser Leu Ser Asp
             100                 105                 110

Pro Val His Leu Thr Val Leu Ser Glu Trp Leu Val Leu Gln Thr Pro
             115                 120                 125

His Leu Glu Phe Gln Glu Gly Glu Thr Ile Met Leu Arg Cys His Ser
             130                 135                 140

Trp Lys Asp Lys Pro Leu Val Lys Val Thr Phe Phe Gln Asn Gly Lys
```

```
                145                 150                 155                 160
        Ser Gln Lys Phe Ser His Leu Asp Pro Thr Phe Ser Ile Pro Gln Ala
                        165                 170                 175

Asn His Ser His Ser Gly Asp Tyr His Cys Thr Gly Asn Ile Gly Tyr
                        180                 185                 190

Thr Leu Phe Ser Ser Lys Pro Val Thr Ile Thr Val Gln Val Pro Ser
                        195                 200                 205

Met Gly Ser Ser Pro Met Gly Ile Ile Val Ala Val Ile Ala
                210                 215                 220

Thr Ala Val Ala Ala Ile Val Ala Ala Val Val Ala Leu Ile Tyr Cys
        225                 230                 235                 240

Arg Lys Lys Arg Ile Ser Ala Asn Ser Thr Asp Pro Val Lys Ala Ala
                        245                 250                 255

Gln Phe Glu Pro Pro Gly Arg Gln Met Ile Ala Ile Arg Lys Arg Gln
                        260                 265                 270

Leu Glu Glu Thr Asn Asn Asp Tyr Glu Thr Ala Asp Gly Gly Tyr Met
                        275                 280                 285

Thr Leu Asn Pro Arg Ala Pro Thr Asp Asp Asp Lys Asn Ile Tyr Leu
                        290                 295                 300

Thr Leu Pro Pro Asn Asp His Val Asn Ser Asn Asn
        305                 310                 315

<210> SEQ ID NO 3
<211> LENGTH: 310
<212> TYPE: PRT
<213> ORGANISM: Homo sapiens

<400> SEQUENCE: 3

Met Gly Ile Leu Ser Phe Leu Pro Val Leu Ala Thr Glu Ser Asp Trp
        1               5                   10                  15

Ala Asp Cys Lys Ser Pro Gln Pro Trp Gly His Met Leu Leu Trp Thr
                        20                  25                  30

Ala Val Leu Phe Leu Ala Pro Val Ala Gly Thr Pro Ala Ala Pro Pro
                        35                  40                  45

Lys Ala Val Leu Lys Leu Glu Pro Gln Trp Ile Asn Val Leu Gln Glu
                50                  55                  60

Asp Ser Val Thr Leu Thr Cys Arg Gly Thr His Ser Pro Glu Ser Asp
        65                  70                  75                  80

Ser Ile Gln Trp Phe His Asn Gly Asn Leu Ile Pro Thr His Thr Gln
                        85                  90                  95

Pro Ser Tyr Arg Phe Lys Ala Asn Asn Asn Asp Ser Gly Glu Tyr Thr
                        100                 105                 110

Cys Gln Thr Gly Gln Thr Ser Leu Ser Asp Pro Val His Leu Thr Val
                        115                 120                 125

Leu Ser Glu Trp Leu Val Leu Gln Thr Pro His Leu Glu Phe Gln Glu
                        130                 135                 140

Gly Glu Thr Ile Val Leu Arg Cys His Ser Trp Lys Asp Lys Pro Leu
        145                 150                 155                 160

Val Lys Val Thr Phe Phe Gln Asn Gly Lys Ser Lys Lys Phe Ser Arg
                        165                 170                 175

Ser Asp Pro Asn Phe Ser Ile Pro Gln Ala Asn His Ser His Ser Gly
                        180                 185                 190

Asp Tyr His Cys Thr Gly Asn Ile Gly Tyr Thr Leu Tyr Ser Ser Lys
                        195                 200                 205
```

```
Pro Val Thr Ile Thr Val Gln Ala Pro Ser Ser Pro Met Gly Ile
    210                 215                 220
Ile Val Ala Val Val Thr Gly Ile Ala Val Ala Ile Val Ala Ala
225                 230                 235                 240
Val Val Ala Leu Ile Tyr Cys Arg Lys Lys Arg Ile Ser Ala Leu Pro
                245                 250                 255
Gly Tyr Pro Glu Cys Arg Glu Met Gly Glu Thr Leu Pro Glu Lys Pro
                260                 265                 270
Ala Asn Pro Thr Asn Pro Asp Glu Ala Asp Lys Val Gly Ala Glu Asn
                275                 280                 285
Thr Ile Thr Tyr Ser Leu Leu Met His Pro Asp Ala Leu Glu Glu Pro
290                 295                 300
Asp Asp Gln Asn Arg Ile
305                 310

<210> SEQ ID NO 4
<211> LENGTH: 89
<212> TYPE: PRT
<213> ORGANISM: Artificial Sequence
<220> FEATURE:
<223> OTHER INFORMATION: Tencon

<400> SEQUENCE: 4

Leu Pro Ala Pro Lys Asn Leu Val Val Ser Glu Val Thr Glu Asp Ser
1               5                   10                  15
Leu Arg Leu Ser Trp Thr Ala Pro Asp Ala Ala Phe Asp Ser Phe Leu
                20                  25                  30
Ile Gln Tyr Gln Glu Ser Glu Lys Val Gly Glu Ala Ile Asn Leu Thr
            35                  40                  45
Val Pro Gly Ser Glu Arg Ser Tyr Asp Leu Thr Gly Leu Lys Pro Gly
        50                  55                  60
Thr Glu Tyr Thr Val Ser Ile Tyr Gly Val Lys Gly Gly His Arg Ser
65                  70                  75                  80
Asn Pro Leu Ser Ala Glu Phe Thr Thr
                85

<210> SEQ ID NO 5
<211> LENGTH: 89
<212> TYPE: PRT
<213> ORGANISM: Artificial Sequence
<220> FEATURE:
<223> OTHER INFORMATION: Tencon27

<400> SEQUENCE: 5

Leu Pro Ala Pro Lys Asn Leu Val Val Ser Arg Val Thr Glu Asp Ser
1               5                   10                  15
Ala Arg Leu Ser Trp Thr Ala Pro Asp Ala Ala Phe Asp Ser Phe Leu
                20                  25                  30
Ile Gln Tyr Gln Glu Ser Glu Lys Val Gly Glu Ala Ile Val Leu Thr
            35                  40                  45
Val Pro Gly Ser Glu Arg Ser Tyr Asp Leu Thr Gly Leu Lys Pro Gly
        50                  55                  60
Thr Glu Tyr Thr Val Ser Ile Tyr Gly Val Lys Gly Gly His Arg Ser
65                  70                  75                  80
Asn Pro Leu Ser Ala Ile Phe Thr Thr
                85

<210> SEQ ID NO 6
```

```
<211> LENGTH: 4
<212> TYPE: PRT
<213> ORGANISM: Artificial Sequence
<220> FEATURE:
<223> OTHER INFORMATION: Linker

<400> SEQUENCE: 6

Gly Ser Gly Ser
1

<210> SEQ ID NO 7
<211> LENGTH: 8
<212> TYPE: PRT
<213> ORGANISM: Artificial Sequence
<220> FEATURE:
<223> OTHER INFORMATION: Linker

<400> SEQUENCE: 7

Gly Gly Gly Ser Gly Gly Gly Ser
1               5

<210> SEQ ID NO 8
<211> LENGTH: 25
<212> TYPE: PRT
<213> ORGANISM: Artificial Sequence
<220> FEATURE:
<223> OTHER INFORMATION: Linker

<400> SEQUENCE: 8

Gly Gly Gly Gly Ser Gly Gly Gly Gly Ser Gly Gly Gly Gly Ser Gly
1               5                  10                  15

Gly Gly Ser Gly Gly Gly Gly Ser
            20                  25

<210> SEQ ID NO 9
<211> LENGTH: 4
<212> TYPE: PRT
<213> ORGANISM: Artificial Sequence
<220> FEATURE:
<223> OTHER INFORMATION: Linker

<400> SEQUENCE: 9

Ala Pro Ala Pro
1

<210> SEQ ID NO 10
<211> LENGTH: 10
<212> TYPE: PRT
<213> ORGANISM: Artificial Sequence
<220> FEATURE:
<223> OTHER INFORMATION: Linker

<400> SEQUENCE: 10

Ala Pro Ala Pro Ala Pro Ala Pro Ala Pro
1               5                   10

<210> SEQ ID NO 11
<211> LENGTH: 20
<212> TYPE: PRT
<213> ORGANISM: Artificial Sequence
<220> FEATURE:
<223> OTHER INFORMATION: Linkder

<400> SEQUENCE: 11

Ala Pro Ala Pro Ala Pro Ala Pro Ala Pro Ala Pro Ala Pro Ala Pro
1               5                   10                  15
```

Ala Pro Ala Pro
            20

<210> SEQ ID NO 12
<211> LENGTH: 40
<212> TYPE: PRT
<213> ORGANISM: Artificial Sequence
<220> FEATURE:
<223> OTHER INFORMATION: Linker

<400> SEQUENCE: 12

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro Ala Pro Ala Pro Ala Pro
        35                  40

<210> SEQ ID NO 13
<211> LENGTH: 29
<212> TYPE: PRT
<213> ORGANISM: Artificial Sequence
<220> FEATURE:
<223> OTHER INFORMATION: Linker

<400> SEQUENCE: 13

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala Ala Ala
            20                  25

<210> SEQ ID NO 14
<211> LENGTH: 21
<212> TYPE: PRT
<213> ORGANISM: Artificial Sequence
<220> FEATURE:
<223> OTHER INFORMATION: Linkder

<400> SEQUENCE: 14

Gly Gly Gly Gly Gly Ser Gly Gly Gly Gly Ser Gly Gly Gly Gly Ser
1               5                   10                  15

Gly Gly Gly Gly Ser
            20

<210> SEQ ID NO 15
<211> LENGTH: 585
<212> TYPE: PRT
<213> ORGANISM: Artificial Sequence
<220> FEATURE:
<223> OTHER INFORMATION: Albumin variant

<400> SEQUENCE: 15

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

-continued

```
Arg Glu Thr Tyr Gly Glu Met Ala Asp Cys Cys Ala Lys Gln Pro
             85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130             135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
```

```
                    500                 505                 510
Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 16
<211> LENGTH: 97
<212> TYPE: PRT
<213> ORGANISM: Artificial Sequence
<220> FEATURE:
<223> OTHER INFORMATION: R2BS6 protein

<400> SEQUENCE: 16

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Gln Tyr Ala Ala Trp Tyr
65                  70                  75                  80

Leu Pro Arg His His Glu Ala Ser Asn Pro Leu Ser Ala Ile Phe Thr
                85                  90                  95

Thr

<210> SEQ ID NO 17
<211> LENGTH: 89
<212> TYPE: PRT
<213> ORGANISM: Artificial Sequence
<220> FEATURE:
<223> OTHER INFORMATION: R2BS9 protein

<400> SEQUENCE: 17

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Tyr Tyr Leu Glu Tyr Trp Arg Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Gln Ile His Gly Val Lys Gly Gly Gln Tyr Ser
65                  70                  75                  80

Tyr Pro Leu Ser Ala Ile Phe Thr Thr
                85

<210> SEQ ID NO 18
<211> LENGTH: 89
<212> TYPE: PRT
```

```
<213> ORGANISM: Artificial Sequence
<220> FEATURE:
<223> OTHER INFORMATION: R2BS12 protein

<400> SEQUENCE: 18

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
                20                  25                  30

Ile Ala Tyr Ala Glu Tyr Trp Glu Gly Gly Ala Val Val Leu Thr
            35                  40                  45

Val Pro Gly Ser Glu Arg Ser Tyr Asp Leu Thr Gly Leu Lys Pro Gly
    50                  55                  60

Thr Glu Tyr Phe Val Gln Ile Asn Gly Val Lys Gly Gly Phe Trp Ser
65                  70                  75                  80

Ile Pro Leu Ser Ala Ile Phe Thr Thr
                85

<210> SEQ ID NO 19
<211> LENGTH: 89
<212> TYPE: PRT
<213> ORGANISM: Artificial Sequence
<220> FEATURE:
<223> OTHER INFORMATION: R2BS26 protein

<400> SEQUENCE: 19

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Pro
                20                  25                  30

Ile Ala Tyr Ile Glu Tyr Trp Thr Gly Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Phe Val Trp Ile His Gly Val Lys Gly Gly Ala Trp Ser
65                  70                  75                  80

Ser Pro Leu Ser Ala Ile Phe Thr Thr
                85

<210> SEQ ID NO 20
<211> LENGTH: 89
<212> TYPE: PRT
<213> ORGANISM: Artificial Sequence
<220> FEATURE:
<223> OTHER INFORMATION: R2BS29_protein

<400> SEQUENCE: 20

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Pro
                20                  25                  30

Ile Tyr Tyr Trp Glu Tyr Arg Val Gly Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Phe Val Tyr Ile Asn Gly Val Lys Gly Gly Glu Glu Ser
65                  70                  75                  80

Arg Pro Leu Ser Ala Ile Phe Thr Thr
                85
```

<210> SEQ ID NO 21
<211> LENGTH: 96
<212> TYPE: PRT
<213> ORGANISM: Artificial Sequence
<220> FEATURE:
<223> OTHER INFORMATION: R2BS39 protein

<400> SEQUENCE: 21

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Ser His Gly Pro Trp Tyr
65                  70                  75                  80

Asn Tyr Gly Glu Trp Arg Ser Asn Pro Leu Ser Ala Ile Phe Thr Thr
                85                  90                  95
```

<210> SEQ ID NO 22
<211> LENGTH: 89
<212> TYPE: PRT
<213> ORGANISM: Artificial Sequence
<220> FEATURE:
<223> OTHER INFORMATION: R2BS56 protein

<400> SEQUENCE: 22

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
            20                  25                  30

Ile Ala Tyr Trp Glu Tyr Arg Lys Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Leu Ile Tyr Gly Val Lys Gly Gly Trp Gln Ser
65                  70                  75                  80

Lys Pro Leu Ser Ala Ile Phe Thr Thr
                85
```

<210> SEQ ID NO 23
<211> LENGTH: 291
<212> TYPE: DNA
<213> ORGANISM: Artificial Sequence
<220> FEATURE:
<223> OTHER INFORMATION: R2BS6 cDNA

<400> SEQUENCE: 23

```
ctgccggcgc cgaaaaacct ggttgtttct cgtgttaccg aagactctgc gcgtctgtct    60
tggaccgcgc cggacgcggc gttcgactct ttcctgatcc agtaccagga atctgaaaaa   120
gttggtgaag cgatcgtgct gaccgttccg ggttctgaac gttcttacga cctgaccggt   180
ctgaaaccgg gtaccgaata caccgttttct atctacggtg ttcaatatgc ggcgtggtat   240
ctgccgcgtc accacgaggc gagcaacccg ctgtctgcga tcttcaccac c            291
```

<210> SEQ ID NO 24

<211> LENGTH: 267
<212> TYPE: DNA
<213> ORGANISM: Artificial Sequence
<220> FEATURE:
<223> OTHER INFORMATION: R2BS9 cDNA

<400> SEQUENCE: 24

| ctgccggcgc cgaaaaacct ggttgtttct cgtgttaccg aagactctgc gcgtctgtct | 60 |
| tggaccgcgc cggacgcggc gttcgactct ttctggattt attacctgga gtattggcgt | 120 |
| ggcggtgaag cgatcgttct gaccgttccg ggttctgaac gttcttacga cctgaccggt | 180 |
| ctgaaaccgg gtaccgaata tttcgttcaa attcacggcg ttaagggcgg tcaatatagt | 240 |
| tatccactgt ctgcgatctt caccacc | 267 |

<210> SEQ ID NO 25
<211> LENGTH: 267
<212> TYPE: DNA
<213> ORGANISM: Artificial Sequence
<220> FEATURE:
<223> OTHER INFORMATION: R2BS12 cDNA

<400> SEQUENCE: 25

| ctgccggcgc cgaaaaacct ggttgtttct cgtgttaccg aagactctgc gcgtctgtct | 60 |
| tggaccgcgc cggacgcggc gttcgactct tttctgatcg cgtatgcgga atattgggag | 120 |
| ggcggtgaag cggtcgttct gaccgttccg ggttctgaac gttcttacga cctgaccggt | 180 |
| ctgaaaccgg gtaccgaata tttcgttcaa atcaatggcg ttaagggtgg tttctggagt | 240 |
| atcccactgt ctgcgatctt caccacc | 267 |

<210> SEQ ID NO 26
<211> LENGTH: 267
<212> TYPE: DNA
<213> ORGANISM: Artificial Sequence
<220> FEATURE:
<223> OTHER INFORMATION: R2BS26 cDNA

<400> SEQUENCE: 26

| ctgccggcgc cgaaaaacct ggttgtttct cgtgttaccg aagactctgc gcgtctgtct | 60 |
| tggaccgcgc cggacgcggc gttcgactct tttccgatcg cgtatatcga gtattggact | 120 |
| ggcggtgaag cgatcgttct gaccgttccg ggttctgaac gttcttacga cctgaccggt | 180 |
| ctgaaaccgg gtaccgaata tttcgtttgg attcacggcg ttaagggtgg tgcgtggtcc | 240 |
| agcccgctgt ctgcgatctt caccacc | 267 |

<210> SEQ ID NO 27
<211> LENGTH: 267
<212> TYPE: DNA
<213> ORGANISM: Artificial Sequence
<220> FEATURE:
<223> OTHER INFORMATION: R2BS29 cDNA

<400> SEQUENCE: 27

| ctgccggcgc cgaaaaacct ggttgtttct cgtgttaccg aagactctgc gcgtctgtct | 60 |
| tggaccgcgc cggacgcggc gttcgactct tttccgatct attattggga atatcgtgtt | 120 |
| ggcggtgaag cgatcgttct gaccgttccg ggttctgaac gttcttacga cctgaccggt | 180 |
| ctgaaaccgg gtaccgaata cttcgtttat atcaatggtg ttaaaggtgg cgaggagagt | 240 |
| cgtccgctgt ctgcgatctt caccacc | 267 |

<210> SEQ ID NO 28
<211> LENGTH: 288
<212> TYPE: DNA
<213> ORGANISM: Artificial Sequence
<220> FEATURE:
<223> OTHER INFORMATION: R2BS39 cDNA

<400> SEQUENCE: 28

```
ctgccggcgc cgaaaaacct ggttgtttct cgtgttaccg aagactctgc gcgtctgtct      60
tggaccgcgc cggacgcggc gttcgactct ttcctgatcc agtaccagga atctgaaaaa     120
gttggtgaag cgatcgtgct gaccgttccg ggttctgaac gttcttacga cctgaccggt     180
ctgaaaccgg gtaccgaata caccgtttct atctacggtg tgagccacgg cccgtggtat     240
aattatggcg agtggcgttc taacccgctg tctgcgatct tcaccacc                  288
```

<210> SEQ ID NO 29
<211> LENGTH: 267
<212> TYPE: DNA
<213> ORGANISM: Artificial Sequence
<220> FEATURE:
<223> OTHER INFORMATION: R2BS56 cDNA

<400> SEQUENCE: 29

```
ctgccggcgc cgaaaaacct ggttgtttct cgtgttaccg aagactctgc gcgtctgtct      60
tggaccgcgc cggacgcggc gttcgactct tttagcattg cgtactggga gtatcgtaaa     120
ggcggtgaag cgatcgttct gaccgttccg ggttctgaac gttcttacga cctgaccggt     180
ctgaaaccgg gtaccgaata tttcgttctg atctatggtg tcaagggcgg ttggcaatcc     240
aaaccactgt ctgcgatctt caccacc                                         267
```

<210> SEQ ID NO 30
<211> LENGTH: 447
<212> TYPE: PRT
<213> ORGANISM: Artificial Sequence
<220> FEATURE:
<223> OTHER INFORMATION: hcOX40SF2IgG2sigma_HC

<400> SEQUENCE: 30

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Thr Tyr Asn Gln Asn Phe
    50                  55                  60

Lys Asp Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160
```

-continued

```
Ser Trp Asn Ser Gly Ala Leu Thr Ser Gly Val His Thr Phe Pro Ala
            165                 170                 175
Val Leu Gln Ser Ser Gly Leu Tyr Ser Leu Ser Ser Val Val Thr Val
        180                 185                 190
Pro Ser Ser Asn Phe Gly Thr Gln Thr Tyr Thr Cys Asn Val Asp His
        195                 200                 205
Lys Pro Ser Asn Thr Lys Val Asp Lys Thr Val Glu Arg Lys Cys Cys
        210                 215                 220
Val Glu Cys Pro Pro Cys Pro Ala Pro Ala Ala Ser Ser Val
225                 230                 235                 240
Phe Leu Phe Pro Pro Lys Pro Lys Asp Thr Leu Met Ile Ser Arg Thr
            245                 250                 255
Pro Glu Val Thr Cys Val Val Val Asp Val Ser Ala Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Phe Arg Val Val Ser
        290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
            325                 330                 335
Ser Lys Thr Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Met Leu Asp Ser
385                 390                 395                 400
Asp Gly Ser Phe Phe Leu Tyr Ser Lys Leu Thr Val Asp Lys Ser Arg
            405                 410                 415
Trp Gln Gln Gly Asn Val Phe Ser Cys Ser Val Met His Glu Ala Leu
        420                 425                 430
His Asn His Tyr Thr Gln Lys Ser Leu Ser Leu Ser Pro Gly Lys
        435                 440                 445

<210> SEQ ID NO 31
<211> LENGTH: 214
<212> TYPE: PRT
<213> ORGANISM: Artificial Sequence
<220> FEATURE:
<223> OTHER INFORMATION: 1cOX40SF2_LC

<400> SEQUENCE: 31

Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asp Val Gly Ala Ala
            20                  25                  30
Val Ala Trp Tyr Gln Gln Lys Pro Gly Lys Ala Pro Lys Leu Leu Ile
        35                  40                  45
Tyr Trp Ala Ser Thr Arg His Thr Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Tyr Ile Asn Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 32
<211> LENGTH: 565
<212> TYPE: PRT
<213> ORGANISM: Artificial Sequence
<220> FEATURE:
<223> OTHER INFORMATION: hcOX40SF2IgG2sigma _R2BS6_HC-C

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Thr Tyr Asn Gln Asn Phe
    50                  55                  60

Lys Asp Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ala Ser Thr Lys Gly Pro Ser
            115                 120                 125

Val Phe Pro Leu Ala Pro Cys Ser Arg Ser Thr Ser Glu Ser Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
            195                 200                 205

Lys Pro Ser Asn Thr Lys Val Asp Lys Thr Val Glu Arg Lys Cys Cys
            210                 215                 220

```
Val Glu Cys Pro Pro Cys Pro Ala Pro Pro Ala Ala Ser Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Ala Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Gly Ser Gly Gly Gly Ser Gly Gly Gly Gly Ser Gly
450                 455                 460

Gly Gly Gly Ser Leu Pro Ala Pro Lys Asn Leu Val Val Ser Arg Val
465                 470                 475                 480

Thr Glu Asp Ser Ala Arg Leu Ser Trp Thr Ala Pro Asp Ala Ala Phe
            485                 490                 495

Asp Ser Phe Leu Ile Gln Tyr Gln Glu Ser Glu Lys Val Gly Glu Ala
        500                 505                 510

Ile Val Leu Thr Val Pro Gly Ser Glu Arg Ser Tyr Asp Leu Thr Gly
            515                 520                 525

Leu Lys Pro Gly Thr Glu Tyr Thr Val Ser Ile Tyr Gly Val Gln Tyr
        530                 535                 540

Ala Ala Trp Tyr Leu Pro Arg His His Glu Ala Ser Asn Pro Leu Ser
545                 550                 555                 560

Ala Ile Phe Thr Thr
                565

<210> SEQ ID NO 33
<211> LENGTH: 557
<212> TYPE: PRT
<213> ORGANISM: Artificial Sequence
<220> FEATURE:
<223> OTHER INFORMATION: hcOX40SF2IgG2sigma _R2BS9_HC-C

<400> SEQUENCE: 33

Gln Val Gln Leu Val Gln Ser Gly Ala Glu Val Lys Lys Pro Gly Ser
1               5                   10                  15
```

```
Ser Val Lys Val Ser Cys Lys Ala Ser Gly Tyr Thr Phe Lys Asp Tyr
             20                  25                  30

Thr Met His Trp Val Arg Gln Ala Pro Gly Gln Gly Leu Glu Trp Ile
         35                  40                  45

Gly Gly Ile Tyr Pro Asn Asn Gly Gly Ser Thr Tyr Asn Gln Asn Phe
     50                  55                  60

Lys Asp Arg Val Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Met Gly Tyr His Gly Pro His Leu Asp Phe Asp Val Trp Gly
            100                 105                 110

Gln Gly Thr Thr Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
            195                 200                 205

Lys Pro Ser Asn Thr Lys Val Asp Lys Thr Val Glu Arg Lys Cys Cys
210                 215                 220

Val Glu Cys Pro Pro Cys Pro Ala Pro Pro Ala Ala Ala Ser Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Ala Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Phe Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
```

-continued

```
            435                 440                 445
Gly Gly Gly Gly Ser Gly Gly Gly Ser Gly Gly Gly Ser Gly
            450                 455                 460
Gly Gly Gly Ser Leu Pro Ala Pro Lys Asn Leu Val Ser Arg Val
465                 470                 475                 480
Thr Glu Asp Ser Ala Arg Leu Ser Trp Thr Ala Pro Asp Ala Ala Phe
                    485                 490                 495
Asp Ser Phe Trp Ile Tyr Tyr Leu Glu Tyr Trp Arg Gly Gly Glu Ala
                500                 505                 510
Ile Val Leu Thr Val Pro Gly Ser Glu Arg Ser Tyr Asp Leu Thr Gly
                515                 520                 525
Leu Lys Pro Gly Thr Glu Tyr Phe Val Gln Ile His Gly Val Lys Gly
            530                 535                 540
Gly Gln Tyr Ser Tyr Pro Leu Ser Ala Ile Phe Thr Thr
545                 550                 555
```

<210> SEQ ID NO 34
<211> LENGTH: 557
<212> TYPE: PRT
<213> ORGANISM: Artificial Sequence
<220> FEATURE:
<223> OTHER INFORMATION: hcOX40SF2IgG2sigma _R2BS12_HC-C

<400> SEQUENCE: 34

```
Gln Val Gln Leu Val Gln Ser Gly Ala Glu Val Lys Lys Pro Gly Ser
1               5                   10                  15
Ser Val Lys Val Ser Cys Lys Ala Ser Gly Tyr Thr Phe Lys Asp Tyr
            20                  25                  30
Thr Met His Trp Val Arg Gln Ala Pro Gly Gln Gly Leu Glu Trp Ile
        35                  40                  45
Gly Gly Ile Tyr Pro Asn Asn Gly Gly Ser Thr Tyr Asn Gln Asn Phe
    50                  55                  60
Lys Asp Arg Val Thr Leu Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Met Gly Tyr His Gly Pro His Leu Asp Phe Asp Val Trp Gly
            100                 105                 110
Gln Gly Thr Thr Val Thr Val Ser Ser Ala Ser Thr Lys Gly Pro Ser
        115                 120                 125
Val Phe Pro Leu Ala Pro Cys Ser Arg Ser Thr Ser Glu Ser Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Asn Phe Gly Thr Gln Thr Tyr Thr Cys Asn Val Asp His
        195                 200                 205
Lys Pro Ser Asn Thr Lys Val Asp Lys Thr Val Glu Arg Lys Cys Cys
    210                 215                 220
Val Glu Cys Pro Pro Cys Pro Ala Pro Pro Ala Ala Ala Ser Ser Val
225                 230                 235                 240
Phe Leu Phe Pro Pro Lys Pro Lys Asp Thr Leu Met Ile Ser Arg Thr
```

```
            245                 250                 255
Pro Glu Val Thr Cys Val Val Asp Val Ser Ala Glu Asp Pro Glu
        260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Phe Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Gly Ser Gly Gly Gly Ser Gly Gly Gly Gly Ser Gly
    450                 455                 460

Gly Gly Gly Ser Leu Pro Ala Pro Lys Asn Leu Val Val Ser Arg Val
465                 470                 475                 480

Thr Glu Asp Ser Ala Arg Leu Ser Trp Thr Ala Pro Asp Ala Ala Phe
                485                 490                 495

Asp Ser Phe Leu Ile Ala Tyr Ala Glu Tyr Trp Glu Gly Gly Glu Ala
            500                 505                 510

Val Val Leu Thr Val Pro Gly Ser Glu Arg Ser Tyr Asp Leu Thr Gly
        515                 520                 525

Leu Lys Pro Gly Thr Glu Tyr Phe Val Gln Ile Asn Gly Val Lys Gly
    530                 535                 540

Gly Phe Trp Ser Ile Pro Leu Ser Ala Ile Phe Thr Thr
545                 550                 555

<210> SEQ ID NO 35
<211> LENGTH: 557
<212> TYPE: PRT
<213> ORGANISM: Artificial Sequence
<220> FEATURE:
<223> OTHER INFORMATION: hcOX40SF2IgG2sigma _R2BS26_HC-C

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Thr Tyr Asn Gln Asn Phe
```

```
           50                  55                  60
Lys Asp Arg Val Thr Leu Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
                     85                  90                  95
Ala Arg Met Gly Tyr His Gly Pro His Leu Asp Phe Asp Val Trp Gly
                    100                 105                 110
Gln Gly Thr Thr Val Thr Val Ser Ser Ala Ser Thr Lys Gly Pro Ser
                115                 120                 125
Val Phe Pro Leu Ala Pro Cys Ser Arg Ser Thr Ser Glu Ser Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Asn Phe Gly Thr Gln Thr Tyr Thr Cys Asn Val Asp His
                195                 200                 205
Lys Pro Ser Asn Thr Lys Val Asp Lys Thr Val Glu Arg Lys Cys Cys
210                 215                 220
Val Glu Cys Pro Pro Cys Pro Ala Pro Pro Ala Ala Ala Ser Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Ala Glu Asp Pro Glu
                260                 265                 270
Val Gln Phe Asn Trp Tyr Val Asp Gly Val Glu Val His Asn Ala Lys
                275                 280                 285
Thr Lys Pro Arg Glu Glu Gln Phe Asn Ser Thr Phe Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Thr Lys Gly Gln Pro Arg Glu Pro Gln Val Tyr Thr Leu Pro
                340                 345                 350
Pro Ser Arg Glu Glu Met Thr Lys Asn Gln Val Ser Leu Thr Cys Leu
                355                 360                 365
Val Lys Gly Phe Tyr Pro Ser Asp Ile Ala Val Glu Trp Glu Ser Asn
                370                 375                 380
Gly Gln Pro Glu Asn Asn Tyr Lys Thr Thr Pro Pro Met Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
                420                 425                 430
His Asn His Tyr Thr Gln Lys Ser Leu Ser Leu Ser Pro Gly Lys Gly
                435                 440                 445
Gly Gly Gly Gly Ser Gly Gly Gly Ser Gly Gly Gly Gly Ser Gly
450                 455                 460
Gly Gly Gly Ser Leu Pro Ala Pro Lys Asn Leu Val Val Ser Arg Val
465                 470                 475                 480
```

```
Thr Glu Asp Ser Ala Arg Leu Ser Trp Thr Ala Pro Asp Ala Ala Phe
                485                 490                 495

Asp Ser Phe Pro Ile Ala Tyr Ile Glu Tyr Trp Thr Gly Gly Glu Ala
            500                 505                 510

Ile Val Leu Thr Val Pro Gly Ser Glu Arg Ser Tyr Asp Leu Thr Gly
        515                 520                 525

Leu Lys Pro Gly Thr Glu Tyr Phe Val Trp Ile His Gly Val Lys Gly
    530                 535                 540

Gly Ala Trp Ser Ser Pro Leu Ser Ala Ile Phe Thr Thr
545                 550                 555

<210> SEQ ID NO 36
<211> LENGTH: 557
<212> TYPE: PRT
<213> ORGANISM: Artificial Sequence
<220> FEATURE:
<223> OTHER INFORMATION: hcOX40SF2IgG2sigma _R2BS29_HC-C

<400> SEQUENCE: 36

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Thr Tyr Asn Gln Asn Phe
    50                  55                  60

Lys Asp Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Ala Ala Ala Ser Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Ala Glu Asp Pro Glu
            260                 265                 270

Val Gln Phe Asn Trp Tyr Val Asp Gly Val Glu Val His Asn Ala Lys
        275                 280                 285
```

```
Thr Lys Pro Arg Glu Glu Gln Phe Asn Ser Thr Phe Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Gly Ser Gly Gly Gly Gly Ser Gly Gly Gly Gly Ser Gly
    450                 455                 460

Gly Gly Gly Ser Leu Pro Ala Pro Lys Asn Leu Val Val Ser Arg Val
465                 470                 475                 480

Thr Glu Asp Ser Ala Arg Leu Ser Trp Thr Ala Pro Asp Ala Ala Phe
                485                 490                 495

Asp Ser Phe Pro Ile Tyr Tyr Trp Glu Tyr Arg Val Gly Gly Glu Ala
            500                 505                 510

Ile Val Leu Thr Val Pro Gly Ser Glu Arg Ser Tyr Asp Leu Thr Gly
        515                 520                 525

Leu Lys Pro Gly Thr Glu Tyr Phe Val Tyr Ile Asn Gly Val Lys Gly
    530                 535                 540

Gly Glu Glu Ser Arg Pro Leu Ser Ala Ile Phe Thr Thr
545                 550                 555
```

<210> SEQ ID NO 37
<211> LENGTH: 564
<212> TYPE: PRT
<213> ORGANISM: Artificial Sequence
<220> FEATURE:
<223> OTHER INFORMATION: hcOX40SF2IgG2sigma _R2BS39_HC-C

<400> SEQUENCE: 37

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Thr Tyr Asn Gln Asn Phe
    50                  55                  60

Lys Asp Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Met Gly Tyr His Gly Pro His Leu Asp Phe Asp Val Trp Gly
                100                 105                 110

Gln Gly Thr Thr Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Ala Ala Ser Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Ala Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Gly Ser Gly Gly Gly Gly Ser Gly Gly Gly Gly Ser Gly
    450                 455                 460

Gly Gly Ser Leu Pro Ala Pro Lys Asn Leu Val Val Ser Arg Val
465                 470                 475                 480

Thr Glu Asp Ser Ala Arg Leu Ser Trp Thr Ala Pro Asp Ala Ala Phe
                485                 490                 495

Asp Ser Phe Leu Ile Gln Tyr Gln Glu Ser Glu Lys Val Gly Glu Ala
            500                 505                 510
```

```
Ile Val Leu Thr Val Pro Gly Ser Glu Arg Ser Tyr Asp Leu Thr Gly
            515                 520                 525

Leu Lys Pro Gly Thr Glu Tyr Thr Val Ser Ile Tyr Gly Val Ser His
        530                 535                 540

Gly Pro Trp Tyr Asn Tyr Gly Glu Trp Arg Ser Asn Pro Leu Ser Ala
545                 550                 555                 560

Ile Phe Thr Thr

<210> SEQ ID NO 38
<211> LENGTH: 557
<212> TYPE: PRT
<213> ORGANISM: Artificial Sequence
<220> FEATURE:
<223> OTHER INFORMATION: hcOX40SF2IgG2sigma _R2BS56_HC-C

<400> SEQUENCE: 38

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Thr Tyr Asn Gln Asn Phe
    50                  55                  60

Lys Asp Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Ala Ala Ala Ser Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Ala Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Leu His Gln Asp Trp Leu Asn Gly Lys Glu Tyr Lys
```

```
                        305                 310                 315                 320
    Cys Lys Val Ser Asn Lys Gly Leu Pro Ser Ser Ile Glu Lys Thr Ile
                    325                 330                 335

Ser Lys Thr Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Met Leu Asp Ser
    385                 390                 395                 400

Asp Gly Ser Phe Phe Leu Tyr Ser Lys Leu Thr Val Asp Lys Ser Arg
                    405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys Gly
            435                 440                 445

Gly Gly Gly Gly Ser Gly Gly Gly Gly Ser Gly Gly Gly Gly Ser Gly
        450                 455                 460

Gly Gly Gly Ser Leu Pro Ala Pro Lys Asn Leu Val Val Ser Arg Val
    465                 470                 475                 480

Thr Glu Asp Ser Ala Arg Leu Ser Trp Thr Ala Pro Asp Ala Ala Phe
                    485                 490                 495

Asp Ser Phe Ser Ile Ala Tyr Trp Glu Tyr Arg Lys Gly Gly Glu Ala
                500                 505                 510

Ile Val Leu Thr Val Pro Gly Ser Glu Arg Ser Tyr Asp Leu Thr Gly
            515                 520                 525

Leu Lys Pro Gly Thr Glu Tyr Phe Val Leu Ile Tyr Gly Val Lys Gly
        530                 535                 540

Gly Trp Gln Ser Lys Pro Leu Ser Ala Ile Phe Thr Thr
    545                 550                 555

<210> SEQ ID NO 39
<211> LENGTH: 451
<212> TYPE: PRT
<213> ORGANISM: Artificial Sequence
<220> FEATURE:
<223> OTHER INFORMATION: hcOX40SF2IgG1_HC

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Thr Tyr Asn Gln Asn Phe
    50                  55                  60

Lys Asp Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser Ala Ser Thr Lys Gly Pro Ser
```

```
                115                 120                 125
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 40
<211> LENGTH: 556
<212> TYPE: PRT
<213> ORGANISM: Artificial Sequence
<220> FEATURE:
<223> OTHER INFORMATION: hcOX40SF2IgG2sigma_R2BS29_HC-N

<400> SEQUENCE: 40

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Pro
```

-continued

```
                20                  25                  30
Ile Tyr Tyr Trp Glu Tyr Arg Val Gly Gly Glu Ala Ile Val Leu Thr
            35                  40                  45
Val Pro Gly Ser Glu Arg Ser Tyr Asp Leu Thr Gly Leu Lys Pro Gly
        50                  55                  60
Thr Glu Tyr Phe Val Tyr Ile Asn Gly Val Lys Gly Gly Glu Glu Ser
65                  70                  75                  80
Arg Pro Leu Ser Ala Ile Phe Thr Thr Gly Gly Gly Ser Gly Gly
                85                  90                  95
Gly Gly Ser Gly Gly Gly Gly Ser Gly Gly Gly Gly Ser Gln Val Gln
            100                 105                 110
Leu Val Gln Ser Gly Ala Glu Val Lys Lys Pro Gly Ser Ser Val Lys
        115                 120                 125
Val Ser Cys Lys Ala Ser Gly Tyr Thr Phe Lys Asp Tyr Thr Met His
        130                 135                 140
Trp Val Arg Gln Ala Pro Gly Gln Gly Leu Glu Trp Ile Gly Gly Ile
145                 150                 155                 160
Tyr Pro Asn Asn Gly Gly Ser Thr Tyr Asn Gln Asn Phe Lys Asp Arg
                165                 170                 175
Val Thr Leu Thr Ala Asp Lys Ser Thr Ser Thr Ala Tyr Met Glu Leu
            180                 185                 190
Ser Ser Leu Arg Ser Glu Asp Thr Ala Val Tyr Tyr Cys Ala Arg Met
        195                 200                 205
Gly Tyr His Gly Pro His Leu Asp Phe Asp Val Trp Gly Gln Gly Thr
        210                 215                 220
Thr Val Thr Val Ser Ser Ala Ser Thr Lys Gly Pro Ser Val Phe Pro
225                 230                 235                 240
Leu Ala Pro Cys Ser Arg Ser Thr Ser Glu Ser Thr Ala Ala Leu Gly
                245                 250                 255
Cys Leu Val Lys Asp Tyr Phe Pro Glu Pro Val Thr Val Ser Trp Asn
            260                 265                 270
Ser Gly Ala Leu Thr Ser Gly Val His Thr Phe Pro Ala Val Leu Gln
        275                 280                 285
Ser Ser Gly Leu Tyr Ser Leu Ser Ser Val Val Thr Val Pro Ser Ser
        290                 295                 300
Asn Phe Gly Thr Gln Thr Tyr Thr Cys Asn Val Asp His Lys Pro Ser
305                 310                 315                 320
Asn Thr Lys Val Asp Lys Thr Val Glu Arg Lys Cys Cys Val Glu Cys
                325                 330                 335
Pro Pro Cys Pro Ala Pro Pro Ala Ala Ala Ser Ser Val Phe Leu Phe
            340                 345                 350
Pro Pro Lys Pro Lys Asp Thr Leu Met Ile Ser Arg Thr Pro Glu Val
        355                 360                 365
Thr Cys Val Val Asp Val Ser Ala Glu Asp Pro Glu Val Gln Phe
        370                 375                 380
Asn Trp Tyr Val Asp Gly Val Glu Val His Asn Ala Lys Thr Lys Pro
385                 390                 395                 400
Arg Glu Glu Gln Phe Asn Ser Thr Phe Arg Val Val Ser Val Leu Thr
                405                 410                 415
Val Leu His Gln Asp Trp Leu Asn Gly Lys Glu Tyr Lys Cys Lys Val
            420                 425                 430
Ser Asn Lys Gly Leu Pro Ser Ser Ile Glu Lys Thr Ile Ser Lys Thr
        435                 440                 445
```

```
Lys Gly Gln Pro Arg Glu Pro Gln Val Tyr Thr Leu Pro Pro Ser Arg
        450                 455                 460

Glu Glu Met Thr Lys Asn Gln Val Ser Leu Thr Cys Leu Val Lys Gly
465                 470                 475                 480

Phe Tyr Pro Ser Asp Ile Ala Val Glu Trp Glu Ser Asn Gly Gln Pro
                485                 490                 495

Glu Asn Asn Tyr Lys Thr Thr Pro Pro Met Leu Asp Ser Asp Gly Ser
            500                 505                 510

Phe Phe Leu Tyr Ser Lys Leu Thr Val Asp Lys Ser Arg Trp Gln Gln
        515                 520                 525

Gly Asn Val Phe Ser Cys Ser Val Met His Glu Ala Leu His Asn His
        530                 535                 540

Tyr Thr Gln Lys Ser Leu Ser Leu Ser Pro Gly Lys
545                 550                 555

<210> SEQ ID NO 41
<211> LENGTH: 323
<212> TYPE: PRT
<213> ORGANISM: Artificial Sequence
<220> FEATURE:
<223> OTHER INFORMATION: 1cOX40SF2_R2BS29_LC-N

<400> SEQUENCE: 41

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Pro
            20                  25                  30

Ile Tyr Tyr Trp Glu Tyr Arg Val Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Phe Val Tyr Ile Asn Gly Val Lys Gly Gly Glu Glu Ser
65                  70                  75                  80

Arg Pro Leu Ser Ala Ile Phe Thr Thr Gly Gly Gly Ser Gly Gly
            85                  90                  95

Gly Gly Ser Gly Gly Gly Ser Gly Gly Gly Ser Asp Ile Gln
                100                 105                 110

Met Thr Gln Ser Pro Ser Ser Leu Ser Ala Ser Val Gly Asp Arg Val
            115                 120                 125

Thr Ile Thr Cys Lys Ala Ser Gln Asp Val Gly Ala Ala Val Ala Trp
        130                 135                 140

Tyr Gln Gln Lys Pro Gly Lys Ala Pro Lys Leu Leu Ile Tyr Trp Ala
145                 150                 155                 160

Ser Thr Arg His Thr Gly Val Pro Ser Arg Phe Ser Gly Ser Gly Ser
                165                 170                 175

Gly Thr Asp Phe Thr Leu Thr Ile Ser Ser Leu Gln Pro Glu Asp Phe
            180                 185                 190

Ala Thr Tyr Tyr Cys Gln Gln Tyr Ile Asn Tyr Pro Leu Thr Phe Gly
        195                 200                 205

Gly Gly Thr Lys Val Glu Ile Lys Arg Thr Val Ala Ala Pro Ser Val
    210                 215                 220

Phe Ile Phe Pro Pro Ser Asp Glu Gln Leu Lys Ser Gly Thr Ala Ser
225                 230                 235                 240

Val Val Cys Leu Leu Asn Asn Phe Tyr Pro Arg Glu Ala Lys Val Gln
                245                 250                 255
```

-continued

```
Trp Lys Val Asp Asn Ala Leu Gln Ser Gly Asn Ser Gln Glu Ser Val
            260                 265                 270

Thr Glu Gln Asp Ser Lys Asp Ser Thr Tyr Ser Leu Ser Ser Thr Leu
        275                 280                 285

Thr Leu Ser Lys Ala Asp Tyr Glu Lys His Lys Val Tyr Ala Cys Glu
290                 295                 300

Val Thr His Gln Gly Leu Ser Ser Pro Val Thr Lys Ser Phe Asn Arg
305                 310                 315                 320

Gly Glu Cys

<210> SEQ ID NO 42
<211> LENGTH: 324
<212> TYPE: PRT
<213> ORGANISM: Artificial Sequence
<220> FEATURE:
<223> OTHER INFORMATION: lcOX40SF2_R2BS29_LC-C

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ala Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Asn Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Gly Gly Gly Gly Ser Gly Gly Gly Ser Met Leu Pro Ala Pro Lys
225                 230                 235                 240

Asn Leu Val Val Ser Arg Val Thr Glu Asp Ser Ala Arg Leu Ser Trp
                245                 250                 255

Thr Ala Pro Asp Ala Ala Phe Asp Ser Phe Pro Ile Tyr Tyr Trp Glu
            260                 265                 270

Tyr Arg Val Gly Gly Glu Ala Ile Val Leu Thr Val Pro Gly Ser Glu
        275                 280                 285
```

```
Arg Ser Tyr Asp Leu Thr Gly Leu Lys Pro Gly Thr Glu Tyr Phe Val
    290                 295                 300

Tyr Ile Asn Gly Val Lys Gly Glu Glu Ser Arg Pro Leu Ser Ala
305                 310                 315                 320

Ile Phe Thr Thr

<210> SEQ ID NO 43
<211> LENGTH: 561
<212> TYPE: PRT
<213> ORGANISM: Artificial Sequence
<220> FEATURE:
<223> OTHER INFORMATION: hcOX40SF2IgG1 _R2BS29_HC-C

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Thr Tyr Asn Gln Asn Phe
    50                  55                  60

Lys Asp Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
```

```
                    325                 330                 335
Glu Lys Thr Ile Ser Lys Ala Lys Gly Gln Pro Arg Glu Pro Gln Val
                340                 345                 350
Tyr Thr Leu Pro Pro Ser Arg Glu Glu Met Thr Lys Asn Gln Val Ser
                355                 360                 365
Leu Thr Cys Leu Val Lys Gly Phe Tyr Pro Ser Asp Ile Ala Val Glu
            370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
            435                 440                 445
Pro Gly Lys Gly Gly Gly Gly Ser Gly Gly Gly Gly Ser Gly Gly
        450                 455                 460
Gly Gly Ser Gly Gly Gly Ser Leu Pro Ala Pro Lys Asn Leu Val
465                 470                 475                 480
Val Ser Arg Val Thr Glu Asp Ser Ala Arg Leu Ser Trp Thr Ala Pro
                485                 490                 495
Asp Ala Ala Phe Asp Ser Phe Pro Ile Tyr Tyr Trp Glu Tyr Arg Val
                500                 505                 510
Gly Gly Glu Ala Ile Val Leu Thr Val Pro Gly Ser Glu Arg Ser Tyr
            515                 520                 525
Asp Leu Thr Gly Leu Lys Pro Gly Thr Glu Tyr Phe Val Tyr Ile Asn
        530                 535                 540
Gly Val Lys Gly Gly Glu Glu Ser Arg Pro Leu Ser Ala Ile Phe Thr
545                 550                 555                 560
Thr

<210> SEQ ID NO 44
<211> LENGTH: 374
<212> TYPE: PRT
<213> ORGANISM: Homo sapiens

<400> SEQUENCE: 44

Met Trp Phe Leu Thr Thr Leu Leu Leu Trp Val Pro Val Asp Gly Gln
1               5                   10                  15
Val Asp Thr Thr Lys Ala Val Ile Thr Leu Gln Pro Pro Trp Val Ser
                20                  25                  30
Val Phe Gln Glu Glu Thr Val Thr Leu His Cys Glu Val Leu His Leu
            35                  40                  45
Pro Gly Ser Ser Ser Thr Gln Trp Phe Leu Asn Gly Thr Ala Thr Gln
        50                  55                  60
Thr Ser Thr Pro Ser Tyr Arg Ile Thr Ser Ala Ser Val Asn Asp Ser
65                  70                  75                  80
Gly Glu Tyr Arg Cys Gln Arg Gly Leu Ser Gly Arg Ser Asp Pro Ile
                85                  90                  95
Gln Leu Glu Ile His Arg Gly Trp Leu Leu Leu Gln Val Ser Ser Arg
                100                 105                 110
Val Phe Thr Glu Gly Glu Pro Leu Ala Leu Arg Cys His Ala Trp Lys
            115                 120                 125
Asp Lys Leu Val Tyr Asn Val Leu Tyr Tyr Arg Asn Gly Lys Ala Phe
```

```
            130              135              140
Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
            195                 200                 205

Thr Leu Ser Cys Glu Thr Lys Leu Leu Leu Gln Arg Pro Gly Leu Gln
            210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
                275                 280                 285

Val Trp Phe His Val Leu Phe Tyr Leu Ala Val Gly Ile Met Phe Leu
            290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Glu Leu Lys
            340                 345                 350

Cys Gln Glu Gln Lys Glu Glu Gln Leu Gln Glu Gly Val His Arg Lys
            355                 360                 365

Glu Pro Gln Gly Ala Thr
        370

<210> SEQ ID NO 45
<211> LENGTH: 359
<212> TYPE: PRT
<213> ORGANISM: Homo sapiens

<400> SEQUENCE: 45

Met Ala Glu Gly Thr Leu Trp Gln Ile Leu Cys Val Ser Ser Asp Ala
1               5                   10                  15

Gln Pro Gln Thr Phe Glu Gly Val Lys Gly Ala Asp Pro Thr Leu
                20                  25                  30

Pro Pro Gly Ser Phe Leu Pro Gly Pro Val Leu Trp Trp Gly Ser Leu
            35                  40                  45

Ala Arg Leu Gln Thr Glu Lys Ser Asp Glu Val Ser Arg Lys Gly Asn
            50                  55                  60

Trp Trp Val Thr Glu Met Gly Gly Gly Ala Gly Glu Arg Leu Phe Thr
65                  70                  75                  80

Ser Ser Cys Leu Val Gly Leu Val Pro Leu Gly Leu Arg Ile Ser Leu
                85                  90                  95

Val Thr Cys Pro Leu Gln Cys Gly Ile Met Trp Gln Leu Leu Leu Pro
            100                 105                 110

Thr Ala Leu Leu Leu Leu Val Ser Ala Gly Met Arg Thr Glu Asp Leu
            115                 120                 125
```

Pro Lys Ala Val Val Phe Leu Glu Pro Gln Trp Tyr Arg Val Leu Glu
        130                 135                 140

Lys Asp Ser Val Thr Leu Lys Cys Gln Gly Ala Tyr Ser Pro Glu Asp
145                 150                 155                 160

Asn Ser Thr Gln Trp Phe His Asn Glu Ser Leu Ile Ser Ser Gln Ala
                165                 170                 175

Ser Ser Tyr Phe Ile Asp Ala Ala Thr Val Asp Ser Gly Glu Tyr
            180                 185                 190

Arg Cys Gln Thr Asn Leu Ser Thr Leu Ser Asp Pro Val Gln Leu Glu
            195                 200                 205

Val His Ile Gly Trp Leu Leu Leu Gln Ala Pro Arg Trp Val Phe Lys
210                 215                 220

Glu Glu Asp Pro Ile His Leu Arg Cys His Ser Trp Lys Asn Thr Ala
225                 230                 235                 240

Leu His Lys Val Thr Tyr Leu Gln Asn Gly Lys Gly Arg Lys Tyr Phe
                245                 250                 255

His His Asn Ser Asp Phe Tyr Ile Pro Lys Ala Thr Leu Lys Asp Ser
                260                 265                 270

Gly Ser Tyr Phe Cys Arg Gly Leu Phe Gly Ser Lys Asn Val Ser Ser
        275                 280                 285

Glu Thr Val Asn Ile Thr Ile Thr Gln Gly Leu Ala Val Ser Thr Ile
290                 295                 300

Ser Ser Phe Phe Pro Pro Gly Tyr Gln Val Ser Phe Cys Leu Val Met
305                 310                 315                 320

Val Leu Leu Phe Ala Val Asp Thr Gly Leu Tyr Phe Ser Val Lys Thr
                325                 330                 335

Asn Ile Arg Ser Ser Thr Arg Asp Trp Lys Asp His Lys Phe Lys Trp
                340                 345                 350

Arg Lys Asp Pro Gln Asp Lys
        355

<210> SEQ ID NO 46
<211> LENGTH: 1341
<212> TYPE: DNA
<213> ORGANISM: Artificial Sequence
<220> FEATURE:
<223> OTHER INFORMATION: hcOX40SF2IgG2sigma_HC cDNA

<400> SEQUENCE: 46
caggtgcagc tggtccagag cggagccgag gtgaagaagc ccggctccag cgtgaaggtg       60
agctgcaagg ccagcggcta caccttcaag gactacacca tgcactgggt gagacaggcc      120
cctggacagg gcctggaatg gatcggcggc atctacccca caacggcgg ctccacctac       180 aaccagaact tcaaggacag ggtgaccctg accgccgaca gagcaccag caccgcttac       240 atggagctga gcagcctgag gagcgaggac accgccgtgt actactgcgc caggatgggc      300
taccacggcc ctcacctgga cttcgacgtg tggggccagg gcaccaccgt gacagtgagc      360
tccgcctcca ccaagggccc atcggtcttc cccctggcgc cctgctccag gagcacctcc      420
gagagcacag ccgccctggg ctgcctggtc aaggactact cccccgaacc ggtgacggtg      480
tcgtggaact caggcgctct gaccagcggc gtgcacacct tcccagctgt cctacagtcc      540
tcaggactct actccctcag cagcgtggtg accgtgccct ccagcaactt cggcacccag      600
acctacacct gcaacgtaga tcacaagccc agcaacacca aggtggacaa gacagttgag      660
cgcaaatgtt gtgtcgagtg cccaccgtgc ccagcaccac ctgccgcagc cagctcagtc      720

| | |
|---|---|
| ttcctcttcc ccccaaaacc caaggacacc ctcatgatct cccggacccc tgaggtcacg | 780 |
| tgcgtggtgg tggacgtgag cgccgaagac cccgaggtcc agttcaactg gtacgtggac | 840 |
| ggcgtggagg tgcataatgc caagacaaag ccacgggagg agcagttcaa cagcacgttc | 900 |
| cgtgtggtca gcgtcctcac cgttctgcac caggactggc tgaacggcaa ggagtacaag | 960 |
| tgcaaggtct ccaacaaagg cctcccatcc tccatcgaga aaaccatctc caaaaccaaa | 1020 |
| gggcagcccc gagaaccaca ggtgtacacc ctgcccccat cccgggagga gatgaccaag | 1080 |
| aaccaggtca gcctgacctg cctggtcaaa ggcttctacc ccagcgacat cgccgtggag | 1140 |
| tgggagagca atgggcagcc ggagaacaac tacaagacca cacctcccat gctggactcc | 1200 |
| gacggctcct tcttcctcta cagcaagctc accgtggaca agagcaggtg gcagcagggg | 1260 |
| aacgtcttct catgctccgt gatgcatgag gctctgcaca accactacac gcagaagagc | 1320 |
| ctctccctgt ctccgggtaa a | 1341 |

<210> SEQ ID NO 47
<211> LENGTH: 642
<212> TYPE: DNA
<213> ORGANISM: Artificial Sequence
<220> FEATURE:
<223> OTHER INFORMATION: OX40SF2_LC cDNA

<400> SEQUENCE: 47

| | |
|---|---|
| gacatccaga tgacccagag ccctagcagc ctgagcgcta gcgtgggcga cagagtgacc | 60 |
| atcacctgca aggccagcca ggatgtggga gccgccgtgg cctggtatca gcagaagccc | 120 |
| ggaaaggccc ccaagctgct gatctactgg gccagcacca gacacaccgg cgtgcctagc | 180 |
| aggtttagcg gcagcggcag cggcaccgac tttaccctga ccatcagcag cctgcagccc | 240 |
| gaggatttcg ccacctacta ctgccagcag tacatcaact accccctgac cttcggcggc | 300 |
| ggcaccaaag tggagatcaa gcgtacggtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gt | 642 |

<210> SEQ ID NO 48
<211> LENGTH: 1692
<212> TYPE: DNA
<213> ORGANISM: Artificial Sequence
<220> FEATURE:
<223> OTHER INFORMATION: hcOX40SF2IgG2sigma _R2BS6_HC-C cDNA

<400> SEQUENCE: 48

| | |
|---|---|
| caggtgcagc tggtccagag cggagccgag gtgaagaagc ccggctccag cgtgaaggtg | 60 |
| agctgcaagg ccagcggcta caccttcaag gactacacca tgcactgggt gagacaggcc | 120 |
| cctggacagg gcctggaatg gatcggcggc atctacccca caacggcgg ctccacctac | 180 |
| aaccagaact tcaaggacag ggtgaccctg accgccgaca gagcaccag caccgcttac | 240 |
| atggagctga gcagcctgag gagcgaggac accgccgtgt actactgcgc caggatgggc | 300 |
| taccacggcc tcacctgga cttcgacgtg tggggccagg gcaccaccgt gacagtgagc | 360 |
| tccgcctcca ccaagggccc atcggtcttc cccctggcgc cctgctccag gagcacctcc | 420 |
| gagagcacag ccgccctggg ctgcctggtc aaggactact cccccgaacc ggtgacggtg | 480 |

```
tcgtggaact caggcgctct gaccagcggc gtgcacacct tcccagctgt cctacagtcc    540
tcaggactct actccctcag cagcgtggtg accgtgccct ccagcaactt cggcacccag    600
acctacacct gcaacgtaga tcacaagccc agcaacacca aggtggacaa gacagttgag    660
cgcaaatgtt gtgtcgagtg cccaccgtgc ccagcaccac ctgccgcagc cagctcagtc    720
ttcctcttcc ccccaaaacc caaggacacc ctcatgatct cccggacccc tgaggtcacg    780
tgcgtggtgg tggacgtgag cgccgaagac cccgaggtcc agttcaactg gtacgtggac    840
ggcgtggagg tgcataatgc caagacaaag ccacgggagg agcagttcaa cagcacgttc    900
cgtgtggtca gcgtcctcac cgttctgcac caggactggc tgaacggcaa ggagtacaag    960
tgcaaggtct ccaacaaagg cctcccatcc tccatcgaga aaaccatctc aaaaccaaa   1020 gggcagcccc gagaaccaca ggtgtacacc ctgcccccat cccgggagga tgaccaag    1080 aaccaggtca gcctgacctg cctggtcaaa ggcttctacc ccagcgacat cgccgtggag   1140
tgggagagca tgggcagcc ggagaacaac tacaagacca cacctcccat gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctccctgt ctccgggtaa aggaggcgga gggagtggcg ggggaggctc tggcggcgga   1380
ggatccggcg gcggaggaag cctgccggcg ccgaaaaacc tggttgtttc tcgtgttacc   1440
gaagactctg cgcgtctgtc ttggaccgcg ccggacgcgg cgttcgactc tttcctgatc   1500
cagtaccagg aatctgaaaa agttggtgaa gcgatcgtgc tgaccgttcc gggttctgaa   1560
cgttcttacg acctgaccgg tctgaaaccg ggtaccgaat acaccgtttc tatctacggt   1620
gttcaatatg cggcgtggta tctgccgcgt caccacgagg cgagcaaccc gctgtctgcg   1680
atcttcacca cc                                                      1692
```

<210> SEQ ID NO 49
<211> LENGTH: 1668
<212> TYPE: DNA
<213> ORGANISM: Artificial Sequence
<220> FEATURE:
<223> OTHER INFORMATION: hcOX40SF2IgG2sigma _R2BS9_HC-C cDNA

<400> SEQUENCE: 49

```
caggtgcagc tggtccagag cggagccgag gtgaagaagc ccggctccag cgtgaaggtg     60
agctgcaagg ccagcggcta caccttcaag gactacacca tgcactgggt gagacaggcc    120
cctggacagg gcctggaatg gatcggcggc atctacccca caacggcgg ctccacctac    180 aaccagaact tcaaggacag ggtgaccctg accgccgaca gagcaccag caccgcttac    240 atggagctga gcagcctgag gagcgaggac accgccgtgt actactgcgc caggatgggc    300
taccacggcc ctcacctgga cttcgacgtg tggggccagg gcaccaccgt gacagtgagc    360
tccgcctcca ccaagggccc atcggtcttc cccctggcgc cctgctccag gagcacctcc    420
gagagcacag ccgccctggg ctgcctggtc aaggactact cccccgaacc ggtgacggtg    480
tcgtggaact caggcgctct gaccagcggc gtgcacacct tcccagctgt cctacagtcc    540
tcaggactct actccctcag cagcgtggtg accgtgccct ccagcaactt cggcacccag    600
acctacacct gcaacgtaga tcacaagccc agcaacacca aggtggacaa gacagttgag    660
cgcaaatgtt gtgtcgagtg cccaccgtgc ccagcaccac ctgccgcagc cagctcagtc    720
ttcctcttcc ccccaaaacc caaggacacc ctcatgatct cccggacccc tgaggtcacg    780
```

```
tgcgtggtgg tggacgtgag cgccgaagac cccgaggtcc agttcaactg gtacgtggac    840
ggcgtggagg tgcataatgc caagacaaag ccacgggagg agcagttcaa cagcacgttc    900
cgtgtggtca gcgtcctcac cgttctgcac caggactggc tgaacggcaa ggagtacaag    960
tgcaaggtct ccaacaaagg cctcccatcc tccatcgaga aaaccatctc caaaaccaaa   1020
gggcagcccc gagaaccaca ggtgtacacc ctgcccccat cccgggagga gatgaccaag   1080
aaccaggtca gcctgacctg cctggtcaaa ggcttctacc ccagcgacat cgccgtggag   1140
tgggagagca atgggcagcc ggagaacaac tacaagacca cacctcccat gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctccctgt ctccgggtaa aggaggcgga gggagtggcg ggggaggctc tggcggcgga   1380
ggatccggcg gcggaggaag cctgccggcg ccgaaaaacc tggttgtttc tcgtgttacc   1440
gaagactctg cgcgtctgtc ttggaccgcg ccggacgcgg cgttcgactc tttctggatt   1500
tattacctgg agtattggcg tggcggtgaa gcgatcgttc tgaccgttcc gggttctgaa   1560
cgttcttacg acctgaccgg tctgaaaccg ggtaccgaat atttcgttca aattcacggc   1620
gttaagggcg tcaatatag ttatccactg tctgcgatct tcaccacc                 1668
```

<210> SEQ ID NO 50
<211> LENGTH: 1668
<212> TYPE: DNA
<213> ORGANISM: Artificial Sequence
<220> FEATURE:
<223> OTHER INFORMATION: hcOX40SF2IgG2sigma _R2BS12_HC-C cDNA

<400> SEQUENCE: 50

```
caggtgcagc tggtccagag cggagccgag gtgaagaagc ccggctccag cgtgaaggtg     60
agctgcaagg ccagcggcta caccttcaag gactacacca tgcactgggt gagacaggcc    120
cctggacagg gcctggaatg gatcggcggc atctacccca caacggcgg ctccacctac    180 aaccagaact tcaaggacag ggtgaccctg accgccgaca gagcaccag caccgcttac    240 atggagctga gcagcctgag gagcgaggac accgccgtgt actactgcgc caggatgggc    300
taccacggcc ctcacctgga cttcgacgtg tggggccagg gcaccaccgt gacagtgagc    360
tccgcctcca ccaagggccc atcggtcttc cccctggcgc cctgctccag gagcacctcc    420
gagagcacag ccgccctggg ctgcctggtc aaggactact tccccgaacc ggtgacggtg    480
tcgtggaact caggcgctct gaccagcggc gtgcacacct tcccagctgt cctacagtcc    540
tcaggactct actccctcag cagcgtggtg accgtgccct ccagcaactt cggcacccag    600
acctacacct gcaacgtaga tcacaagccc agcaacacca aggtggacaa gacagttgag    660
cgcaaatgtt gtgtcgagtg cccaccgtgc ccagcaccac ctgccgcagc cagctcagtc    720
ttcctcttcc ccccaaaacc caaggacacc ctcatgatct cccggacccc tgaggtcacg    780
tgcgtggtgg tggacgtgag cgccgaagac cccgaggtcc agttcaactg gtacgtggac    840
ggcgtggagg tgcataatgc caagacaaag ccacgggagg agcagttcaa cagcacgttc    900
cgtgtggtca gcgtcctcac cgttctgcac caggactggc tgaacggcaa ggagtacaag    960
tgcaaggtct ccaacaaagg cctcccatcc tccatcgaga aaaccatctc caaaaccaaa   1020
gggcagcccc gagaaccaca ggtgtacacc ctgcccccat cccgggagga gatgaccaag   1080
aaccaggtca gcctgacctg cctggtcaaa ggcttctacc ccagcgacat cgccgtggag   1140
tgggagagca atgggcagcc ggagaacaac tacaagacca cacctcccat gctggactcc   1200
```

```
gacggctcct tcttcctcta cagcaagctc accgtggaca agagcaggtg gcagcagggg      1260
aacgtcttct catgctccgt gatgcatgag gctctgcaca accactacac gcagaagagc      1320
ctctccctgt ctccgggtaa aggaggcgga gggagtggcg ggggaggctc tggcggcgga      1380
ggatccggcg gcggaggaag cctgccggcg ccgaaaaacc tggttgtttc tcgtgttacc      1440
gaagactctg cgcgtctgtc ttggaccgcg ccggacgcgg cgttcgactc ttttctgatc      1500
gcgtatgcga atattggga gggcggtgaa gcggtcgttc tgaccgttcc gggttctgaa      1560
cgttcttacg acctgaccgg tctgaaaccg ggtaccgaat atttcgttca aatcaatggc      1620
gttaagggtg gtttctggag tatcccactg tctgcgatct tcaccacc                  1668
```

<210> SEQ ID NO 51
<211> LENGTH: 1668
<212> TYPE: DNA
<213> ORGANISM: Artificial Sequence
<220> FEATURE:
<223> OTHER INFORMATION: hcOX40SF2IgG2sigma _R2BS26_HC-C cDNA

<400> SEQUENCE: 51

```
caggtgcagc tggtccagag cggagccgag gtgaagaagc ccggctccag cgtgaaggtg        60
agctgcaagg ccagcggcta caccttcaag gactacacca tgcactgggt gagacaggcc      120
cctggacagg gcctggaatg gatcggcggc atctacccca caacggcgg ctccaccttac     180 aaccagaact tcaaggacag ggtgaccctg accgccgaca agagcaccag caccgcttac      240
atggagctga gcagcctgag gagcgaggac accgccgtgt actactgcgc caggatgggc      300
taccacggcc ctcacctgga cttcgacgtg tggggccagg gcaccaccgt gacagtgagc      360
tccgcctcca caagggccc atcggtcttc cccctggcgc cctgctccag gagcacctcc      420
gagagcacag ccgccctggg ctgcctggtc aaggactact tccccgaacc ggtgacggtg      480
tcgtggaact caggcgctct gaccagcggc gtgcacacct tcccagctgt cctacagtcc      540
tcaggactct actccctcag cagcgtggtg accgtgccct ccagcaactt cggcacccag      600
acctacacct gcaacgtaga tcacaagccc agcaacacca aggtggacaa gacagttgag      660
cgcaaatgtt gtgtcgagtg cccaccgtgc ccagcaccac ctgccgcagc cagctcagtc      720
ttcctcttcc ccccaaaacc caaggacacc ctcatgatct cccggacccc tgaggtcacg      780
tgcgtggtgg tggacgtgag cgccgaagac cccgaggtcc agttcaactg gtacgtggac      840
ggcgtggagg tgcataatgc caagacaaag ccacgggagg agcagttcaa cagcacgttc      900
cgtgtggtca gcgtcctcac cgttctgcac caggactggc tgaacggcaa ggagtacaag      960
tgcaaggtct ccaacaaagg cctcccatcc tccatcgaga aaaccatctc caaaaccaaa     1020
gggcagcccc gagaaccaca ggtgtacacc ctgcccccat cccgggagga gatgaccaag     1080
aaccaggtca gcctgacctg cctggtcaaa ggcttctacc ccagcgacat cgccgtggag     1140
tgggagagca atgggcagcc ggagaacaac tacaagacca cacctcccat gctggactcc     1200
gacggctcct tcttcctcta cagcaagctc accgtggaca agagcaggtg gcagcagggg     1260
aacgtcttct catgctccgt gatgcatgag gctctgcaca accactacac gcagaagagc     1320
ctctccctgt ctccgggtaa aggaggcgga gggagtggcg ggggaggctc tggcggcgga     1380
ggatccggcg gcggaggaag cctgccggcg ccgaaaaacc tggttgtttc tcgtgttacc     1440
gaagactctg cgcgtctgtc ttggaccgcg ccggacgcgg cgttcgactc ttttctgatc     1500
gcgtatatcg agtattggac tggcggtgaa gcgatcgttc tgaccgttcc gggttctgaa     1560
```
cgttcttacg acctgaccgg tctgaaaccg ggtaccgaat atttcgtttg gattcacggc    1620
gttaagggtg gtgcgtggtc cagcccgctg tctgcgatct tcaccacc                1668

<210> SEQ ID NO 52
<211> LENGTH: 1668
<212> TYPE: DNA
<213> ORGANISM: Artificial Sequence
<220> FEATURE:
<223> OTHER INFORMATION: hcOX40SF2IgG2sigma _R2BS29_HC-C cDNA

<400> SEQUENCE: 52
caggtgcagc tggtccagag cggagccgag gtgaagaagc ccggctccag cgtgaaggtg      60
agctgcaagg ccagcggcta caccttcaag gactacacca tgcactgggt gagacaggcc     120
cctggacagg gcctggaatg gatcggcggc atctacccca caacggcgg ctccacctac      180 aaccagaact tcaaggacag ggtgaccctg accgccgaca gagcaccag caccgcttac      240 atggagctga gcagcctgag gagcgaggac accgccgtgt actactgcgc caggatgggc     300
taccacggcc ctcacctgga cttcgacgtg tggggccagg gcaccaccgt gacagtgagc     360
tccgcctcca ccaagggccc atcggtcttc cccctggcgc cctgctccag gagcacctcc     420
gagagcacag ccgccctggg ctgcctggtc aaggactact cccccgaacc ggtgacggtg     480
tcgtggaact caggcgctct gaccagcggc gtgcacacct cccagctgt cctacagtcc      540 tcaggactct actccctcag cagcgtggtg accgtgccct ccagcaactt cggcacccag     600
acctacacct gcaacgtaga tcacaagccc agcaacacca aggtggacaa gacagttgag     660
cgcaaatgtt gtgtcgagtg cccaccgtgc ccagcaccac ctgccgcagc cagctcagtc     720
ttcctcttcc ccccaaaacc caaggacacc ctcatgatct cccggacccc tgaggtcacg     780
tgcgtggtgg tggacgtgag cgccgaagac cccgaggtcc agttcaactg gtacgtggac     840
ggcgtggagg tgcataatgc caagacaaag ccacgggagg agcagttcaa cagcacgttc     900
cgtgtggtca gcgtcctcac cgttctgcac caggactggc tgaacggcaa ggagtacaag     960
tgcaaggtct ccaacaaagg cctcccatcc tccatcgaga aaaccatctc caaaaccaaa    1020
gggcagcccc gagaaccaca ggtgtacacc ctgcccccat cccgggagga gatgaccaag    1080
aaccaggtca gcctgacctg cctggtcaaa ggcttctacc ccagcgacat cgccgtggag    1140
tgggagagca atgggcagcc ggagaacaac tacaagacca cacctcccat gctggactcc    1200
gacggctcct tcttcctcta cagcaagctc accgtggaca gagcaggtg gcagcagggg    1260 aacgtcttct catgctccgt gatgcatgag gctctgcaca accactacac gcagaagagc    1320
ctctccctgt ctccgggtaa aggaggcgga gggagtggcg ggggaggctc tggcggcgga    1380
ggatccggcg gcgaggaag cctgcccgcc ccaagaacc tggtggtgag cagggtgacc    1440
gaggacagcg ccaggctgag ctggacagct cctgacgccg ccttcgacag cttccccatc    1500
tattactggg agtacagggt gggcggagag gccatcgtgc tgacagtgcc cggcagcgag    1560
aggagctacg acctgaccgg cctgaagcct ggcaccgagt acttcgtgta catcaacggc    1620
gtgaagggcg gcgaggaatc cagacccctg agcgccatct tcaccacc                1668

<210> SEQ ID NO 53
<211> LENGTH: 1689
<212> TYPE: DNA
<213> ORGANISM: Artificial Sequence
<220> FEATURE:
<223> OTHER INFORMATION: hcOX40SF2IgG2sigma _R2BS39_HC-C cDNA

<400> SEQUENCE: 53

```
caggtgcagc tggtccagag cggagccgag gtgaagaagc ccggctccag cgtgaaggtg      60
agctgcaagg ccagcggcta caccttcaag gactacacca tgcactgggt gagacaggcc     120
cctggacagg gcctggaatg gatcggcggc atctacccca caacggcgg ctccacctac      180 aaccagaact tcaaggacag ggtgaccctg accgccgaca gagcaccag caccgcttac      240 atggagctga gcagcctgag gagcgaggac accgccgtgt actactgcgc caggatgggc     300
taccacggcc ctcacctgga cttcgacgtg tggggccagg gcaccaccgt gacagtgagc     360
tccgcctcca ccaagggccc atcggtcttc cccctggcgc cctgctccag gagcacctcc     420
gagagcacag ccgccctggg ctgcctggtc aaggactact cccccgaacc ggtgacggtg     480
tcgtggaact caggcgctct gaccagcggc gtgcacacct cccagctgt cctacagtcc      540 tcaggactct actccctcag cagcgtggtg accgtgccct ccagcaactt cggcacccag     600
acctacacct gcaacgtaga tcacaagccc agcaacacca aggtggacaa gacagttgag     660
cgcaaatgtt gtgtcgagtg cccaccgtgc ccagcaccac ctgccgcagc cagctcagtc     720
ttcctcttcc ccccaaaacc caaggacacc ctcatgatct cccggacccc tgaggtcacg     780
tgcgtggtgg tggacgtgag cgccgaagac cccgaggtcc agttcaactg gtacgtggac     840
ggcgtggagg tgcataatgc caagacaaag ccacgggagg agcagttcaa cagcacgttc     900
cgtgtggtca gcgtcctcac cgttctgcac caggactggc tgaacggcaa ggagtacaag     960
tgcaaggtct ccaacaaagg cctcccatcc tccatcgaga aaaccatctc caaaaccaaa    1020
gggcagcccc gagaaccaca ggtgtacacc ctgcccccat cccgggagga gatgaccaag    1080
aaccaggtca gcctgacctg cctggtcaaa ggcttctacc ccagcgacat cgccgtggag    1140
tgggagagca atgggcagcc ggagaacaac tacaagacca cacctcccat gctggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctcccctg tctccgggta aaggaggcgga gggagtggcg gggaggctc tggcggcgga    1380 ggatccggcg gcggaggaag cctgccggcg ccgaaaaacc tggttgtttc tcgtgttacc    1440
gaagactctg cgcgtctgtc ttggaccgcg ccggacgcgg cgttcgactc tttcctgatc    1500
cagtaccagg aatctgaaaa agttggtgaa gcgatcgtgc tgaccgttcc gggttctgaa    1560
cgttcttacg acctgaccgg tctgaaaccg ggtaccgaat acaccgtttc tatctacggt    1620
gtgagccacg gccgtggtg taattatggc gagtggcgtt ctaacccgct gtctgcgatc    1680
ttcaccacc                                                           1689
```

<210> SEQ ID NO 54
<211> LENGTH: 1668
<212> TYPE: DNA
<213> ORGANISM: Artificial Sequence
<220> FEATURE:
<223> OTHER INFORMATION: hcOX40SF2IgG2sigma _R2BS56_HC-C cDNA

<400> SEQUENCE: 54

```
caggtgcagc tggtccagag cggagccgag gtgaagaagc ccggctccag cgtgaaggtg      60
agctgcaagg ccagcggcta caccttcaag gactacacca tgcactgggt gagacaggcc     120
cctggacagg gcctggaatg gatcggcggc atctacccca caacggcgg ctccacctac      180 aaccagaact tcaaggacag ggtgaccctg accgccgaca gagcaccag caccgcttac      240 atggagctga gcagcctgag gagcgaggac accgccgtgt actactgcgc caggatgggc     300
```

```
taccacggcc ctcacctgga cttcgacgtg tggggccagg gcaccaccgt gacagtgagc    360
tccgcctcca ccaagggccc atcggtcttc ccctggcgc cctgctccag gagcacctcc    420
gagagcacag ccgccctggg ctgcctggtc aaggactact tccccgaacc ggtgacggtg    480
tcgtggaact caggcgctct gaccagcggc gtgcacacct tcccagctgt cctacagtcc    540
tcaggactct actccctcag cagcgtggtg accgtgccct ccagcaactt cggcacccag    600
acctacacct gcaacgtaga tcacaagccc agcaacacca aggtggacaa gacagttgag    660
cgcaaatgtt gtgtcgagtg cccaccgtgc ccagcaccac ctgccgcagc cagctcagtc    720
ttcctcttcc ccccaaaacc caaggacacc ctcatgatct cccggacccc tgaggtcacg    780
tgcgtggtgg tggacgtgag cgccgaagac cccgaggtcc agttcaactg gtacgtggac    840
ggcgtggagg tgcataatgc caagacaaag ccacgggagg agcagttcaa cagcacgttc    900
cgtgtggtca gcgtcctcac cgttctgcac caggactggc tgaacggcaa ggagtacaag    960
tgcaaggtct ccaacaaagg cctcccatcc tccatcgaga aaaccatctc caaaaccaaa   1020
gggcagcccc gagaaccaca ggtgtacacc ctgcccccat cccgggagga gatgaccaag   1080
aaccaggtca gcctgacctg cctggtcaaa ggcttctacc ccagcgacat cgccgtggag   1140
tgggagagca atgggcagcc ggagaacaac tacaagacca cacctcccat gctggactcc   1200
gacggctcct tcttcctcta cagcaagctc accgtggaca gagcaggtg gcagcagggg   1260
aacgtcttct catgctccgt gatgcatgag gctctgcaca accactacac gcagaagagc   1320
ctctccctgt ctccgggtaa aggaggcgga gggagtggcg ggggaggctc tggcggcgga   1380
ggatccggcg gcgaggaag cctgccggcg ccgaaaaacc tggttgtttc tcgtgttacc   1440
gaagactctg cgcgtctgtc ttggaccgcg ccggacgcgg cgttcgactc ttttagcatt   1500
gcgtactggg agtatcgtaa aggcggtgaa gcgatcgttc tgaccgttcc gggttctgaa   1560
cgttcttacg acctgaccgg tctgaaaccg ggtaccgaat atttcgttct gatctatggt   1620
gtcaagggcg gttggcaatc caaaccactg tctgcgatct tcaccacc                1668
```

<210> SEQ ID NO 55
<211> LENGTH: 1353
<212> TYPE: DNA
<213> ORGANISM: Artificial Sequence
<220> FEATURE:
<223> OTHER INFORMATION: hcOX40SF2IgG1_HC

<400> SEQUENCE: 55

```
caggtgcagc tggtccagag cggagccgag gtgaagaagc ccggctccag cgtgaaggtg     60
agctgcaagg ccagcggcta caccttcaag gactacacca tgcactgggt gagacaggcc    120
cctggacagg gcctggaatg gatcggcggc atctacccca caacggcgg ctccacctac    180
aaccagaact tcaaggacag ggtgaccctg accgccgaca gagcaccag caccgcttac    240
atggagctga gcagcctgag gagcgaggac accgccgtgt actactgcgc aggatgggc    300
taccacggcc ctcacctgga cttcgacgtg tggggccagg gcaccaccgt gacagtgagc    360
tccgcctcca ccaagggccc atcggtcttc ccctggcac cctcctccaa gagcacctct    420
gggggcacag cggccctggg ctgcctggtc aaggactact tccccgaacc ggtgacggtg    480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gaaagttgag    660
cccaaatctt gtgacaaaac tcacacatgc ccaccgtgcc cagcacctga actcctgggg    720
```

```
ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag ccccatcga gaaaaccatc   1020 tccaaagcca aagggcagcc ccgagaacca caggtgtaca ccctgccccc atcccgggag   1080
gagatgacca agaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaa                                1353
```

<210> SEQ ID NO 56
<211> LENGTH: 1668
<212> TYPE: DNA
<213> ORGANISM: Artificial Sequence
<220> FEATURE:
<223> OTHER INFORMATION: hcOX40SF2IgG2sigma_R2BS29_HC-N cDNA

<400> SEQUENCE: 56

```
ctgcccgccc ccaagaacct ggtcgtcagc agagtgaccg aggactccgc cagactgagc     60
tggacagccc ctgacgccgc cttcgattcc ttccccatct actactggga gtacagagtg    120
ggcggagagg ccatcgtgct gaccgtgcct ggctccgaga ggtcctacga cctgaccggc    180
ctgaagcctg gcaccgagta cttcgtgtac atcaacggcg tgaagggcgg agaggagtcc    240
agacccctga gcgccatttt caccacaggc ggcggcggct ccggcggagg cggctccggc    300
ggaggaggaa gcggcggcgg agggagccaa gtgcagctcg tgcagtccgg cgctgaggtg    360
aagaaacctg gctccagcgt caaggtgagc tgcaaggcca gcggctacac cttcaaggac    420
tacaccatgc actgggtgag gcaagcccct ggccaaggcc tggagtggat cggaggcatc    480
taccccaaca cggcggctc cacctataac cagaatttca aggacagggt gaccctgacc    540
gccgacaaga gcaccagcac cgcctacatg gagctgagca gcctgagatc cgaggacacc    600
gccgtgtact actgcgccag gatgggctat cacggccccc acctggactt tgacgtgtgg    660
ggccagggca acccgtcac cgtgtccagc gcctccacca agggcccatc ggtcttcccc    720
ctggcgccct gctccaggag cacctccgag agcacagccg ccctgggctg cctggtcaag    780
gactacttcc ccgaaccggt gacggtgtcg tggaactcag gcgctctgac cagcggcgtg    840
cacaccttcc cagctgtcct acagtcctca ggactctact ccctcagcag cgtggtgacc    900
gtgccctcca gcaacttcgg cacccagacc tacacctgca acgtagatca caagcccagc    960
aacaccaagg tggacaagac agttgagcgc aaatgttgtg tcgagtgccc accgtgccca   1020
gcaccacctg ccgcagccag ctcagtcttc ctcttccccc caaaacccaa ggacaccctc   1080
atgatctccc ggacccctga ggtcacgtgc gtggtggtgg acgtgagcgc cgaagacccc   1140
gaggtccagt tcaactggta cgtggacggc gtggaggtgc ataatgccaa gacaaagcca   1200
cgggaggagc agttcaacag cacgttccgt gtggtcagcg tcctcaccgt tctgcaccag   1260
gactggctga acggcaagga gtacaagtgc aaggtctcca acaaaggcct cccatcctcc   1320
atcgagaaaa ccatctccaa aaccaaaggg cagccccgag aaccacaggt gtacaccctg   1380
```

| | |
|---|---|
| cccccatccc gggaggagat gaccaagaac caggtcagcc tgacctgcct ggtcaaaggc | 1440 |
| ttctacccca gcgacatcgc cgtggagtgg gagagcaatg ggcagccgga gaacaactac | 1500 |
| aagaccacac ctcccatgct ggactccgac ggctccttct tcctctacag caagctcacc | 1560 |
| gtggacaaga gcaggtggca gcaggggaac gtcttctcat gctccgtgat gcatgaggct | 1620 |
| ctgcacaacc actacacgca gaagagcctc tccctgtctc cgggtaaa | 1668 |

<210> SEQ ID NO 57
<211> LENGTH: 969
<212> TYPE: DNA
<213> ORGANISM: Artificial Sequence
<220> FEATURE:
<223> OTHER INFORMATION: lcOX40SF2_R2BS29_LC-N cDNA

<400> SEQUENCE: 57

| | |
|---|---|
| ctgcctgccc ccaagaacct ggtggtgagc agagtgaccg aggatagcgc cagactgtcc | 60 |
| tggacagccc ccgatgccgc cttcgactcc ttccccatct attactggga gtacaggggtg | 120 |
| ggaggcgagg ccatcgtgct gaccgtgcct ggctccgaga ggagctacga tctgaccggc | 180 |
| ctgaagcccg gcaccgagta cttcgtgtac atcaacggcg tcaaggggagg cgaggagagc | 240 |
| agaccctgt ccgccatctt caccacagga ggcggcggca gcggcggcgg aggcagcggc | 300 |
| ggcggaggct ccggcggcgg cggcagcgat atccagatga cccagagccc cagctccctg | 360 |
| tccgctagcg tgggcgacag agtgaccatc acctgcaagg ctagccagga cgtgggcgct | 420 |
| gctgtggcct ggtatcagca gaagcccggc aaggccccca agctgctgat ctactgggcc | 480 |
| tccacaaggc acaccggagt gcccagcaga ttttccggca cgggcagcgg caccgatttc | 540 |
| accctgacca tcagctccct gcagcccgag gacttcgcca cctactactg ccagcagtac | 600 |
| atcaattacc ccctgacctt cggcggaggc accaaggtgg agatcaaacg tacggtggct | 660 |
| gcaccatctg tcttcatctt cccgccatct gatgagcagt tgaaatctgg aactgcctct | 720 |
| gttgtgtgcc tgctgaataa cttctatccc agagaggcca agtacagtg gaaggtggat | 780 |
| aacgccctcc aatcgggtaa ctcccaggag agtgtcacag agcaggacag caaggacagc | 840 |
| acctacagcc tcagcagcac cctgacgctg agcaaagcag actacgagaa acacaaagtc | 900 |
| tacgcctgcg aagtcaccca tcagggcctg agctcgcccg tcacaaagag cttcaacagg | 960 |
| ggagagtgt | 969 |

<210> SEQ ID NO 58
<211> LENGTH: 972
<212> TYPE: DNA
<213> ORGANISM: Artificial Sequence
<220> FEATURE:
<223> OTHER INFORMATION: lcOX40SF2_R2BS29_LC-C cDNA

<400> SEQUENCE: 58

| | |
|---|---|
| gacatccaga tgacccagag ccccagcagc ctgtctgcca gcgtgggcga cagagtgacc | 60 |
| atcacatgca aggccagcca ggacgtggga gccgccgtgg cttggtatca gcagaagcct | 120 |
| ggcaaggccc ccaagctgct gatctactgg gccagcacca gacacaccgg cgtgcccagc | 180 |
| agattttctg gcagcggctc cggcaccgac ttcaccctga caatcagctc cctgcagccc | 240 |
| gaggacttcg ccacctacta ctgccagcag tacatcaact accccctgac cttcggcgga | 300 |
| ggcaccaagg tggaaatcaa gcgtacggtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |

```
gagagtgtca cagagcagga cagcaaggac agcacctaca gcctcagcag caccctgacg    540
ctgagcaaag cagactacga aaacacaaa gtctacgcct gcgaagtcac ccatcagggc    600
ctgagctcgc ccgtcacaaa gagcttcaac aggggagagt gtggcggcgg cggcagcggc    660
ggcggcggca gcggcggcgg cggcagcggc ggaggaggat ccatgctgcc tgcccccaag    720
aacctggtgg tgagcagggt gaccgaggac agcgccagac tgagctggac agctcccgac    780
gccgccttcg actccttccc catctactac tgggagtaca gagtgggcgg cgaagccatt    840
gtgctgaccg tgcccggcag cgagaggagc tacgacctga ccggcctgaa gcccggcacc    900
gagtacttcg tgtacatcaa cggcgtgaag ggcggcgaag agagcaggcc tctgagcgcc    960
atcttcacca ca    972
```

<210> SEQ ID NO 59
<211> LENGTH: 1680
<212> TYPE: DNA
<213> ORGANISM: Artificial Sequence
<220> FEATURE:
<223> OTHER INFORMATION: hcOX40SF2IgG1 _R2BS29_HC-C cDNA
<400> SEQUENCE: 59

```
caggtgcagc tggtccagag cggagccgag gtgaagaagc ccggctccag cgtgaaggtg     60
agctgcaagg ccagcggcta cacctttcaag gactacacca tgcactgggt gagacaggcc    120
cctggacagg gcctggaatg gatcggcggc atctacccca caacggcgg ctccacctac    180 aaccagaact tcaaggacag ggtgaccctg accgccgaca gagcaccag caccgcttac    240 atggagctga gcagcctgag gagcgaggac accgccgtgt actactgcgc caggatgggc    300
taccacggcc ctcacctgga cttcgacgtg tggggccagg gcaccaccgt gacagtgagc    360
tccgcctcca ccaagggccc atcggtcttc cccctggcac cctcctccaa gagcacctct    420
gggggcacag cggccctggg ctgcctggtc aaggactact ccccgaacc ggtgacggtg    480 tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gaaagttgag    660
cccaaatctt gtgacaaaac tcacacatgc ccaccgtgcc cagcacctga actcctgggg    720
ggaccgtcag tcttcctctt ccccccaaaa cccaaggaca cctcatgat ctcccggacc    780 cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag cccccatcga gaaaaccatc   1020
tccaaagcca aagggcagcc ccgagaacca caggtgtaca ccctgccccc atcccgggag   1080
gagatgacca agaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaaggaggcg agggagtgg cggggaggc   1380 tctggcggcg gaggatccgg cggcggagga agcctgcccg cccccaagaa cctggtggtg   1440
agcagggtga ccgaggacag cgccaggctg agctggacag ctcctgacgc cgccttcgac   1500
```

-continued

```
agcttcccca tctattactg ggagtacagg gtgggcggag aggccatcgt gctgacagtg    1560
cccggcagcg agaggagcta cgacctgacc ggcctgaagc ctggcaccga gtacttcgtg    1620
tacatcaacg gcgtgaaggg cggcgaggaa tccagacccc tgagcgccat cttcaccacc    1680
```